(12) United States Patent
Wentzel et al.

(10) Patent No.: US 10,934,537 B2
(45) Date of Patent: Mar. 2, 2021

(54) THERMOSTABLE CELLULASES

(71) Applicant: SINTEF TTO AS, Trondheim (NO)

(72) Inventors: Alexander Wentzel, Trondheim (NO); Anna Sofia Lewin, Trondheim (NO); Mark Liles, Auburn, AL (US); Jinglie Zhou, Auburn, AL (US)

(73) Assignee: SINTEFF TTO AS, Trondheim (NO)

( * ) Notice: Subject to any disclaimer, the term of this patent is extended or adjusted under 35 U.S.C. 154(b) by 137 days.

(21) Appl. No.: 15/577,641

(22) PCT Filed: May 27, 2016

(86) PCT No.: PCT/EP2016/062079
§ 371 (c)(1),
(2) Date: Nov. 28, 2017

(87) PCT Pub. No.: WO2016/189158
PCT Pub. Date: Dec. 1, 2016

(65) Prior Publication Data
US 2018/0245060 A1    Aug. 30, 2018

(30) Foreign Application Priority Data
May 28, 2015    (GB) ..................... 1509149

(51) Int. Cl.
C12N 9/42    (2006.01)
C12P 19/02    (2006.01)
C12P 19/14    (2006.01)

(52) U.S. Cl.
CPC ............ *C12N 9/2437* (2013.01); *C12P 19/02* (2013.01); *C12P 19/14* (2013.01); *C12Y 302/01004* (2013.01)

(58) Field of Classification Search
None
See application file for complete search history.

(56) References Cited

U.S. PATENT DOCUMENTS

| 7,465,571 B1 | 12/2008 | Lam et al. |
| 7,960,148 B2 | 6/2011 | Steer et al. |
| 8,101,393 B2 | 1/2012 | Gray et al. |
| 2008/0233175 A1 | 9/2008 | Steer et al. |

FOREIGN PATENT DOCUMENTS

| WO | WO 2005/096804 A2 | 10/2005 |
| WO | WO 2007/094852 A2 | 8/2007 |

OTHER PUBLICATIONS

Alschul et al., (1997) Nucleic Acids Res., 25: 3389-3402 (On Order).
Database UniProt [Online] Mar. 16, 2016 (Mar. 16, 2016) "SubName: Full=Endoglucanase/endoxylanase {ECO:0000313| EMBL:ALV63957.1}", retrieved from EBI accession No. UNIPROT:A0A0U3SGP7 Database accession No. A0A0U3SGP7 (On Order).
Holm (1993) J. Mol. Biol., 23: 123-38 (On Order).
Holm (1995) Trends Biochem. Sci., 20: 478-480 (On Order).
Holm (1998) Nucleic Acid Rs., 26: 316-319 (On Order).
Kotlar et al, 2001, Environmental microbiology reports, 3: 674-681 (On Order).
Lewin Anna et al.: "The microbial communities in two apparently physically separated deep subsurface oil reservoirs show extensive DNA sequence similarities.", Environmental Microbiology, Feb. 2014, vol. 16, No. 2, pp. 545-558, ISSN: 1462-2920 (On Order).
Myers et al., (1988) CABIOS, 4:11-17 (On Order).
Pearson (1990), Methods Enzymol., 183: 63-98 (On Order).
Pearson et al., (1988) PNAS, 85: 2444-2448 (On Order).

(Continued)

*Primary Examiner* — Kagnew H Gebreyesus
(74) *Attorney, Agent, or Firm* — Lewis Roca Rothgerber Christie LLP

(57) ABSTRACT

The present invention relates to a nucleic acid molecule which encodes a polypeptide having cellulase activity and which is thermostable, wherein said nucleic acid molecule comprises or has a nucleotide sequence selected from:
i) a nucleotide sequence which encodes an amino acid sequence as set forth in SEQ ID NO. 2 or as set forth in SEQ ID NO. 8;
ii) a nucleotide sequence which encodes an amino acid sequence having at least 80% sequence identity to the amino acid sequence of (i);
iii) a nucleotide sequence which encodes a part of the amino acid sequence of (i);
iv) a nucleotide sequence which encodes a part of the amino acid sequence of (ii) wherein said part has at least 90% identity to an amino acid sequence of SEQ ID NO. 4, SEQ ID NO. 6, SEQ ID NO. 14, SEQ ID NO. 16, SEQ ID NO. 18 or SEQ ID NO. 20;
v) a nucleotide sequence as set forth in SEQ ID NO. 1 or as set forth in SEQ ID NO. 7;
vi) a nucleotide sequence having at least 80% sequence identity to the nucleotide sequence of v) or a nucleotide sequence which is degenerate thereto;
vii) a nucleotide sequence which is a part of the nucleotide sequence of v);
viii) a nucleotide sequence which is a part of the nucleotide sequence of vi) wherein said part has at least 90% identity to a nucleotide sequence of SEQ ID NO. 3, SEQ ID NO. 5, SEQ ID NO. 13, SEQ ID NO. 15, SEQ ID NO. 17 or SEQ ID NO. 19;
or a nucleic acid which comprises a nucleotide sequence which is complementary to the nucleotide sequence of any one of i) to vii).
The invention further relates to polypeptides encoded by such a nucleic acid molecule, to constructs, vectors and cells comprising the nucleic acid molecule and to a use and method of using a polypeptide of the invention for degrading cellulose.

Figure 1A:
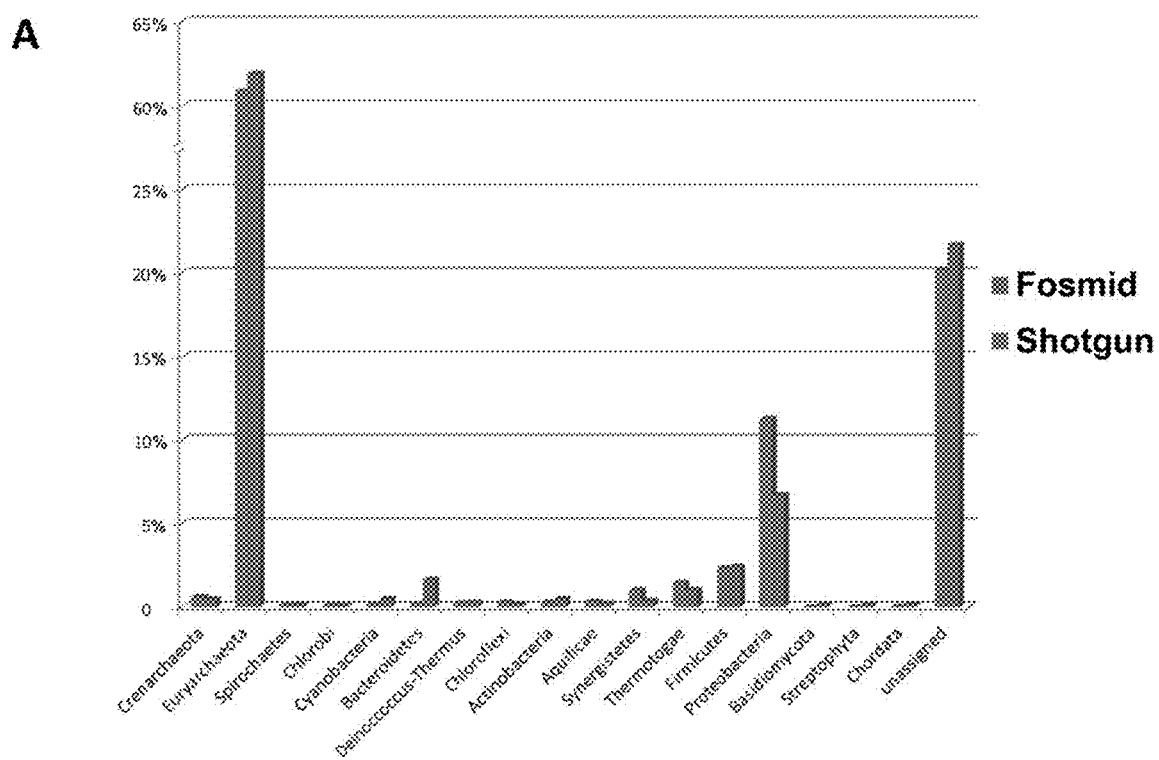

14 Claims, 9 Drawing Sheets
Specification includes a Sequence Listing.

(56) References Cited

OTHER PUBLICATIONS

Thompson et al., (1994) Nucleic Acids Res., 22: 4673-4680 (On Order).
Yennemalli et al., Biotechnol Biofuels 6:136, 2013 (On Order).
Altschul, Stephen F. et al.; "Gapped BLAST and PSI-BLAST: a new generation of protein database search programs"; Nucleic Acids Res.; 1997; vol. 25; No. 17; pp. 3389-3402.
Database UniProt [Online] Mar. 16, 2016 (Mar. 16, 2016) "SubName: Full=Endoglucanase/endoxylanase {ECO:0000313|EMBL:ALV63957. 1}", retrieved from EBI accession No. UNIPROT:A0A0U3SGP7 Database accession No. A0A0U3SGP7.
Holm, Liisa et al.; "Protein Structure Comparison by Alignment of Distance Matrices"; J. Mol. Biol.; 1993; 233; pp. 123-138.
Holm, Liisa et al.; "Dali: a network tool for protein structure comparison"; Trends Biochem. Sci.; 20; Nov. 1995; pp. 478-480.
Holm, Liisa et al.; "Touring protein fold space with Dali/FSSP"; Nucleic Acid Res.; 1998; vol. 26; No. 1; pp. 316-319.
Kotlar, Hans K. et al.; "High coverage sequencing of DNA from microorganisms living in an oil reservoir 2.5 kilometres subsurface"; Environmental microbiology reports; 2011; 3(6); pp. 674-681.
Lewin, Anna et al.; "The microbial communities in two apparently physically separated deep subsurface oil reservoirs show extensive DNA sequence similarities"; Environmental Microbiology; 2014; vol. 16, No. 2, pp. 545-558.
Myers, Eugene W. et al.; "Optimal alignments in linear space"; CABIOS; 1988; vol. 4; No. 1; pp. 11-17.
Pearson, William R. et al.; "Improved tools for biological sequence comparison"; Proc. Natl. Acad. Sci.; 1988; vol. 85; pp. 2444-2448.
Thompson, Julie D. et al.; "CLUSTAL W: improving the sensitivity of progressive multiple sequence alignment through sequence weighting, position-specific gap penalties and weight matrix choice"; Nucleic Acids Res.; 1994; vol. 22; No. 22; pp. 4673-4680.
Yennamalli, Ragothaman M. et al.; "Endoglucanases: insights into thermostability for biofuel applications"; Biotechnology for Biofuels; 2013; 6:136; 9pp.

SEQUENCE LISTING

<160> NUMBER OF SEQ ID NOS: 31

<210> SEQ ID NO 1
<211> LENGTH: 3969
<212> TYPE: DNA

<213> ORGANISM: Unknown
<220> FEATURE:
<223> OTHER INFORMATION: Thermostable cellulase from thermophilic archaeon

<400> SEQUENCE: 1

| | |
|---|---|
| atgtataggc aaaaggctct ggcagtgttt gttttgtttg ttgttttggc cggagtagcc | 60 |
| ggaagtatcc cagcaggcta cgcagcgacg aacaccagca cgtacacgac gcccacagga | 120 |
| atatactatg aagtcagagg ggatacaatc tacatgataa acgttgcaac gggagaggag | 180 |
| accccaatac acctctttgg agtcaactgg ttcggctttg agacaccgaa ctacgtcgtt | 240 |
| cacggcctat ggagtaggaa ctgggaggac atgctcctcc agatcaagag ccttggcttc | 300 |
| aatgcgataa ggcttccctt ctgtacccag tcagtaaaac cggggacgat gccaacgggg | 360 |
| attgactacg ccaagaaccc cgacctccag ggtcttgaca cgtccagat aatggagaaa | 420 |
| ataatcaaga aggctggaga cctgggcata ttcgtgctcc tcgactacca cagaatagga | 480 |
| tgcaacttca tagagcccct atggtacacc gacagcttct cggagcagga ctacataaac | 540 |
| acctggttg aagtcgccca gaggttcggc aagtactgga acgttatcgg cgcggacctg | 600 |
| aagaacgaac cccacagctc aagccccgca cctgctgcct acactgacgg aagtggggcc | 660 |
| acatggggaa tgggcaacaa cgccaccgac tggaacctgg cggctgagag gataggaaag | 720 |
| gcaatcctgg aggttgctcc gcactggctt atattcgttg agggaacaca gtttaccacc | 780 |
| cccgagatag acgtagcta caagtggggc cacaacgcct ggtggggcgg aaacctcatg | 840 |
| ggcgttagga agtacccagt caacctgccc aggaacaagc tcgtctacag cccccacgtt | 900 |
| tacggcccag acgtttacga ccagccctac tttgaccccg cagagggctt ccccgacaac | 960 |
| ttacccgaca tctggtacca ccacttcggc tacgtaaagc ttgatctcgg ttaccctgtt | 1020 |
| gttataggtg agttcggagg caagtacggc catgggggag acccgagaga cgtcacttgg | 1080 |
| cagaacaaga taatagactg gatgatccag aacaaattct gtgacttctt ctactggagc | 1140 |
| tggaacccca cagcggtga cacaggtgga attctgcagg atgactggac gacaatatgg | 1200 |
| gaggacaaat acaacaacct gaagaggctc atggacagct gctctggaaa cgccactgct | 1260 |
| ccgtccgtcc ccacgacaac tacaacaacc agtacaccgc caacaaccac aacgactaca | 1320 |
| acatccactc caacgaccac tacccagacc ccgaccacca ctactccaac tacgacaacc | 1380 |
| accacgacta caactccttc aaataacgtc ccatttgaaa ctgtgaacgt tctcccgact | 1440 |
| agctcccagt acgagggaac cagcgtggag gttgtatgtg atggaaccca gtgtgcctcc | 1500 |
| agcgtttggg gagctccgaa cctctgggga gtcgttaaga tcgaaacgc tacaatggac | 1560 |
| cccaacgttt ggggctggga ggacgtttac aagactgcac cccaggacat tggaaccggc | 1620 |
| agcacaaaga tggagataag gaacggggtg ctcaaggtta caaacctctg gaacatcaac | 1680 |
| atgcatccga agtacaacac aatggcatac ccggaggtca tatacggcgc caagccttgg | 1740 |
| ggcaaccagc caataaacgc tccgaacttc gtgctcccga taaaggtctc ccagcttccg | 1800 |
| aggatactcg ttgacacaaa gtacacgctc gaaaagagct tcccaggaaa caacttcgcc | 1860 |
| tttgaggcct ggctcttcaa ggatgccaac aacatgaggg caccaggcca ggggactac | 1920 |
| gagataatgg tacagctcta catcgagggc ggatatccag cgggctacga caaggggccg | 1980 |
| gttctcaccg ttgatgttcc aataatcgtt gatggaaggc ttttaaacca gactttgag | 2040 |
| ctctacgacg tcatagcgga tgccggatgg aggttcttca ccttcaagcc aactaagaac | 2100 |
| tacaacggct cagaggttgt gttcgactac accaaattca tagaaatagt tgacaactac | 2160 |

-continued

```
ctcggcggtg gcagcctcac gaaccactac ctgatgtccc tggaattcgg taccgagata    2220
tacaccaacg ggtgcacctc gttcccgtgc acagtggacg taaggtggac ccttgacaag    2280
tacaggttca tcctggcccc aggaacaatg gccactgagg aggccatgag agttctcgtc    2340
ggagaggtcc agcctcccgc ttccacaaca acatcgcaga cgactacttc aaccacaacc    2400
ccaacgccca ctaccactac tacgactcag acttcaacca ccactacaac cacctcaccg    2460
ccgacaacca ccgcacctgc tcaggacgta attaagctca ggtacccgga cgatgggcag    2520
tggcccgagg ccccaattga cagggatgga gacggaaacc cagagttcta catagaaata    2580
aacccgtgga acatactgag cgctgaaggc tacgccgaga tgacctacaa cttgagcagc    2640
ggggttctcc actacgtcca ggccctggat agtataaccc tcaaaaacgg cggtgcctgg    2700
gtgcacggat atcccgagat attctacggc aacaagccct ggaacaacaa ctcagccacc    2760
gatggagaag ttccactgcc tggaaaagtc tcgaacctga caacttcta cctgaccgtg    2820 agctacaagc tgctgccgaa gaacggactt ccaataaacc ttgcaatcga gtcatggctc    2880
acaagggagc cctggaggaa cagcggaata acagcgacga gcaggagct catgatatgg    2940 ctgtactacg acggactcca gccggccggc tcgaaggtca aggaaatcgt tgtcccgata    3000
gtggtgaacg cactccagt gaacgctacc ttcgaggtct ggaaggcgaa catcggctgg    3060
gagtacgtag ccttcagaat aaagacccca ataaggagg aaccgttac cataccgtac    3120 ggagctttca taagccgccgc cgcgaacgta acgagcctag ccaactaccc cgagctgtac    3180
ctggaagacg ttgaggttgg aaccgaatac ggaacgccct caaccacgag cgcacaccttt    3240 gagtggtggt tctacaacgt ctcgctcgag tacaggcctg gagaaccact gctctcacag    3300
ccaccggctg aagggtctgc tccatctgaa ggcggacaga ctccctcaga aggagccaca    3360
acgggcaccc tcgacgtaaa gctcgtgaac tcatggggta ccggtgcaca gtacgaggtc    3420
tcagtcaacc tggacaccctc aagcacctgg aagctcctaa ttaagatcaa ggacggcaag    3480
atctcagaca tatggggtgc cagcatcgtg gaacgcagg gagactacgt agtggtccag    3540
ccgagttccc caacggcatc ggctacagtc ggtttcgtga cctcaggaaa tgccccattg    3600
gtggaggagg cagttctgct ctctggtgac aaggtgctcg ccacgtggac tgcaccgacg    3660
gcctcggcct cggacctgaa cgtcactatt aagatcgaca gcgagtggga ctcaggattc    3720
gtggtcaaga tatacgtcac caacaacggc aacgcccccg tttcaagctg gcagataaag    3780
ctcagaatga cgagcctcat ctcgagcatc tggggtggca cgtacacagc cagcggggac    3840
gttgtaacta tagtcccgac tggaaacaac ccgtcataa acccagggga cactgtcgag    3900
atcggcttcg ttgccagcaa gcaggagcc tacgtgtacc ccgagctcat tggagtcgaa    3960
atcctttaa                                                            3969
```

<210> SEQ ID NO 2
<211> LENGTH: 1322
<212> TYPE: PRT
<213> ORGANISM: Unknown
<220> FEATURE:
<223> OTHER INFORMATION: Thermostable cellulase from thermophilic archaeon

<400> SEQUENCE: 2

```
Met Tyr Arg Gln Lys Ala Leu Ala Val Phe Val Leu Phe Val Val Leu
1               5                   10                  15

Ala Gly Val Ala Gly Ser Ile Pro Ala Gly Tyr Ala Ala Thr Asn Thr
            20                  25                  30
```

-continued

```
Ser Thr Tyr Thr Thr Pro Thr Gly Ile Tyr Tyr Glu Val Arg Gly Asp
        35                  40                  45
Thr Ile Tyr Met Ile Asn Val Ala Thr Gly Glu Glu Thr Pro Ile His
 50                  55                  60
Leu Phe Gly Val Asn Trp Phe Gly Phe Glu Thr Pro Asn Tyr Val Val
 65                  70                  75                  80
His Gly Leu Trp Ser Arg Asn Trp Glu Asp Met Leu Leu Gln Ile Lys
                 85                  90                  95
Ser Leu Gly Phe Asn Ala Ile Arg Leu Pro Phe Cys Thr Gln Ser Val
            100                 105                 110
Lys Pro Gly Thr Met Pro Thr Gly Ile Asp Tyr Ala Lys Asn Pro Asp
            115                 120                 125
Leu Gln Gly Leu Asp Ser Val Gln Ile Met Glu Lys Ile Ile Lys Lys
        130                 135                 140
Ala Gly Asp Leu Gly Ile Phe Val Leu Leu Asp Tyr His Arg Ile Gly
145                 150                 155                 160
Cys Asn Phe Ile Glu Pro Leu Trp Tyr Thr Asp Ser Phe Ser Glu Gln
                165                 170                 175
Asp Tyr Ile Asn Thr Trp Val Glu Val Ala Gln Arg Phe Gly Lys Tyr
            180                 185                 190
Trp Asn Val Ile Gly Ala Asp Leu Lys Asn Glu Pro His Ser Ser Ser
            195                 200                 205
Pro Ala Pro Ala Ala Tyr Thr Asp Gly Ser Gly Ala Thr Trp Gly Met
        210                 215                 220
Gly Asn Asn Ala Thr Asp Trp Asn Leu Ala Ala Glu Arg Ile Gly Lys
225                 230                 235                 240
Ala Ile Leu Glu Val Ala Pro His Trp Leu Ile Phe Val Glu Gly Thr
                245                 250                 255
Gln Phe Thr Thr Pro Glu Ile Asp Gly Ser Tyr Lys Trp Gly His Asn
            260                 265                 270
Ala Trp Trp Gly Gly Asn Leu Met Gly Val Arg Lys Tyr Pro Val Asn
            275                 280                 285
Leu Pro Arg Asn Lys Leu Val Tyr Ser Pro His Val Tyr Gly Pro Asp
        290                 295                 300
Val Tyr Asp Gln Pro Tyr Phe Asp Pro Ala Glu Gly Phe Pro Asp Asn
305                 310                 315                 320
Leu Pro Asp Ile Trp Tyr His His Phe Gly Tyr Val Lys Leu Asp Leu
                325                 330                 335
Gly Tyr Pro Val Val Ile Gly Glu Phe Gly Gly Lys Tyr Gly His Gly
            340                 345                 350
Gly Asp Pro Arg Asp Val Thr Trp Gln Asn Lys Ile Ile Asp Trp Met
            355                 360                 365
Ile Gln Asn Lys Phe Cys Asp Phe Phe Tyr Trp Ser Trp Asn Pro Asn
        370                 375                 380
Ser Gly Asp Thr Gly Gly Ile Leu Gln Asp Asp Trp Thr Thr Ile Trp
385                 390                 395                 400
Glu Asp Lys Tyr Asn Asn Leu Lys Arg Leu Met Asp Ser Cys Ser Gly
                405                 410                 415
Asn Ala Thr Ala Pro Ser Val Pro Thr Thr Thr Thr Thr Ser Thr
            420                 425                 430
Pro Pro Thr Thr Thr Thr Thr Thr Ser Thr Pro Thr Thr Thr
        435                 440                 445
Gln Thr Pro Thr Thr Thr Thr Thr Pro Thr Thr Thr Thr Thr Thr Thr
```

-continued

```
            450                 455                 460
Thr Pro Ser Asn Asn Val Pro Phe Glu Thr Val Asn Val Leu Pro Thr
465                 470                 475                 480

Ser Ser Gln Tyr Glu Gly Thr Ser Val Glu Val Val Cys Asp Gly Thr
                485                 490                 495

Gln Cys Ala Ser Ser Val Trp Gly Ala Pro Asn Leu Trp Gly Val Val
                500                 505                 510

Lys Ile Gly Asn Ala Thr Met Asp Pro Asn Val Trp Gly Trp Glu Asp
                515                 520                 525

Val Tyr Lys Thr Ala Pro Gln Asp Ile Gly Thr Gly Ser Thr Lys Met
        530                 535                 540

Glu Ile Arg Asn Gly Val Leu Lys Val Thr Asn Leu Trp Asn Ile Asn
545                 550                 555                 560

Met His Pro Lys Tyr Asn Thr Met Ala Tyr Pro Glu Val Ile Tyr Gly
                565                 570                 575

Ala Lys Pro Trp Gly Asn Gln Pro Ile Asn Ala Pro Asn Phe Val Leu
                580                 585                 590

Pro Ile Lys Val Ser Gln Leu Pro Arg Ile Leu Val Asp Thr Lys Tyr
                595                 600                 605

Thr Leu Glu Lys Ser Phe Pro Gly Asn Asn Phe Ala Phe Glu Ala Trp
        610                 615                 620

Leu Phe Lys Asp Ala Asn Asn Met Arg Ala Pro Gly Gln Gly Asp Tyr
625                 630                 635                 640

Glu Ile Met Val Gln Leu Tyr Ile Glu Gly Gly Tyr Pro Ala Gly Tyr
                645                 650                 655

Asp Lys Gly Pro Val Leu Thr Val Asp Val Pro Ile Ile Val Asp Gly
                660                 665                 670

Arg Leu Leu Asn Gln Thr Phe Glu Leu Tyr Asp Val Ile Ala Asp Ala
                675                 680                 685

Gly Trp Arg Phe Phe Thr Phe Lys Pro Thr Lys Asn Tyr Asn Gly Ser
        690                 695                 700

Glu Val Val Phe Asp Tyr Thr Lys Phe Ile Glu Ile Val Asp Asn Tyr
705                 710                 715                 720

Leu Gly Gly Gly Ser Leu Thr Asn His Tyr Leu Met Ser Leu Glu Phe
                725                 730                 735

Gly Thr Glu Ile Tyr Thr Asn Gly Cys Thr Ser Phe Pro Cys Thr Val
                740                 745                 750

Asp Val Arg Trp Thr Leu Asp Lys Tyr Arg Phe Ile Leu Ala Pro Gly
                755                 760                 765

Thr Met Ala Thr Glu Glu Ala Met Arg Val Leu Val Gly Glu Val Gln
        770                 775                 780

Pro Pro Ala Ser Thr Thr Ser Gln Thr Thr Ser Thr Thr Thr
785                 790                 795                 800

Pro Thr Pro Thr Thr Thr Thr Thr Gln Thr Ser Thr Thr Thr
                805                 810                 815

Thr Thr Ser Pro Pro Thr Thr Ala Pro Ala Gln Asp Val Ile Lys
                820                 825                 830

Leu Arg Tyr Pro Asp Asp Gly Gln Trp Pro Glu Ala Pro Ile Asp Arg
        835                 840                 845

Asp Gly Asp Gly Asn Pro Glu Phe Tyr Ile Glu Ile Asn Pro Trp Asn
850                 855                 860

Ile Leu Ser Ala Glu Gly Tyr Ala Glu Met Thr Tyr Asn Leu Ser Ser
865                 870                 875                 880
```

```
Gly Val Leu His Tyr Val Gln Ala Leu Asp Ser Ile Thr Leu Lys Asn
            885                 890                 895
Gly Gly Ala Trp Val His Gly Tyr Pro Glu Ile Phe Tyr Gly Asn Lys
        900                 905                 910
Pro Trp Asn Asn Asn Ser Ala Thr Asp Gly Glu Val Pro Leu Pro Gly
        915                 920                 925
Lys Val Ser Asn Leu Ser Asn Phe Tyr Leu Thr Val Ser Tyr Lys Leu
        930                 935                 940
Leu Pro Lys Asn Gly Leu Pro Ile Asn Leu Ala Ile Glu Ser Trp Leu
945                 950                 955                 960
Thr Arg Glu Pro Trp Arg Asn Ser Gly Ile Asn Ser Asp Glu Gln Glu
            965                 970                 975
Leu Met Ile Trp Leu Tyr Tyr Asp Gly Leu Gln Pro Ala Gly Ser Lys
            980                 985                 990
Val Lys Glu Ile Val Val Pro Ile Val Val Asn Gly Thr Pro Val Asn
            995                 1000                1005
Ala Thr Phe Glu Val Trp Lys Ala Asn Ile Gly Trp Glu Tyr Val
        1010                1015                1020
Ala Phe Arg Ile Lys Thr Pro Ile Lys Glu Gly Thr Val Thr Ile
        1025                1030                1035
Pro Tyr Gly Ala Phe Ile Ser Ala Ala Ala Asn Val Thr Ser Leu
        1040                1045                1050
Ala Asn Tyr Pro Glu Leu Tyr Leu Glu Asp Val Glu Val Gly Thr
        1055                1060                1065
Glu Tyr Gly Thr Pro Ser Thr Thr Ser Ala His Leu Glu Trp Trp
        1070                1075                1080
Phe Tyr Asn Val Ser Leu Glu Tyr Arg Pro Gly Glu Pro Leu Leu
        1085                1090                1095
Ser Gln Pro Pro Ala Glu Gly Ser Ala Pro Ser Glu Gly Gly Gln
        1100                1105                1110
Thr Pro Ser Glu Gly Ala Thr Thr Gly Thr Leu Asp Val Lys Leu
        1115                1120                1125
Val Asn Ser Trp Gly Thr Gly Ala Gln Tyr Glu Val Ser Val Asn
        1130                1135                1140
Leu Asp Thr Ser Ser Thr Trp Lys Leu Leu Ile Lys Ile Lys Asp
        1145                1150                1155
Gly Lys Ile Ser Asp Ile Trp Gly Ala Ser Ile Val Gly Thr Gln
        1160                1165                1170
Gly Asp Tyr Val Val Val Gln Pro Ser Ser Pro Thr Ala Ser Ala
        1175                1180                1185
Thr Val Gly Phe Val Thr Ser Gly Asn Ala Pro Leu Val Glu Glu
        1190                1195                1200
Ala Val Leu Leu Ser Gly Asp Lys Val Leu Ala Thr Trp Thr Ala
        1205                1210                1215
Pro Thr Ala Ser Ala Ser Asp Leu Asn Val Thr Ile Lys Ile Asp
        1220                1225                1230
Ser Glu Trp Asp Ser Gly Phe Val Val Lys Ile Tyr Val Thr Asn
        1235                1240                1245
Asn Gly Asn Ala Pro Val Ser Ser Trp Gln Ile Lys Leu Arg Met
        1250                1255                1260
Thr Ser Leu Ile Ser Ser Ile Trp Gly Gly Thr Tyr Thr Ala Ser
        1265                1270                1275
```

```
Gly Asp Val Val Thr Ile Val Pro Thr Gly Asn Asn Thr Val Ile
    1280                1285                1290

Asn Pro Gly Asp Thr Val Glu Ile Gly Phe Val Ala Ser Lys Gln
    1295                1300                1305

Gly Ala Tyr Val Tyr Pro Glu Leu Ile Gly Val Glu Ile Leu
    1310                1315                1320

<210> SEQ ID NO 3
<211> LENGTH: 3273
<212> TYPE: DNA
<213> ORGANISM: Unknown
<220> FEATURE:
<223> OTHER INFORMATION: Fragment of thermostable cellulase from
      thermophilic archaeon

<400> SEQUENCE: 3
ctggcggctg agaggatagg aaaggcaatc ctggaggttg ctccgcactg gcttatattc      60
gttgagggaa cacagtttac cacccccgag atagacggta gctacaagtg gggccacaac    120
gcctggtggg gcggaaacct catgggcgtt aggaagtacc cagtcaacct gcccaggaac    180
aagctcgtct acagccccca cgtttacggc ccagacgttt acgaccagcc ctactttgac    240
cccgcagagg gcttccccga caacttaccc gacatctggt accaccactt cggctacgta    300
aagcttgatc tcggttaccc tgttgttata ggtgagttcg gaggcaagta cggccatggg    360
ggagacccga gacgtcact tggcagaac aagataatag actggatgat ccagaacaaa     420
ttctgtgact tcttctactg gagctggaac ccaacagcg gtgacacagg tggaattctg     480
caggatgact ggacgacaat atgggaggac aaatacaaca acctgaagag gctcatggac    540
agctgctctg gaaacgccac tgctccgtcc gtccccacga caactacaac aaccagtaca    600
ccgccaacaa ccacaacgac tacaacatcc actccaacga ccactaccca gaccccgacc    660
accactactc caactacgac aaccaccacg actacaactc cttcaaataa cgtcccattt    720
gaaactgtga acgttctccc gactagctcc cagtacgagg gaaccagcgt ggaggttgta    780
tgtgatggaa cccagtgtgc ctccagcgtt tggggagctc cgaacctctg gggagtcgtt    840
aagatcggaa acgctacaat ggaccccaac gtttggggct gggaggacgt ttacaagact    900
gcaccccagg acattggaac cggcagcaca agatggagat aaggaacgg ggtgctcaag     960 gttacaaacc tctggaacat caacatgcat ccgaagtaca cacaatggc atacccggag    1020 gtcatatacg gcgccaagcc ttggggcaac cagccaataa acgctccgaa cttcgtgctc    1080
ccgataaagg tctcccagct tccgaggata tcgttgaca caaagtacac gctcgaaaag    1140
agcttcccag gaaacaactt cgcctttgag gcctggctct tcaaggatgc caacaacatg    1200
agggcaccag gccaggggga ctacgagata atggtacagc tctacatcga gggcggatat    1260
ccagcgggct acgacaaggg gccggttctc accgttgatg ttccaataat cgttgatgga    1320
aggcttttaa accagacttt tgagctctac gacgtcatag cggatgccgg atggaggttc    1380
ttcaccttca gccaactaa gaactacaac ggctcagagg ttgtgttcga ctacaccaaa    1440
ttcatagaaa tagttgacaa ctacctcggc ggtggcagcc tcacgaacca ctacctgatg    1500
tccctggaat tcgtaccga gatatacacc aacgggtgca cctcgttccc gtgcacagtg    1560
gacgtaaggt ggaccctga caagtacagg ttcatcctgg ccccaggaac aatggccact    1620
gaggaggcca tgagagttct cgtcggagag gtccagcctc ccgcttccac aacaacatcg    1680
cagacgacta cttcaaccac aaccccaacg cccactacca ctactacgac tcagacttca    1740
accaccacta caaccacctc accgccgaca accaccgcac ctgctcagga cgtaattaag    1800
```

```
ctcaggtacc cggacgatgg gcagtggccc gaggccccaa ttgacaggga tggagacgga   1860
aacccagagt tctacataga aataaacccg tggaacatac tgagcgctga aggctacgcc   1920
gagatgacct acaacttgag cagcggggtt ctccactacg tccaggccct ggatagtata   1980
accctcaaaa acggcggtgc ctgggtgcac ggatatcccg agatattcta cggcaacaag   2040
ccctggaaca caactcagc caccgatgga gaagttccac tgcctggaaa agtctcgaac    2100
ctgagcaact tctacctgac cgtgagctac aagctgctgc cgaagaacgg acttccaata   2160
aaccttgcaa tcgagtcatg gctcacaagg gagccctgga ggaacagcgg aataaacagc   2220
gacgagcagg agctcatgat atggctgtac tacgacggac tccagccggc cggctcgaag   2280
gtcaaggaaa tcgttgtccc gatagtggtg aacggcactc cagtgaacgc taccttcgag   2340
gtctggaagg cgaacatcgg ctgggagtac gtagccttca gaataaagac cccaataaag   2400
gagggaaccg ttaccatacc gtacggagct tcataagcg ccgccgcgaa cgtaacgagc     2460
ctagccaact accccgagct gtacctggaa gacgttgagg ttggaaccga atacggaacg   2520
ccctcaacca cgagcgcaca ccttgagtgg tggttctaca acgtctcgct cgagtacagg   2580
cctggagaac cactgctctc acagccaccg gctgaagggt ctgctccatc tgaaggcgga   2640
cagactccct cagaaggagc cacaacgggc accctcgacg taaagctcgt gaactcatgg   2700
ggtaccggtg cacagtacga ggtctcagtc aacctggaca cctcaagcac ctggaagctc   2760
ctaattaaga tcaaggacgg caagatctca gacatatggg gtgccagcat cgtgggaacg   2820
cagggagact acgtagtggt ccagccgagt tccccaacgg catcggctac agtcggtttc   2880
gtgacctcag gaaatgcccc attggtggag gaggcagttc tgctctctgg tgacaaggtg   2940
ctcgccacgt ggactgcacc gacggcctcg gcctcggacc tgaacgtcac tattaagatc   3000
gacagcgagt gggactcagg attcgtggtc aagatatacg tcaccaacaa cggcaacgcc   3060
cccgtttcaa gctggcagat aaagctcaga atgacgagcc tcatctcgag catctggggt   3120
ggcacgtaca cagccagcgg ggacgttgta actatagtcc cgactggaaa caacaccgtc   3180
ataaacccag gggacactgt cgagatcggc ttcgttgcca gcaagcaggg agcctacgtg   3240
taccccgagc tcattggagt cgaaatcctt taa                                3273
```

<210> SEQ ID NO 4
<211> LENGTH: 1090
<212> TYPE: PRT
<213> ORGANISM: Unknown
<220> FEATURE:
<223> OTHER INFORMATION: Fragment of thermostable cellulase from
      thermophilic archaeon

<400> SEQUENCE: 4

Leu Ala Ala Glu Arg Ile Gly Lys Ala Ile Leu Glu Val Ala Pro His
1               5                   10                  15

Trp Leu Ile Phe Val Glu Gly Thr Gln Phe Thr Thr Pro Glu Ile Asp
            20                  25                  30

Gly Ser Tyr Lys Trp Gly His Asn Ala Trp Trp Gly Gly Asn Leu Met
        35                  40                  45

Gly Val Arg Lys Tyr Pro Val Asn Leu Pro Arg Asn Lys Leu Val Tyr
    50                  55                  60

Ser Pro His Val Tyr Gly Pro Asp Val Tyr Asp Gln Pro Tyr Phe Asp
65                  70                  75                  80

Pro Ala Glu Gly Phe Pro Asp Asn Leu Pro Asp Ile Trp Tyr His His
                85                  90                  95

```
Phe Gly Tyr Val Lys Leu Asp Leu Gly Tyr Pro Val Ile Gly Glu
            100                 105                 110

Phe Gly Gly Lys Tyr Gly His Gly Gly Asp Pro Arg Asp Val Thr Trp
            115                 120                 125

Gln Asn Lys Ile Ile Asp Trp Met Ile Gln Asn Lys Phe Cys Asp Phe
130                 135                 140

Phe Tyr Trp Ser Trp Asn Pro Asn Ser Gly Asp Thr Gly Gly Ile Leu
145                 150                 155                 160

Gln Asp Asp Trp Thr Thr Ile Trp Glu Asp Lys Tyr Asn Asn Leu Lys
            165                 170                 175

Arg Leu Met Asp Ser Cys Ser Gly Asn Ala Thr Ala Pro Ser Val Pro
            180                 185                 190

Thr Thr Thr Thr Thr Thr Ser Thr Pro Pro Thr Thr Thr Thr Thr Thr
            195                 200                 205

Thr Ser Thr Pro Thr Thr Thr Thr Gln Thr Pro Thr Thr Thr Thr Pro
    210                 215                 220

Thr Thr Thr Thr Thr Thr Thr Thr Pro Ser Asn Asn Val Pro Phe
225                 230                 235                 240

Glu Thr Val Asn Val Leu Pro Thr Ser Ser Gln Tyr Glu Gly Thr Ser
                245                 250                 255

Val Glu Val Val Cys Asp Gly Thr Gln Cys Ala Ser Ser Val Trp Gly
                260                 265                 270

Ala Pro Asn Leu Trp Gly Val Val Lys Ile Gly Asn Ala Thr Met Asp
            275                 280                 285

Pro Asn Val Trp Gly Trp Glu Asp Val Tyr Lys Thr Ala Pro Gln Asp
290                 295                 300

Ile Gly Thr Gly Ser Thr Lys Met Glu Ile Arg Asn Gly Val Leu Lys
305                 310                 315                 320

Val Thr Asn Leu Trp Asn Ile Asn Met His Pro Lys Tyr Asn Thr Met
            325                 330                 335

Ala Tyr Pro Glu Val Ile Tyr Gly Ala Lys Pro Trp Gly Asn Gln Pro
            340                 345                 350

Ile Asn Ala Pro Asn Phe Val Leu Pro Ile Lys Val Ser Gln Leu Pro
            355                 360                 365

Arg Ile Leu Val Asp Thr Lys Tyr Thr Leu Glu Lys Ser Phe Pro Gly
370                 375                 380

Asn Asn Phe Ala Phe Glu Ala Trp Leu Phe Lys Asp Ala Asn Asn Met
385                 390                 395                 400

Arg Ala Pro Gly Gln Gly Asp Tyr Glu Ile Met Val Gln Leu Tyr Ile
            405                 410                 415

Glu Gly Gly Tyr Pro Ala Gly Tyr Asp Lys Gly Pro Val Leu Thr Val
            420                 425                 430

Asp Val Pro Ile Ile Val Asp Gly Arg Leu Leu Asn Gln Thr Phe Glu
            435                 440                 445

Leu Tyr Asp Val Ile Ala Asp Ala Gly Trp Arg Phe Phe Thr Phe Lys
            450                 455                 460

Pro Thr Lys Asn Tyr Asn Gly Ser Glu Val Val Phe Asp Tyr Thr Lys
465                 470                 475                 480

Phe Ile Glu Ile Val Asp Asn Tyr Leu Gly Gly Ser Leu Thr Asn
            485                 490                 495

His Tyr Leu Met Ser Leu Glu Phe Gly Thr Glu Ile Tyr Thr Asn Gly
            500                 505                 510
```

-continued

Cys Thr Ser Phe Pro Cys Thr Val Asp Val Arg Trp Thr Leu Asp Lys
            515                 520                 525

Tyr Arg Phe Ile Leu Ala Pro Gly Thr Met Ala Thr Glu Glu Ala Met
    530                 535                 540

Arg Val Leu Val Gly Glu Val Gln Pro Pro Ala Ser Thr Thr Thr Ser
545                 550                 555                 560

Gln Thr Thr Thr Ser Thr Thr Thr Pro Thr Pro Thr Thr Thr Thr Thr
                565                 570                 575

Thr Gln Thr Ser Thr Thr Thr Thr Thr Ser Pro Pro Thr Thr Thr Thr
            580                 585                 590

Ala Pro Ala Gln Asp Val Ile Lys Leu Arg Tyr Pro Asp Asp Gly Gln
        595                 600                 605

Trp Pro Glu Ala Pro Ile Asp Arg Asp Gly Asp Gly Asn Pro Glu Phe
    610                 615                 620

Tyr Ile Glu Ile Asn Pro Trp Asn Ile Leu Ser Ala Glu Gly Tyr Ala
625                 630                 635                 640

Glu Met Thr Tyr Asn Leu Ser Ser Gly Val Leu His Tyr Val Gln Ala
                645                 650                 655

Leu Asp Ser Ile Thr Leu Lys Asn Gly Gly Ala Trp Val His Gly Tyr
            660                 665                 670

Pro Glu Ile Phe Tyr Gly Asn Lys Pro Trp Asn Asn Asn Ser Ala Thr
        675                 680                 685

Asp Gly Glu Val Pro Leu Pro Gly Lys Val Ser Asn Leu Ser Asn Phe
    690                 695                 700

Tyr Leu Thr Val Ser Tyr Lys Leu Leu Pro Lys Asn Gly Leu Pro Ile
705                 710                 715                 720

Asn Leu Ala Ile Glu Ser Trp Leu Thr Arg Glu Pro Trp Arg Asn Ser
                725                 730                 735

Gly Ile Asn Ser Asp Glu Gln Glu Leu Met Ile Trp Leu Tyr Tyr Asp
            740                 745                 750

Gly Leu Gln Pro Ala Gly Ser Lys Val Lys Glu Ile Val Val Pro Ile
        755                 760                 765

Val Val Asn Gly Thr Pro Val Asn Ala Thr Phe Glu Val Trp Lys Ala
    770                 775                 780

Asn Ile Gly Trp Glu Tyr Val Ala Phe Arg Ile Lys Thr Pro Ile Lys
785                 790                 795                 800

Glu Gly Thr Val Thr Ile Pro Tyr Gly Ala Phe Ile Ser Ala Ala Ala
                805                 810                 815

Asn Val Thr Ser Leu Ala Asn Tyr Pro Glu Leu Tyr Leu Glu Asp Val
            820                 825                 830

Glu Val Gly Thr Glu Tyr Gly Thr Pro Ser Thr Thr Ser Ala His Leu
        835                 840                 845

Glu Trp Trp Phe Tyr Asn Val Ser Leu Glu Tyr Arg Pro Gly Glu Pro
    850                 855                 860

Leu Leu Ser Gln Pro Pro Ala Glu Gly Ser Ala Pro Ser Glu Gly Gly
865                 870                 875                 880

Gln Thr Pro Ser Glu Gly Ala Thr Thr Gly Thr Leu Asp Val Lys Leu
                885                 890                 895

Val Asn Ser Trp Gly Thr Gly Ala Gln Tyr Glu Val Ser Val Asn Leu
            900                 905                 910

Asp Thr Ser Ser Thr Trp Lys Leu Leu Ile Lys Ile Lys Asp Gly Lys
        915                 920                 925

Ile Ser Asp Ile Trp Gly Ala Ser Ile Val Gly Thr Gln Gly Asp Tyr

Val Val Val Gln Pro Ser Ser Pro Thr Ala Ser Ala Thr Val Gly Phe
945                 950                 955                 960

Val Thr Ser Gly Asn Ala Pro Leu Val Glu Glu Ala Val Leu Leu Ser
            965                 970                 975

Gly Asp Lys Val Leu Ala Thr Trp Thr Ala Pro Thr Ala Ser Ala Ser
        980                 985                 990

Asp Leu Asn Val Thr Ile Lys Ile Asp Ser Glu Trp Asp Ser Gly Phe
        995                 1000                1005

Val Val Lys Ile Tyr Val Thr Asn Asn Gly Asn Ala Pro Val Ser
    1010                1015                1020

Ser Trp Gln Ile Lys Leu Arg Met Thr Ser Leu Ile Ser Ser Ile
    1025                1030                1035

Trp Gly Gly Thr Tyr Thr Ala Ser Gly Asp Val Val Thr Ile Val
    1040                1045                1050

Pro Thr Gly Asn Asn Thr Val Ile Asn Pro Gly Asp Thr Val Glu
    1055                1060                1065

Ile Gly Phe Val Ala Ser Lys Gln Gly Ala Tyr Val Tyr Pro Glu
    1070                1075                1080

Leu Ile Gly Val Glu Ile Leu
    1085                1090

<210> SEQ ID NO 5
<211> LENGTH: 3132
<212> TYPE: DNA
<213> ORGANISM: Unknown
<220> FEATURE:
<223> OTHER INFORMATION: Fragment of thermostable cellulase from
      thermophilic archaeon

<400> SEQUENCE: 5
atgggcgtta ggaagtaccc agtcaacctg cccaggaaca agctcgtcta cagcccccac      60
gtttacggcc cagacgttta cgaccagccc tactttgacc ccgcagaggg cttccccgac     120
aacttacccg acatctggta ccaccacttc ggctacgtaa agcttgatct cggttaccct     180
gttgttatag gtgagttcgg aggcaagtac ggccatgggg gagacccgag agacgtcact     240
tggcagaaca agataataga ctggatgatc cagaacaaat tctgtgactt cttctactgg     300
agctggaacc ccaacagcgg tgacacaggt ggaattctgc aggatgactg gacgacaata     360
tgggaggaca aatacaacaa cctgaagagg ctcatggaca gctgctctgg aaacgccact     420
gctccgtccg tccccacgac aactacaaca accagtacac cgccaacaac cacaacgact     480
acaacatcca ctccaacgac cactacccag accccgacca ccactactcc aactacgaca     540
accaccacga ctacaactcc ttcaaataac gtcccatttg aaactgtgaa cgttctcccg     600
actagctccc agtacgaggg aaccagcgtg gaggttgtat gtgatggaac ccagtgtgcc     660
tccagcgttt ggggagctcc gaacctctgg ggagtcgtta agatcggaaa cgctacaatg     720
gaccccaacg tttggggctg ggaggacgtt tacaagactg caccccagga cattggaacc     780
ggcagcacaa agatggagat aaggaacggg gtgctcaagg ttacaaacct ctggaacatc     840
aacatgcatc cgaagtacaa cacaatggca tacccggagg tcatatacgg cgccaagcct     900
tggggcaacc agccaataaa cgctccgaac ttcgtgctcc cgataaaggt ctcccagctt     960
ccgaggatac tcgttgacac aaagtacacg ctcgaaaaga gcttcccagg aaacaacttc    1020
gcctttgagg cctggctctt caaggatgcc aacaacatga gggcaccagg ccaggggac     1080

```
tacgagataa tggtacagct ctacatcgag gcggatatc cagcgggcta cgacaagggg    1140
ccggttctca ccgttgatgt tccaataatc gttgatggaa ggcttttaaa ccagactttt    1200
gagctctacg acgtcatagc ggatgccgga tggaggttct tcaccttcaa gccaactaag    1260
aactacaacg gctcagaggt tgtgttcgac tacaccaaat tcatagaaat agttgacaac    1320
tacctcggcg gtggcagcct cacgaaccac tacctgatgt ccctggaatt cggtaccgag    1380
atatacacca acgggtgcac ctcgttcccg tgcacagtgg acgtaaggtg gacccttgac    1440
aagtacaggt tcatcctggc cccaggaaca atggccactg aggaggccat gagagttctc    1500
gtcggagagg tccagcctcc cgcttccaca acaacatcgc agacgactac ttcaaccaca    1560
accccaacgc ccactaccac tactacgact cagacttcaa ccaccactac aaccacctca    1620
ccgccgacaa ccaccgcacc tgctcaggac gtaattaagc tcaggtaccc ggacgatggg    1680
cagtggcccg aggccccaat tgacagggat ggagacggaa acccagagtt ctacatagaa    1740
ataaacccgt ggaacatact gagcgctgaa ggctacgccg agatgaccta caacttgagc    1800
agcggggttc tccactacgt ccaggccctg gatagtataa ccctcaaaaa cggcggtgcc    1860
tgggtgcacg gatatcccga gatattctac ggcaacaagc cctggaacaa caactcagcc    1920
accgatggag aagttccact gcctggaaaa gtctcgaacc tgagcaactt ctacctgacc    1980
gtgagctaca agctgctgcc gaagaacgga cttccaataa accttgcaat cgagtcatgg    2040
ctcacaaggg agccctggag gaacagcgga ataaacagcg acgagcagga gctcatgata    2100
tggctgtact acgacggact ccagccggcc ggctcgaagg tcaaggaaat cgttgtcccg    2160
atagtggtga acggcactcc agtgaacgct accttcgagg tctggaaggc gaacatcggc    2220
tgggagtacg tagccttcag aataaagacc ccaataaagg agggaaccgt taccataccg    2280
tacgagcttt tcataagcgc cgccgcgaac gtaacgagcc tagccaacta ccccgagctg    2340
tacctggaag acgttgaggt tggaaccgaa tacggaacgc cctcaaccac gagcgcacac    2400
cttgagtggt ggttctacaa cgtctcgctc gagtacaggc ctggagaacc actgctctca    2460
cagccaccgg ctgaagggtc tgctccatct gaaggcggac agactccctc agaaggagcc    2520
acaacgggca ccctcgacgt aaagctcgtg aactcatggg gtaccggtgc acagtacgag    2580
gtctcagtca acctggacac ctcaagcacc tggaagctcc taattaagat caaggacggc    2640
aagatctcag acatatgggg tgccagcatc gtgggaacgc agggagacta cgtagtggtc    2700
cagccgagtt ccccaacggc atcggctaca gtcggtttcg tgacctcagg aaatgcccca    2760
ttggtggagg aggcagttct gctctctggt gacaaggtgc tcgccacgtg gactgcaccg    2820
acggcctcgg cctcggacct gaacgtcact attaagatcg acagcgagtg ggactcagga    2880
ttcgtggtca agatatacgt caccaacaac ggcaacgccc ccgtttcaag ctggcagata    2940
aagctcagaa tgacgagcct catctcgagc atctggggtg gcacgtacac agccagcggg    3000
gacgttgtaa ctatagtccc gactggaaac aacaccgtca taaacccagg ggacactgtc    3060
gagatcggct tcgttgccag caagcaggga gcctacgtgt accccgagct cattggagtc    3120
gaaatccttt aa                                                        3132
```

<210> SEQ ID NO 6  
<211> LENGTH: 1043  
<212> TYPE: PRT  
<213> ORGANISM: Unknown  
<220> FEATURE:  
<223> OTHER INFORMATION: Fragment of thermostable cellulase from thermophilic archaeon

```
<400> SEQUENCE: 6

Met Gly Val Arg Lys Tyr Pro Val Asn Leu Pro Arg Asn Lys Leu Val
1               5                   10                  15

Tyr Ser Pro His Val Tyr Gly Pro Asp Val Tyr Asp Gln Pro Tyr Phe
            20                  25                  30

Asp Pro Ala Glu Gly Phe Pro Asp Asn Leu Pro Asp Ile Trp Tyr His
        35                  40                  45

His Phe Gly Tyr Val Lys Leu Asp Leu Gly Tyr Pro Val Val Ile Gly
    50                  55                  60

Glu Phe Gly Gly Lys Tyr Gly His Gly Gly Asp Pro Arg Asp Val Thr
65                  70                  75                  80

Trp Gln Asn Lys Ile Ile Asp Trp Met Ile Gln Asn Lys Phe Cys Asp
                85                  90                  95

Phe Phe Tyr Trp Ser Trp Asn Pro Asn Ser Gly Asp Thr Gly Gly Ile
            100                 105                 110

Leu Gln Asp Asp Trp Thr Thr Ile Trp Glu Asp Lys Tyr Asn Asn Leu
        115                 120                 125

Lys Arg Leu Met Asp Ser Cys Ser Gly Asn Ala Thr Ala Pro Ser Val
    130                 135                 140

Pro Thr Thr Thr Thr Thr Thr Ser Thr Pro Pro Thr Thr Thr Thr Thr
145                 150                 155                 160

Thr Thr Ser Thr Pro Thr Thr Thr Thr Gln Thr Pro Thr Thr Thr Thr
            165                 170                 175

Pro Thr Thr Thr Thr Thr Thr Thr Thr Pro Ser Asn Asn Val Pro
        180                 185                 190

Phe Glu Thr Val Asn Val Leu Pro Thr Ser Ser Gln Tyr Glu Gly Thr
            195                 200                 205

Ser Val Glu Val Val Cys Asp Gly Thr Gln Cys Ala Ser Ser Val Trp
210                 215                 220

Gly Ala Pro Asn Leu Trp Gly Val Val Lys Ile Gly Asn Ala Thr Met
225                 230                 235                 240

Asp Pro Asn Val Trp Gly Trp Glu Asp Val Tyr Lys Thr Ala Pro Gln
            245                 250                 255

Asp Ile Gly Thr Gly Ser Thr Lys Met Glu Ile Arg Asn Gly Val Leu
        260                 265                 270

Lys Val Thr Asn Leu Trp Asn Ile Asn Met His Pro Lys Tyr Asn Thr
    275                 280                 285

Met Ala Tyr Pro Glu Val Ile Tyr Gly Ala Lys Pro Trp Gly Asn Gln
290                 295                 300

Pro Ile Asn Ala Pro Asn Phe Val Leu Pro Ile Lys Val Ser Gln Leu
305                 310                 315                 320

Pro Arg Ile Leu Val Asp Thr Lys Tyr Thr Leu Glu Lys Ser Phe Pro
            325                 330                 335

Gly Asn Asn Phe Ala Phe Glu Ala Trp Leu Phe Lys Asp Ala Asn Asn
            340                 345                 350

Met Arg Ala Pro Gly Gln Gly Asp Tyr Glu Ile Met Val Gln Leu Tyr
    355                 360                 365

Ile Glu Gly Gly Tyr Pro Ala Gly Tyr Asp Lys Gly Pro Val Leu Thr
    370                 375                 380

Val Asp Val Pro Ile Ile Val Asp Gly Arg Leu Leu Asn Gln Thr Phe
385                 390                 395                 400

Glu Leu Tyr Asp Val Ile Ala Asp Ala Gly Trp Arg Phe Phe Thr Phe
            405                 410                 415
```

```
Lys Pro Thr Lys Asn Tyr Asn Gly Ser Glu Val Val Phe Asp Tyr Thr
                420                 425                 430

Lys Phe Ile Glu Ile Val Asp Asn Tyr Leu Gly Gly Ser Leu Thr
            435                 440                 445

Asn His Tyr Leu Met Ser Leu Glu Phe Gly Thr Glu Ile Tyr Thr Asn
        450                 455                 460

Gly Cys Thr Ser Phe Pro Cys Thr Val Asp Val Arg Trp Thr Leu Asp
465                 470                 475                 480

Lys Tyr Arg Phe Ile Leu Ala Pro Gly Thr Met Ala Thr Glu Glu Ala
                485                 490                 495

Met Arg Val Leu Val Gly Glu Val Gln Pro Ala Ser Thr Thr Thr
            500                 505                 510

Ser Gln Thr Thr Thr Ser Thr Thr Thr Pro Thr Pro Thr Thr Thr Thr
        515                 520                 525

Thr Thr Gln Thr Ser Thr Thr Thr Thr Thr Ser Pro Pro Thr Thr
            530                 535                 540

Thr Ala Pro Ala Gln Asp Val Ile Lys Leu Arg Tyr Pro Asp Asp Gly
545                 550                 555                 560

Gln Trp Pro Glu Ala Pro Ile Asp Arg Asp Gly Asp Gly Asn Pro Glu
                565                 570                 575

Phe Tyr Ile Glu Ile Asn Pro Trp Asn Ile Leu Ser Ala Glu Gly Tyr
            580                 585                 590

Ala Glu Met Thr Tyr Asn Leu Ser Ser Gly Val Leu His Tyr Val Gln
        595                 600                 605

Ala Leu Asp Ser Ile Thr Leu Lys Asn Gly Gly Ala Trp Val His Gly
            610                 615                 620

Tyr Pro Glu Ile Phe Tyr Gly Asn Lys Pro Trp Asn Asn Ser Ala
625                 630                 635                 640

Thr Asp Gly Glu Val Pro Leu Pro Gly Lys Val Ser Asn Leu Ser Asn
                645                 650                 655

Phe Tyr Leu Thr Val Ser Tyr Lys Leu Leu Pro Lys Asn Gly Leu Pro
            660                 665                 670

Ile Asn Leu Ala Ile Glu Ser Trp Leu Thr Arg Glu Pro Trp Arg Asn
        675                 680                 685

Ser Gly Ile Asn Ser Asp Glu Gln Glu Leu Met Ile Trp Leu Tyr Tyr
    690                 695                 700

Asp Gly Leu Gln Pro Ala Gly Ser Lys Val Lys Glu Ile Val Val Pro
705                 710                 715                 720

Ile Val Val Asn Gly Thr Pro Val Asn Ala Thr Phe Glu Val Trp Lys
                725                 730                 735

Ala Asn Ile Gly Trp Glu Tyr Val Ala Phe Arg Ile Lys Thr Pro Ile
            740                 745                 750

Lys Glu Gly Thr Val Thr Ile Pro Tyr Gly Ala Phe Ile Ser Ala Ala
        755                 760                 765

Ala Asn Val Thr Ser Leu Ala Asn Tyr Pro Glu Leu Tyr Leu Glu Asp
            770                 775                 780

Val Glu Val Gly Thr Glu Tyr Gly Thr Pro Ser Thr Thr Ser Ala His
785                 790                 795                 800

Leu Glu Trp Trp Phe Tyr Asn Val Ser Leu Glu Tyr Arg Pro Gly Glu
                805                 810                 815

Pro Leu Leu Ser Gln Pro Pro Ala Glu Gly Ser Ala Pro Ser Glu Gly
            820                 825                 830
```

```
Gly Gln Thr Pro Ser Glu Gly Ala Thr Thr Gly Thr Leu Asp Val Lys
            835                 840                 845

Leu Val Asn Ser Trp Gly Thr Gly Ala Gln Tyr Glu Val Ser Val Asn
        850                 855                 860

Leu Asp Thr Ser Thr Trp Lys Leu Leu Ile Lys Ile Lys Asp Gly
865                 870                 875                 880

Lys Ile Ser Asp Ile Trp Gly Ala Ser Ile Gly Thr Gln Gly Asp
                885                 890                 895

Tyr Val Val Gln Pro Ser Ser Pro Thr Ala Ser Ala Thr Val Gly
            900                 905                 910

Phe Val Thr Ser Gly Asn Ala Pro Leu Val Glu Glu Ala Val Leu Leu
        915                 920                 925

Ser Gly Asp Lys Val Leu Ala Thr Trp Thr Ala Pro Thr Ala Ser Ala
    930                 935                 940

Ser Asp Leu Asn Val Thr Ile Lys Ile Asp Ser Glu Trp Asp Ser Gly
945                 950                 955                 960

Phe Val Val Lys Ile Tyr Val Thr Asn Asn Gly Asn Ala Pro Val Ser
                965                 970                 975

Ser Trp Gln Ile Lys Leu Arg Met Thr Ser Leu Ile Ser Ser Ile Trp
            980                 985                 990

Gly Gly Thr Tyr Thr Ala Ser Gly Asp Val Val Thr Ile Val Pro Thr
        995                 1000                1005

Gly Asn  Asn Thr Val Ile Asn  Pro Gly Asp Thr Val  Glu Ile Gly
       1010                1015                1020

Phe Val  Ala Ser Lys Gln Gly  Ala Tyr Val Tyr Pro  Glu Leu Ile
       1025                1030                1035

Gly Val  Glu Ile Leu
    1040

<210> SEQ ID NO 7
<211> LENGTH: 1509
<212> TYPE: DNA
<213> ORGANISM: Unknown
<220> FEATURE:
<223> OTHER INFORMATION: Thermostable cellulase from thermophilic
      archaeon

<400> SEQUENCE: 7
atgagggccc tcaaaaagtt ctttccgatt tcatcggtc ttttgttcct tctctcgccg      60
gttagtgccg tcgaatacag ggctgagaac gggaagatat acgccgatgg gaacgaaatc    120
cacctatacg gcgtttcatg gtttggcttc gagctcaaag atcacgttgt ctttggttta    180
acgcagagaa actggaagga gatccttcag gacgttaaga ggctcggatt caacgcggta    240
aggcttccct ctgcagtga gtcaataaag cccggcacaa acccaacct gaacaaaata      300 aactacgagc tcaaccctga tctaaagaac ctcacctccc tagagataat ggagaagata    360
atcgcctatg ccaacgaact cgggatatac gttctgctcg actaccaccg tatagggtgc    420
gcctacatag aacccctctg gtacacggat gagtatcctg aggagcagta catagccgac    480
tgggtctttc ttgcggagag gtttgggcgc tatccgaacg tcatagggc ggacataaag     540 aacgagcccc acgacgaggc ctcatggggc actgggacg agactgactt caggctcttc     600
gcggagaggg tcgggaaggc gatactggaa aaggctcccc actggctgat attcgtcgag    660
ggagttcaat acacccactt gtccgagata gactctaaaa accccctccc ctgcttctgg    720
ggagagaacc tcatgggagt cagagaatac cccgtaaggc ttcccgaggg caaagtggtc    780
```

```
tattcgcccc acgtttacgg tccaagcgtc tatgagatgc cctacttcag cgatccaagc    840
tttcccgata acctgctcga gatatgggag ctccacttcg gctatctgaa ggacctcaac    900
tacacactcg tcataggcga atggggcggc aactacgagg gaaaggataa ggtctggcag    960
gacaagttct cggagtggct ggtagaaaag gggattcacg acttcttcta ctggtgcctg   1020
aacccagaga gcggagatac gaagggggtt ttcctcgacg actggaagac tgtgaactgg   1080
gagaagatga gggtaatcta ccgcgtcata aaggcatcga atccagagtt tgaggagccg   1140
ctttacataa tcctcaaggc caacacaacc tcgcgggtgc tcgataaagg ggagcgaata   1200
aagctctact ggtacacgag cggcgaggtg gtggacagca acttcgcgga tttaagcgag   1260
ggagaaatag agatcgagct gaaccagagc acaaccttt  acattgccgc aaggaagggt   1320
ggagaagtta aaaacgagtc catcaggttc tcggtcatag agcccaacac tccttcgagg   1380
gaggagactg aaactcccac agtgccagag accacaccaa aaagcgggga acactcatca   1440
acatcatggc tcttttttggc gcttctcctg ctggccgctg tggccgttct ggccaaactc   1500
aggcgctga                                                            1509
```

<210> SEQ ID NO 8
<211> LENGTH: 502
<212> TYPE: PRT
<213> ORGANISM: Unknown
<220> FEATURE:
<223> OTHER INFORMATION: Thermostable cellulase from thermophilic
      archaeon

<400> SEQUENCE: 8

```
Met Arg Ala Leu Lys Lys Phe Phe Pro Ile Phe Ile Gly Leu Leu Phe
1               5                   10                  15

Leu Leu Ser Pro Val Ser Ala Val Glu Tyr Arg Ala Glu Asn Gly Lys
            20                  25                  30

Ile Tyr Ala Asp Gly Asn Glu Ile His Leu Tyr Gly Val Ser Trp Phe
        35                  40                  45

Gly Phe Glu Leu Lys Asp His Val Val Phe Gly Leu Thr Gln Arg Asn
    50                  55                  60

Trp Lys Glu Ile Leu Gln Asp Val Lys Arg Leu Gly Phe Asn Ala Val
65                  70                  75                  80

Arg Leu Pro Phe Cys Ser Glu Ser Ile Lys Pro Gly Thr Lys Pro Asn
                85                  90                  95

Leu Asn Lys Ile Asn Tyr Glu Leu Asn Pro Asp Leu Lys Asn Leu Thr
            100                 105                 110

Ser Leu Glu Ile Met Glu Lys Ile Ala Tyr Ala Asn Glu Leu Gly
        115                 120                 125

Ile Tyr Val Leu Leu Asp Tyr His Arg Ile Gly Cys Ala Tyr Ile Glu
    130                 135                 140

Pro Leu Trp Tyr Thr Asp Glu Tyr Pro Glu Glu Gln Tyr Ile Ala Asp
145                 150                 155                 160

Trp Val Phe Leu Ala Glu Arg Phe Gly Arg Tyr Pro Asn Val Ile Gly
                165                 170                 175

Ala Asp Ile Lys Asn Glu Pro His Asp Glu Ala Ser Trp Gly Thr Gly
            180                 185                 190

Asp Glu Thr Asp Phe Arg Leu Phe Ala Glu Arg Val Gly Lys Ala Ile
        195                 200                 205

Leu Glu Lys Ala Pro His Trp Leu Ile Phe Val Glu Gly Val Gln Tyr
    210                 215                 220
```

Thr His Leu Ser Glu Ile Asp Ser Lys Asn Pro Tyr Pro Cys Phe Trp
225                 230                 235                 240

Gly Glu Asn Leu Met Gly Val Arg Glu Tyr Pro Val Arg Leu Pro Glu
            245                 250                 255

Gly Lys Val Val Tyr Ser Pro His Val Tyr Gly Pro Ser Val Tyr Glu
        260                 265                 270

Met Pro Tyr Phe Ser Asp Pro Ser Phe Pro Asp Asn Leu Leu Glu Ile
    275                 280                 285

Trp Glu Leu His Phe Gly Tyr Leu Lys Asp Leu Asn Tyr Thr Leu Val
290                 295                 300

Ile Gly Glu Trp Gly Asn Tyr Glu Gly Lys Asp Lys Val Trp Gln
305                 310                 315                 320

Asp Lys Phe Ser Glu Trp Leu Val Glu Lys Gly Ile His Asp Phe Phe
                325                 330                 335

Tyr Trp Cys Leu Asn Pro Glu Ser Gly Asp Thr Lys Gly Val Phe Leu
            340                 345                 350

Asp Asp Trp Lys Thr Val Asn Trp Glu Lys Met Arg Val Ile Tyr Arg
        355                 360                 365

Val Ile Lys Ala Ser Asn Pro Glu Phe Glu Pro Leu Tyr Ile Ile
370                 375                 380

Leu Lys Ala Asn Thr Thr Ser Arg Val Leu Asp Lys Gly Glu Arg Ile
385                 390                 395                 400

Lys Leu Tyr Trp Tyr Thr Ser Gly Glu Val Val Asp Ser Asn Phe Ala
                405                 410                 415

Asp Leu Ser Glu Gly Glu Ile Glu Ile Glu Leu Asn Gln Ser Thr Thr
            420                 425                 430

Phe Tyr Ile Ala Ala Arg Lys Gly Gly Glu Val Lys Asn Glu Ser Ile
        435                 440                 445

Arg Phe Ser Val Ile Glu Pro Asn Thr Pro Ser Arg Glu Glu Thr Glu
    450                 455                 460

Thr Pro Thr Val Pro Glu Thr Thr Pro Lys Ser Gly Glu His Ser Ser
465                 470                 475                 480

Thr Ser Trp Leu Phe Leu Ala Leu Leu Leu Ala Ala Val Ala Val
                485                 490                 495

Leu Ala Lys Leu Arg Arg
            500

<210> SEQ ID NO 9
<211> LENGTH: 1572
<212> TYPE: DNA
<213> ORGANISM: Unknown
<220> FEATURE:
<223> OTHER INFORMATION: Thermostable cellulase from thermophilic
      archaeon

<400> SEQUENCE: 9
atggcaacca ccgcttgggg ggcgggcgac cgccccccct cagaattttg ggaggttcgt      60
gttatgaggg ccctcaaaaa gttctttccg attttcatcg gtcttttgtt ccttctctcg     120
ccggttagtg ccgtcgaata cagggctgag aacgggaaga tatacgccga tgggaacgaa     180
atccacctat acggcgtttc atggtttggc ttcgagctca agatcacgt tgtctttggt      240 ttaacgcaga gaaactggaa ggagatcctt caggacgtta gaggctcgg attcaacgcg      300 gtaaggcttc cctcctgcag tgagtcaata aagcccggca caaaaccaa cctgaacaaa      360 ataaactacg agctcaaccc tgatctaaag aacctcacct ccctagagat aatggagaag     420

|   |   |
|---|---|
| ataatcgcct atgccaacga actcgggata tacgttctgc tcgactacca ccgtataggg | 480 |
| tgcgcctaca tagaaccoct ctggtacacg gatgagtatc ctgaggagca gtacatagcc | 540 |
| gactgggtct ttcttgcgga gaggtttggg cgctatccga acgtcatagg ggcggacata | 600 |
| aagaacgagc cccacgacga ggcctcatgg ggcactgggg acgagactga cttcaggctc | 660 |
| ttcgcggaga gggtcgggaa ggcgatactg gaaaaggctc cccactggct gatattcgtc | 720 |
| gagggagttc aatacaccca cttgtccgag atagactcta aaaacccta cccctgcttc | 780 |
| tggggagaga acctcatggg agtcagagaa taccccgtaa ggcttcccga gggcaaagtg | 840 |
| gtctattcgc cccacgttta cggtccaagc gtctatgaga tgccctactt cagcgatcca | 900 |
| agctttcccg ataacctgct cgagatatgg gagctccact tcggctatct gaaggacctc | 960 |
| aactacacac tcgtcatagg cgaatggggc ggcaactacg agggaaagga taaggtctgg | 1020 |
| caggacaagt tctcggagtg gctggtagaa aaggggattc acgacttctt ctactggtgc | 1080 |
| ctgaacccag agagcggaga tacgaagggg gttttcctcg acgactggaa gactgtgaac | 1140 |
| tgggagaaga tgagggtaat ctaccgcgtc ataaaggcat cgaatccaga gtttgaggag | 1200 |
| ccgctttaca taatcctcaa ggccaacaca acctcgcggg tgctcgataa aggggagcga | 1260 |
| ataaagctct actggtacac gagcggcgag gtggtggaca gcaacttcgc ggatttaagc | 1320 |
| gagggagaaa tagagatcga gctgaaccag agcacaacct tttacattgc cgcaaggaag | 1380 |
| ggtggagaag ttaaaaacga gtccatcagg ttctcggtca tagagcccaa cactccttcg | 1440 |
| ggggaggaga ctgaaactcc cacagtgcca gagaccacac caaaaagcgg ggaacactca | 1500 |
| tcaacatcat ggctcttttt ggcgcttctc ctgctggccg ctgtggccgt tctggccaaa | 1560 |
| ctcaggcgct ga | 1572 |

<210> SEQ ID NO 10
<211> LENGTH: 523
<212> TYPE: PRT
<213> ORGANISM: Unknown
<220> FEATURE:
<223> OTHER INFORMATION: Thermostable cellulase from thermophilic archaeon

<400> SEQUENCE: 10

Met Ala Thr Thr Ala Trp Gly Ala Gly Asp Arg Pro Pro Ser Glu Phe
1               5                   10                  15

Trp Glu Val Arg Val Met Arg Ala Leu Lys Lys Phe Phe Pro Ile Phe
                20                  25                  30

Ile Gly Leu Leu Phe Leu Leu Ser Pro Val Ser Ala Val Glu Tyr Arg
            35                  40                  45

Ala Glu Asn Gly Lys Ile Tyr Ala Asp Gly Asn Glu Ile His Leu Tyr
        50                  55                  60

Gly Val Ser Trp Phe Gly Phe Glu Leu Lys Asp His Val Val Phe Gly
65                  70                  75                  80

Leu Thr Gln Arg Asn Trp Lys Glu Ile Leu Gln Asp Val Lys Arg Leu
                85                  90                  95

Gly Phe Asn Ala Val Arg Leu Pro Phe Cys Ser Glu Ser Ile Lys Pro
            100                 105                 110

Gly Thr Lys Pro Asn Leu Asn Lys Ile Asn Tyr Glu Leu Asn Pro Asp
        115                 120                 125

Leu Lys Asn Leu Thr Ser Leu Glu Ile Met Glu Lys Ile Ile Ala Tyr
    130                 135                 140

Ala Asn Glu Leu Gly Ile Tyr Val Leu Leu Asp Tyr His Arg Ile Gly

```
            145                 150                 155                 160
        Cys Ala Tyr Ile Glu Pro Leu Trp Tyr Thr Asp Glu Tyr Pro Glu Glu
                            165                 170                 175

Gln Tyr Ile Ala Asp Trp Val Phe Leu Ala Glu Arg Phe Gly Arg Tyr
                        180                 185                 190

Pro Asn Val Ile Gly Ala Asp Ile Lys Asn Glu Pro His Asp Glu Ala
                        195                 200                 205

Ser Trp Gly Thr Gly Asp Glu Thr Asp Phe Arg Leu Phe Ala Glu Arg
                210                 215                 220

Val Gly Lys Ala Ile Leu Glu Lys Ala Pro His Trp Leu Ile Phe Val
        225                 230                 235                 240

Glu Gly Val Gln Tyr Thr His Leu Ser Glu Ile Asp Ser Lys Asn Pro
                        245                 250                 255

Tyr Pro Cys Phe Trp Gly Glu Asn Leu Met Gly Val Arg Glu Tyr Pro
                        260                 265                 270

Val Arg Leu Pro Glu Gly Lys Val Val Tyr Ser Pro His Val Tyr Gly
                    275                 280                 285

Pro Ser Val Tyr Glu Met Pro Tyr Phe Ser Asp Pro Ser Phe Pro Asp
                    290                 295                 300

Asn Leu Leu Glu Ile Trp Glu Leu His Phe Gly Tyr Leu Lys Asp Leu
        305                 310                 315                 320

Asn Tyr Thr Leu Val Ile Gly Glu Trp Gly Gly Asn Tyr Glu Gly Lys
                            325                 330                 335

Asp Lys Val Trp Gln Asp Lys Phe Ser Glu Trp Leu Val Glu Lys Gly
                        340                 345                 350

Ile His Asp Phe Phe Tyr Trp Cys Leu Asn Pro Glu Ser Gly Asp Thr
                        355                 360                 365

Lys Gly Val Phe Leu Asp Asp Trp Lys Thr Val Asn Trp Glu Lys Met
                    370                 375                 380

Arg Val Ile Tyr Arg Val Ile Lys Ala Ser Asn Pro Glu Phe Glu Glu
        385                 390                 395                 400

Pro Leu Tyr Ile Ile Leu Lys Ala Asn Thr Thr Ser Arg Val Leu Asp
                        405                 410                 415

Lys Gly Glu Arg Ile Lys Leu Tyr Trp Tyr Thr Ser Gly Glu Val Val
                        420                 425                 430

Asp Ser Asn Phe Ala Asp Leu Ser Glu Gly Glu Ile Glu Ile Glu Leu
                    435                 440                 445

Asn Gln Ser Thr Thr Phe Tyr Ile Ala Ala Arg Lys Gly Gly Glu Val
                    450                 455                 460

Lys Asn Glu Ser Ile Arg Phe Ser Val Ile Glu Pro Asn Thr Pro Ser
        465                 470                 475                 480

Gly Glu Glu Thr Glu Thr Pro Thr Val Pro Glu Thr Thr Pro Lys Ser
                        485                 490                 495

Gly Glu His Ser Ser Thr Ser Trp Leu Phe Leu Ala Leu Leu Leu Leu
                    500                 505                 510

Ala Ala Val Ala Val Leu Ala Lys Leu Arg Arg
                    515                 520

<210> SEQ ID NO 11
<211> LENGTH: 1626
<212> TYPE: DNA
<213> ORGANISM: Unknown
<220> FEATURE:
<223> OTHER INFORMATION: Thermostable cellulase from thermophilic
      archaeon
```

<400> SEQUENCE: 11

```
atgctaccgg gcagggcagg gatgacgtca cggttaccgc cgcagccgct ggccatggca      60
accaccgctt gggggggcggg cgaccgcccc ccctcagaat tttgggaggt tcgtgttatg     120
agggccctca aaaagttctt tccgattttc atcggtcttt tgttccttct ctcgccggtt     180
agtgccgtcg aatacagggc tgagaacggg aagatatacg ccgatgggaa cgaaatccac     240
ctatacggcg tttcatggtt tggcttcgag ctcaaagatc acgttgtctt tggtttaacg     300
cagagaaact ggaaggagat ccttcaggac gttaagaggc tcggattcaa cgcggtaagg     360
cttcccttct gcagtgagtc aataaagccc ggcacaaaac ccaacctgaa caaaataaac     420
tacgagctca accctgatct aaagaacctc acctccctag ataatggaa gaagataatc      480
gcctatgcca cgaactcgg gatatacgtt ctgctcgact accaccgtat agggtgcgcc      540
tacatagaac ccctctggta cacggatgag tatcctgagg agcagtacat agccgactgg     600
gtctttcttg cggagaggtt tgggcgctat ccgaacgtca taggggcgga cataaagaac     660
gagccccacg acgaggcctc atggggcact ggggacgaga ctgacttcag gctcttcgcg     720
gagagggtcg ggaaggcgat actggaaaag gctccccact ggctgatatt cgtcgaggga     780
gttcaataca cccacttgtc cgagatagac tctaaaaacc cctaccctg cttctgggga      840
gagaacctca tgggagtcag agaataccc gtaaggcttc ccgagggcaa agtggtctat      900
tcgccccacg tttacggtcc aagcgtctat gagatgccct acttcagcga tccaagctt      960
cccgataacc tgctcgagat atgggagctc cacttcggct atctgaagga cctcaactac    1020
acactcgtca taggcgaatg gggcggcaac tacgagggaa aggataaggt ctggcaggac    1080
aagttctcgg agtggctggt agaaaagggg attcacgact tcttctactg gtgcctgaac    1140
ccagagagcg gagatacgaa ggggggtttc ctcgacgact ggaagactgt gaactgggag    1200
aagatgaggg taatctaccg cgccataaag gcatcgaatc cagagtttga ggagccgctt    1260
tacataatcc tcaaggccaa cacaacctcg cgggtgctcg ataaaggggga gcgaataaag    1320
ctctactggt acacgagcgg cgaggtggtg acagcaact cgcggatttt aagcgaggga     1380
gaaatagaga tcgagctgaa ccagagcaca accttttaca ttgccgcaag gaagggtgga    1440
gaagttaaaa acgagtccat caggttctcg gtcatagagc ccaacactcc ttcgggggag    1500
gagactgaaa ctcccacagt gccagagacc acaccaaaaa gcggggaaca ctcatcaaca    1560
tcatggctct ttttggcgct ctcctgctg gccgctgtgg ccgttctggc caaactcagg    1620
cgctga                                                               1626
```

<210> SEQ ID NO 12
<211> LENGTH: 541
<212> TYPE: PRT
<213> ORGANISM: Unknown
<220> FEATURE:
<223> OTHER INFORMATION: Thermostable cellulase from thermophilic archaeon

<400> SEQUENCE: 12

```
Met Leu Pro Gly Arg Ala Gly Met Thr Ser Arg Leu Pro Pro Gln Pro
1               5                   10                  15

Leu Ala Met Ala Thr Thr Ala Trp Gly Ala Gly Asp Arg Pro Pro Ser
            20                  25                  30

Glu Phe Trp Glu Val Arg Val Met Arg Ala Leu Lys Lys Phe Phe Pro
        35                  40                  45
```

```
Ile Phe Ile Gly Leu Leu Phe Leu Leu Ser Pro Val Ser Ala Val Glu
 50                  55                  60

Tyr Arg Ala Glu Asn Gly Lys Ile Tyr Ala Asp Gly Asn Glu Ile His
 65                  70                  75                  80

Leu Tyr Gly Val Ser Trp Phe Gly Phe Glu Leu Lys Asp His Val Val
                 85                  90                  95

Phe Gly Leu Thr Gln Arg Asn Trp Lys Glu Ile Leu Gln Asp Val Lys
            100                 105                 110

Arg Leu Gly Phe Asn Ala Val Arg Leu Pro Phe Cys Ser Glu Ser Ile
            115                 120                 125

Lys Pro Gly Thr Lys Pro Asn Leu Asn Lys Ile Asn Tyr Glu Leu Asn
130                 135                 140

Pro Asp Leu Lys Asn Leu Thr Ser Leu Glu Ile Met Glu Lys Ile Ile
145                 150                 155                 160

Ala Tyr Ala Asn Glu Leu Gly Ile Tyr Val Leu Leu Asp Tyr His Arg
                165                 170                 175

Ile Gly Cys Ala Tyr Ile Glu Pro Leu Trp Tyr Thr Asp Glu Tyr Pro
            180                 185                 190

Glu Glu Gln Tyr Ile Ala Asp Trp Val Phe Leu Ala Glu Arg Phe Gly
            195                 200                 205

Arg Tyr Pro Asn Val Ile Gly Ala Asp Ile Lys Asn Glu Pro His Asp
210                 215                 220

Glu Ala Ser Trp Gly Thr Gly Asp Glu Thr Asp Phe Arg Leu Phe Ala
225                 230                 235                 240

Glu Arg Val Gly Lys Ala Ile Leu Glu Lys Ala Pro His Trp Leu Ile
                245                 250                 255

Phe Val Glu Gly Val Gln Tyr Thr His Leu Ser Glu Ile Asp Ser Lys
            260                 265                 270

Asn Pro Tyr Pro Cys Phe Trp Gly Glu Asn Leu Met Gly Val Arg Glu
            275                 280                 285

Tyr Pro Val Arg Leu Pro Glu Gly Lys Val Val Tyr Ser Pro His Val
290                 295                 300

Tyr Gly Pro Ser Val Tyr Glu Met Pro Tyr Phe Ser Asp Pro Ser Phe
305                 310                 315                 320

Pro Asp Asn Leu Leu Glu Ile Trp Glu Leu His Phe Gly Tyr Leu Lys
                325                 330                 335

Asp Leu Asn Tyr Thr Leu Val Ile Gly Glu Trp Gly Gly Asn Tyr Glu
            340                 345                 350

Gly Lys Asp Lys Val Trp Gln Asp Lys Phe Ser Glu Trp Leu Val Glu
            355                 360                 365

Lys Gly Ile His Asp Phe Phe Tyr Trp Cys Leu Asn Pro Glu Ser Gly
370                 375                 380

Asp Thr Lys Gly Val Phe Leu Asp Asp Trp Lys Thr Val Asn Trp Glu
385                 390                 395                 400

Lys Met Arg Val Ile Tyr Arg Ala Ile Lys Ala Ser Asn Pro Glu Phe
                405                 410                 415

Glu Glu Pro Leu Tyr Ile Ile Leu Lys Ala Asn Thr Thr Ser Arg Val
            420                 425                 430

Leu Asp Lys Gly Glu Arg Ile Lys Leu Tyr Trp Tyr Thr Ser Gly Glu
            435                 440                 445

Val Val Asp Ser Asn Phe Ala Asp Leu Ser Glu Gly Glu Ile Glu Ile
450                 455                 460

Glu Leu Asn Gln Ser Thr Thr Phe Tyr Ile Ala Ala Arg Lys Gly Gly
```

```
                                        465                 470                 475                 480
Glu Val Lys Asn Glu Ser Ile Arg Phe Ser Val Ile Glu Pro Asn Thr
                    485                 490                 495

Pro Ser Gly Glu Glu Thr Glu Thr Pro Thr Val Pro Glu Thr Thr Pro
                500                 505                 510

Lys Ser Gly Glu His Ser Ser Thr Ser Trp Leu Phe Leu Ala Leu Leu
                515                 520                 525

Leu Leu Ala Ala Val Ala Val Leu Ala Lys Leu Arg Arg
        530                 535                 540

<210> SEQ ID NO 13
<211> LENGTH: 621
<212> TYPE: DNA
<213> ORGANISM: Unknown
<220> FEATURE:
<223> OTHER INFORMATION: Fragment of thermostable cellulase from
      thermophilic archaeon

<400> SEQUENCE: 13
ctgagcgctg aaggctacgc cgagatgacc tacaacttga gcagcggggt tctccactac     60
gtccaggccc tggatagtat aaccctcaaa aacggcggtg cctgggtgca cggatatccc    120
gagatattct acggcaacaa gccctggaac aacaactcag ccaccgatgg agaagttcca    180
ctgcctggaa agtctcgaa cctgagcaac ttctacctga ccgtgagcta caagctgctg    240
ccgaagaacg gacttccaat aaaccttgca atcgagtcat ggctcacaag ggagccctgg    300
aggaacagcg gaataaacag cgacgagcag gagctcatga tatggctgta ctacgacgga    360
ctccagccgg ccggctcgaa ggtcaaggaa atcgttgtcc cgatagtggt gaacggcact    420
ccagtgaacg ctaccttcga ggtctggaag gcgaacatcg gctgggagta cgtagccttc    480
agaataaaga ccccaataaa ggagggaacc gttaccatac cgtacggagc tttcataagc    540
gccgccgcga acgtaacgag cctagccaac taccccgagc tgtacctgga agacgttgag    600
gttggaaccg aatacggaac g                                               621

<210> SEQ ID NO 14
<211> LENGTH: 207
<212> TYPE: PRT
<213> ORGANISM: Unknown
<220> FEATURE:
<223> OTHER INFORMATION: Fragment of thermostable cellulase from
      thermophilic archaeon

<400> SEQUENCE: 14

Leu Ser Ala Glu Gly Tyr Ala Glu Met Thr Tyr Asn Leu Ser Ser Gly
1               5                   10                  15

Val Leu His Tyr Val Gln Ala Leu Asp Ser Ile Thr Leu Lys Asn Gly
            20                  25                  30

Gly Ala Trp Val His Gly Tyr Pro Glu Ile Phe Tyr Gly Asn Lys Pro
        35                  40                  45

Trp Asn Asn Ser Ala Thr Asp Gly Glu Val Pro Leu Pro Gly Lys
    50                  55                  60

Val Ser Asn Leu Ser Asn Phe Tyr Leu Thr Val Ser Tyr Lys Leu Leu
65                  70                  75                  80

Pro Lys Asn Gly Leu Pro Ile Asn Leu Ala Ile Glu Ser Trp Leu Thr
                85                  90                  95

Arg Glu Pro Trp Arg Asn Ser Gly Ile Asn Ser Asp Glu Gln Glu Leu
            100                 105                 110
```

Met Ile Trp Leu Tyr Tyr Asp Gly Leu Gln Pro Ala Gly Ser Lys Val
            115                 120                 125

Lys Glu Ile Val Val Pro Ile Val Val Asn Gly Thr Pro Val Asn Ala
130                 135                 140

Thr Phe Glu Val Trp Lys Ala Asn Ile Gly Trp Glu Tyr Val Ala Phe
145                 150                 155                 160

Arg Ile Lys Thr Pro Ile Lys Glu Gly Thr Val Thr Ile Pro Tyr Gly
                165                 170                 175

Ala Phe Ile Ser Ala Ala Ala Asn Val Thr Ser Leu Ala Asn Tyr Pro
            180                 185                 190

Glu Leu Tyr Leu Glu Asp Val Glu Val Gly Thr Glu Tyr Gly Thr
        195                 200                 205

<210> SEQ ID NO 15
<211> LENGTH: 960
<212> TYPE: DNA
<213> ORGANISM: Unknown
<220> FEATURE:
<223> OTHER INFORMATION: Fragment of thermostable cellulase from
      thermophilic archaeon

<400> SEQUENCE: 15

```
tttggagtca actggttcgg ctttgagaca ccgaactacg tcgttcacgg cctatggagt     60
aggaactggg aggacatgct cctccagatc aagagccttg gcttcaatgc gataaggctt    120
cccttctgta cccagtcagt aaaaccgggg acgatgccaa cggggattga ctacgccaag    180
aaccccgacc tccagggtct tgacagcgtc cagataatgg agaaaataat caagaaggct    240
ggagacctgg gcatattcgt gctcctcgac taccacagaa taggatgcaa cttcatagag    300
cccctatggt acaccgacag cttctcggag caggactaca taaacacctg ggttgaagtc    360
gcccagaggt tcggcaagta ctggaacgtt atcggcgcgg acctgaagaa cgaacccccac   420
agctcaagcc cgcacctgc tgcctacact gacggaagtg gggccacatg gggaatgggc    480
aacaacgcca ccgactggaa cctggcggct gagaggatag aaaggcaat cctggaggtt    540
gctccgcact ggcttatatt cgttgaggga acacagtta ccacccccga gatagacgt    600
agctacaagt ggggccacaa cgcctggtgg ggcggaaacc tcatgggcgt taggaagtac    660
ccagtcaacc tgcccaggaa caagctcgtc tacagcccc acgtttacgg cccagacgtt    720
tacgaccagc cctactttga ccccgcagag ggcttccccg acaacttacc cgacatctgg    780
taccaccact tcggctacgt aaagcttgat ctcggttacc ctgttgttat aggtgagttc    840
ggaggcaagt acggccatgg gggagacccg agagacgtca cttggcagaa caagataata    900
gactggatga tccagaacaa attctgtgac ttcttctact ggagctggaa ccccaacagc    960
```

<210> SEQ ID NO 16
<211> LENGTH: 320
<212> TYPE: PRT
<213> ORGANISM: Unknown
<220> FEATURE:
<223> OTHER INFORMATION: Fragment of thermostable cellulase from
      thermophilic archaeon

<400> SEQUENCE: 16

Phe Gly Val Asn Trp Phe Gly Phe Glu Thr Pro Asn Tyr Val Val His
1               5                   10                  15

Gly Leu Trp Ser Arg Asn Trp Glu Asp Met Leu Leu Gln Ile Lys Ser
            20                  25                  30

Leu Gly Phe Asn Ala Ile Arg Leu Pro Phe Cys Thr Gln Ser Val Lys

```
            35                  40                  45
Pro Gly Thr Met Pro Thr Gly Ile Asp Tyr Ala Lys Asn Pro Asp Leu
 50                  55                  60

Gln Gly Leu Asp Ser Val Gln Ile Met Glu Lys Ile Ile Lys Lys Ala
 65                  70                  75                  80

Gly Asp Leu Gly Ile Phe Val Leu Leu Asp Tyr His Arg Ile Gly Cys
                 85                  90                  95

Asn Phe Ile Glu Pro Leu Trp Tyr Thr Asp Ser Phe Ser Glu Gln Asp
             100                 105                 110

Tyr Ile Asn Thr Trp Val Glu Val Ala Gln Arg Phe Gly Lys Tyr Trp
         115                 120                 125

Asn Val Ile Gly Ala Asp Leu Lys Asn Glu Pro His Ser Ser Ser Pro
 130                 135                 140

Ala Pro Ala Ala Tyr Thr Asp Gly Ser Gly Ala Thr Trp Gly Met Gly
145                 150                 155                 160

Asn Asn Ala Thr Asp Trp Asn Leu Ala Ala Glu Arg Ile Gly Lys Ala
                165                 170                 175

Ile Leu Glu Val Ala Pro His Trp Leu Ile Phe Val Glu Gly Thr Gln
            180                 185                 190

Phe Thr Thr Pro Glu Ile Asp Gly Ser Tyr Lys Trp Gly His Asn Ala
        195                 200                 205

Trp Trp Gly Gly Asn Leu Met Gly Val Arg Lys Tyr Pro Val Asn Leu
210                 215                 220

Pro Arg Asn Lys Leu Val Tyr Ser Pro His Val Tyr Gly Pro Asp Val
225                 230                 235                 240

Tyr Asp Gln Pro Tyr Phe Asp Pro Ala Glu Gly Phe Pro Asp Asn Leu
                245                 250                 255

Pro Asp Ile Trp Tyr His His Phe Gly Tyr Val Lys Leu Asp Leu Gly
            260                 265                 270

Tyr Pro Val Val Ile Gly Glu Phe Gly Gly Lys Tyr Gly His Gly Gly
        275                 280                 285

Asp Pro Arg Asp Val Thr Trp Gln Asn Lys Ile Ile Asp Trp Met Ile
290                 295                 300

Gln Asn Lys Phe Cys Asp Phe Phe Tyr Trp Ser Trp Asn Pro Asn Ser
305                 310                 315                 320

<210> SEQ ID NO 17
<211> LENGTH: 477
<212> TYPE: DNA
<213> ORGANISM: Unknown
<220> FEATURE:
<223> OTHER INFORMATION: Fragment of thermostable cellulase from
      thermophilic archaeon

<400> SEQUENCE: 17
ccgaacttcg tgctcccgat aaaggtctcc cagcttccga ggatactcgt tgacacaaag      60
tacacgctcg aaaagagctt cccaggaaac aacttcgcct tgaggcctg gctcttcaag     120 gatgccaaca acatgagggc accaggccag ggggactacg agataatggt acagctctac     180
atcgagggcg atatccagc gggctacgac aaggggccgg ttctcaccgt tgatgttcca     240
ataatcgttg atggaaggct tttaaaccag acttttgagc tctacgacgt catagcggat     300
gccggatgga ggttcttcac cttcaagcca actaagaact acaacggctc agaggttgtg     360
ttcgactaca ccaaattcat agaaatagtt gacaactacc tcggcggtgg cagcctcacg     420
aaccactacc tgatgtccct ggaattcggt accgagatat acaccaacgg gtgcacc        477
```

<210> SEQ ID NO 18
<211> LENGTH: 159
<212> TYPE: PRT
<213> ORGANISM: Unknown
<220> FEATURE:
<223> OTHER INFORMATION: Fragment of thermostable cellulase from
      thermophilic archaeon

<400> SEQUENCE: 18

```
Pro Asn Phe Val Leu Pro Ile Lys Val Ser Gln Leu Pro Arg Ile Leu
1               5                   10                  15

Val Asp Thr Lys Tyr Thr Leu Glu Lys Ser Phe Pro Gly Asn Asn Phe
            20                  25                  30

Ala Phe Glu Ala Trp Leu Phe Lys Asp Ala Asn Asn Met Arg Ala Pro
        35                  40                  45

Gly Gln Gly Asp Tyr Glu Ile Met Val Gln Leu Tyr Ile Glu Gly Gly
    50                  55                  60

Tyr Pro Ala Gly Tyr Asp Lys Gly Pro Val Leu Thr Val Asp Val Pro
65                  70                  75                  80

Ile Ile Val Asp Gly Arg Leu Leu Asn Gln Thr Phe Glu Leu Tyr Asp
                85                  90                  95

Val Ile Ala Asp Ala Gly Trp Arg Phe Phe Thr Phe Lys Pro Thr Lys
            100                 105                 110

Asn Tyr Asn Gly Ser Glu Val Val Phe Asp Tyr Thr Lys Phe Ile Glu
        115                 120                 125

Ile Val Asp Asn Tyr Leu Gly Gly Ser Leu Thr Asn His Tyr Leu
    130                 135                 140

Met Ser Leu Glu Phe Gly Thr Glu Ile Tyr Thr Asn Gly Cys Thr
145                 150                 155
```

<210> SEQ ID NO 19
<211> LENGTH: 474
<212> TYPE: DNA
<213> ORGANISM: Unknown
<220> FEATURE:
<223> OTHER INFORMATION: Fragment of thermostable cellulase from
      thermophilic archaeon

<400> SEQUENCE: 19

```
ccactgcctg gaaaagtctc gaacctgagc aacttctacc tgaccgtgag ctacaagctg      60
ctgccgaaga acggacttcc aataaacctt gcaatcgagt catggctcac aagggagccc     120
tggaggaaca gcggaataaa cagcgacgag caggagctca tgatatggct gtactacgac     180
ggactccagc cggccggctc gaaggtcaag gaaatcgttg tcccgatagt ggtgaacggc     240
actccagtga acgctacctt cgaggtctgg aaggcgaaca tcggctggga gtacgtagcc     300
ttcagaataa agaccccaat aaaggaggga accgttacca taccgtacgg agctttcata     360
agcgccgccg cgaacgtaac gagcctagcc aactaccccg agctgtacct ggaagacgtt     420
gaggttggaa ccgaatacgg aacgccctca accacgagcg cacaccttga gtgg           474
```

<210> SEQ ID NO 20
<211> LENGTH: 158
<212> TYPE: PRT
<213> ORGANISM: Unknown
<220> FEATURE:
<223> OTHER INFORMATION: Fragment of thermostable cellulase from
      thermophilic archaeon

<400> SEQUENCE: 20

```
Pro Leu Pro Gly Lys Val Ser Asn Leu Ser Asn Phe Tyr Leu Thr Val
1               5                   10                  15

Ser Tyr Lys Leu Leu Pro Lys Asn Gly Leu Pro Ile Asn Leu Ala Ile
            20                  25                  30

Glu Ser Trp Leu Thr Arg Glu Pro Trp Arg Asn Ser Gly Ile Asn Ser
            35                  40                  45

Asp Glu Gln Glu Leu Met Ile Trp Leu Tyr Tyr Asp Gly Leu Gln Pro
            50                  55                  60

Ala Gly Ser Lys Val Lys Glu Ile Val Val Pro Ile Val Val Asn Gly
65              70                  75                  80

Thr Pro Val Asn Ala Thr Phe Glu Val Trp Lys Ala Asn Ile Gly Trp
                85                  90                  95

Glu Tyr Val Ala Phe Arg Ile Lys Thr Pro Ile Lys Glu Gly Thr Val
                100                 105                 110

Thr Ile Pro Tyr Gly Ala Phe Ile Ser Ala Ala Ala Asn Val Thr Ser
            115                 120                 125

Leu Ala Asn Tyr Pro Glu Leu Tyr Leu Glu Asp Val Glu Val Gly Thr
        130                 135                 140

Glu Tyr Gly Thr Pro Ser Thr Thr Ser Ala His Leu Glu Trp
145             150                 155
```

<210> SEQ ID NO 21
<211> LENGTH: 3969
<212> TYPE: DNA
<213> ORGANISM: Artificial Sequence
<220> FEATURE:
<223> OTHER INFORMATION: Sequence encoding SEQ ID NO. 2 codon-optimised
      for E. coli expression

<400> SEQUENCE: 21

```
atgtatcgtc aaaaggcgct ggcggtgttc gttctgttcg tggttctggc gggtgttgcg      60
ggtagcattc cggcgggtta cgcggcgacc aacaccagca cctataccac cccgaccggc     120
atctactatg aggttcgtgg tgacaccatc tacatgatta cgtggcgac cggcgaggaa      180 accccgattc acctgttcgg cgttaactgg ttcggttttg agaccccgaa ctacgtggtt     240
cacggcctgt ggagccgtaa ctgggaagac atgctgctgc aaatcaaaag cctgggtttc     300
aacgcgattc gtctgccgtt ttgcacccaa agcgtgaagc cgggcaccat gccgaccggt     360
atcgattatg cgaaaaaccc ggacctgcaa ggcctggaca gcgttcaaat catggagaag     420
atcattaaga aagcgggcga tctgggtatt ttcgtgctgc tggactacca ccgtatcggt     480
tgcaacttca ttgaaccgct gtggtatacc gatagcttta gcgagcagga ctacatcaac     540
acctgggttg aagtggcgca acgttttggc aagtattgga acgttattgg tcgcgacctg     600
aaaaacgaac gcacagcag cagcccggcg ccggctgcgt acaccgatgg cagcggtgcg     660
acctggggta tgggtaacaa cgcgaccgat tggaacctgg cggcggagcg tatcggcaaa     720
gcgattctgg aagttgcgcc gcactggctg atcttcgtgg agggcacccca gtttaccacc     780 ccggaaattg atggcagcta aagtggggt cacaacgcgt ggtggggtgg caacctgatg     840
ggtgttcgta gtacccggt gaacctgccg cgtaacaaac tggtttacag cccgcacgtg     900
tatggtccgg atgtttacga ccaaccgtat ttcgacccgg cggagggctt ccggataaac     960
ctgccggaca tctggtatca ccacttcggt tatgttaagc tggatctggg ctatccggtg    1020
gttattggtg aatttggtgg caaatacggt cacggtggcg atccgcgtga cgtgacctgg    1080
cagaacaaga tcattgactg gatgatccaa aacaagttct gcgatttctt ttattggagc    1140
```

```
tggaacccga acagcggtga caccggtggt atcctgcaag acgattggac caccatttgg   1200
gaggacaagt acaacaacct gaaacgtctg atggatagct gtagcggtaa cgcgaccgcg   1260
ccgagcgttc cgacgaccac gaccaccacc agcaccccgc cgactactac tactactact   1320
accagcaccc cgaccaccac cacccaaacc ccgactacta ctaccccgac tactacaact   1380
actaccacca ccaccccgag caacaacgtg ccgttcgaaa ccgttaacgt gctgccgacc   1440
agcagccagt acgagggcac cagcgttgaa gtggtttgcg atggcaccca atgcgcgagc   1500
agcgtgtggg gcgcgccgaa cctgtggggc gtggttaaaa tcggtaacgc gacgatggac   1560
ccgaacgtgt ggggctggga ggacgtttac aagaccgcgc cgcaggatat cggcaccggt   1620
agcaccaaga tggaaattcg taacggtgtt ctgaaagtga ccaacctgtg gaacattaac   1680
atgcacccga agtacaacac gatggcgtat ccggaagtga tctacggcgc gaaaccgtgg   1740
ggtaaccagc cgattaacgc gccgaacttc gtgctgccga tcaaagttag ccaactgccg   1800
cgtattctgg tggacaccaa gtacaccctg gagaagagct tcccgggtaa caacttcgcg   1860
tttgaagcgt ggctgtttaa agatgcgaac aacatgcgtg cgccgggtca gggtgattat   1920
gagatcatgt gcaactgta cattgaaggt ggctacccgg cgggctatga taagggtccg   1980
gttctgaccg ttgatgtgcc gatcattgtg gacggtcgtc tgctgaacca gaccttcgaa   2040
ctgtacgatg ttatcgcgga cgcgggctgg cgtttcttta cctttaagcc gaccaaaaac   2100
tataacggta gcgaggtggt tttcgactac accaagttca tcgaaatcgt ggataactac   2160
ctgggtggcg gtagcctgac caaccactac ctgatgagcc tggagttcgg caccgaaatc   2220
tataccaacg gttgcaccag cttccgtgc accgttgatg tgcgttggac cctggacaag   2280
taccgtttca ttctggcgcc gggtacgatg gcgaccgagg aagcgatgcg tgttctggtg   2340
ggcgaggttc agccgccggc gagcaccacc accagccaga ccaccaccag caccaccacc   2400
ccgaccccga ctactacaac aaccaccagc accagcacca ctactaccac caccagcccg   2460
ccgaccacca ccgcgccggc gcaggatgtg atcaagctgc gttatccgga cgatggtcaa   2520
tggccggaag cgccgattga ccgtgatggc gacggtaacc cggagtttta catcgaaatt   2580
aacccgtgga acatcctgag cgcggagggt tatgcggaaa tgacctacaa cctgagcagc   2640
ggcgttctgc actacgtgca agcgctggac agcatcaccc tgaagaacgg cggtgcgtgg   2700
gttcacgggt atccggagat tttctacggt aacaaaccgt ggaacaacaa cagcgcgacc   2760
gatggcgaag tgccgctgcc gggcaaagtt agcaacctga gcaactttta tctgaccgtg   2820
agctacaagc tgctgccgaa aaacggcctg ccgatcaacc tggcgattga gagctggctg   2880
acccgtgaac cgtggcgtaa cagcggtatc aacagcgacg agcaggaact gatgatttgg   2940
ctgtactatg atggcctgca accggcgggt agcaaggtta agagatcgt ggttccgatt   3000 gtggttaacg gcaccccggt gaacgcgacc ttcgaggttt ggaaagcgaa catcggttgg   3060
gaatatgttg cgtttcgtat caagaccccg attaagaag gcaccgtgac catcccgtac   3120
ggtgcgttca ttagcgcggc ggcgaacgtt accagcctgg cgaactaccc ggagctgtat   3180
ctggaggacg ttgaagtggg caccgaatat ggcaccccga gcaccaccag cgcgcacctg   3240
gagtggtggt tttataacgt gagcctggag taccgtccgg gtgaaccgct gctgagccag   3300
ccgccggcgg agggcagcgc gccgagcgaa ggcggtcaaa ccccgagcga gggtgcgacc   3360
accggcaccc tggacgttaa gctggtgaac agctggggca ccggtgcgca gtatgaagtt   3420
agcgtgaacc tggataccag cagcacctgg aagctgctga tcaagattaa agatggcaaa   3480
```

-continued

| | |
|---|---|
| atcagcgaca tttggggtgc gagcattgtg ggcacccagg gtgactacgt ggttgttcag | 3540 |
| ccgagcagcc cgaccgcgag cgcgaccgtt ggcttcgtga ccagcggtaa cgcgccgctg | 3600 |
| gttgaggaag cggtgctgct gagcggtgac aaagttctgg cgacctggac cgcgccgacc | 3660 |
| gcgagcgcga gcgatctgaa cgtgaccatc aagattgata gcgagtggga cagcggtttc | 3720 |
| gttgtgaaaa tctatgttac caacaacggc aacgcgccgg tgagcagctg gcagattaag | 3780 |
| ctgcgtatga ccagcctgat cagcagcatc tggggtggca cctacaccgc gagcggtgac | 3840 |
| gttgtgacca tcgtgccgac cggcaacaac accgttatca acccgggcga taccgtggaa | 3900 |
| attggtttcg tggcgagcaa acagggtgcg tatgtgtatc cggaactgat tggtgtggag | 3960 |
| attctgtaa | 3969 |

<210> SEQ ID NO 22
<211> LENGTH: 39
<212> TYPE: DNA
<213> ORGANISM: Artificial Sequence
<220> FEATURE:
<223> OTHER INFORMATION: Forward primer for sub-cloning of SEQ ID NO. 21
      into pRham N-His SUMO

<400> SEQUENCE: 22
cgcgaacaga ttggaggtta tcgtcaaaag gcgctggcg                                  39

<210> SEQ ID NO 23
<211> LENGTH: 39
<212> TYPE: DNA
<213> ORGANISM: Artificial Sequence
<220> FEATURE:
<223> OTHER INFORMATION: Reverse primer for sub-cloning of SEQ ID NO. 21
      into pRham N-His SUMO

<400> SEQUENCE: 23
gtggcggccg ctctattaca gaatctccac accaatcag                                  39

<210> SEQ ID NO 24
<211> LENGTH: 4287
<212> TYPE: DNA
<213> ORGANISM: Artificial Sequence
<220> FEATURE:
<223> OTHER INFORMATION: P16O17 sequence with N-terminal His-tag and
      SUMO-tag

<400> SEQUENCE: 24

| | |
|---|---|
| atgcatcatc accaccatca cgggtccctg caggactcag aagtcaatca agaagctaag | 60 |
| ccagaggtca agccagaagt caagcctgag actcacatca atttaaaggt gtccgatgga | 120 |
| tcttcagaga tcttcttcaa gatcaaaaag accactcctt taagaaggct gatggaagcg | 180 |
| ttcgctaaaa gacagggtaa ggaaatggac tccttaacgt tcttgtacga cggtattgaa | 240 |
| attcaagctg atcagacccc tgaagatttg acatggagg ataacgatat tattgaggct | 300 |
| caccgcgaac agattggagg ttatcgtcaa aaggcgctgg cggtgttcgt tctgttcgtg | 360 |
| gttctggcgg gtgttgcggg tagcattccg gcgggttacg cggcgaccaa caccagcacc | 420 |
| tataccaccc cgaccggcat ctactatgag gttcgtggtg acaccatcta catgattaac | 480 |
| gtggcgaccg cgaggaaac cccgattcac ctgttcggcg ttaactggtt cggttttgag | 540 |
| accccgaact acgtggttca cggcctgtgg agccgtaact gggaagacat gctgctgcaa | 600 |
| atcaaaagcc tgggttttcaa cgcgattcgt ctgccgtttt gcacccaaag cgtgaagccg | 660 |
| ggcaccatgc cgaccggtat cgattatgcg aaaaacccgg acctgcaagg cctggacagc | 720 |

-continued

```
gttcaaatca tggagaagat cattaagaaa gcgggcgatc tgggtatttt cgtgctgctg      780
gactaccacc gtatcggttg caacttcatt gaaccgctgt ggtataccga tagctttagc      840
gagcaggact acatcaacac ctgggttgaa gtggcgcaac gttttggcaa gtattggaac      900
gttattggtg cggacctgaa aaacgaaccg cacagcagca gcccggcgcc ggctgcgtac      960
accgatggca gcggtgcgac ctgggtatg ggtaacaacg cgaccgattg gaacctggcg     1020
gcggagcgta tcggcaaagc gattctggaa gttgcgccgc actggctgat cttcgtggag     1080
ggcacccagt ttaccacccc ggaaattgat ggcagctata agtggggtca caacgcgtgg     1140
tggggtggca acctgatggg tgttcgtaag tacccggtga acctgccgcg taacaaactg     1200
gtttacagcc cgcacgtgta tggtccggat gtttacgacc aaccgtattt cgacccggcg     1260
gagggctttc cggataacct gccggacatc tggtatcacc acttcggtta tgttaagctg     1320
gatctgggct atccggtggt tattggtgaa tttggtggca aatacggtca cggtggcgat     1380
ccgcgtgacg tgacctggca gaacaagatc attgactgga tgatccaaaa caagttctgc     1440
gatttctttt attggagctg gaacccgaac agcggtgaca ccggtggtat cctgcaagac     1500
gattggacca ccatttggga ggacaagtac aacaacctga acgtctgat ggatagctgt     1560 agcggtaacg cgaccgcgcc gagcgttccg acgaccacga ccaccaccag caccccgccg     1620
actactacta ctactactac cagcaccccg accaccacca cccaaacccc gactactact     1680
accccgacta ctacaactac taccaccacc accccgagca caacgtgcc gttcgaaacc     1740 gttaacgtgc tgccgaccag cagccagtac gagggcacca gcgttgaagt ggtttgcgat     1800
ggcacccaat gcgcgagcag cgtgtggggc gcgccgaacc tgtggggcgt ggttaaaatc     1860
ggtaacgcga cgatggaccc gaacgtgtgg ggctgggagg acgtttacaa gaccgcgccg     1920
caggatatcg gcaccggtag caccaagatg gaaattcgta acggtgttct gaaagtgacc     1980
aacctgtgga acattaacat gcacccgaag tacaacacga tggcgtatcc ggaagtgatc     2040
tacggcgcga aaccgtgggg taaccagccg attaacgcgc cgaacttcgt gctgccgatc     2100
aaagttagcc aactgccgcg tattctggtg gacaccaagt acaccctgga agagcttcc     2160 ccgggtaaca acttcgcgtt tgaagcgtgg ctgttaaag atgcgaacaa catgcgtgcg     2220
ccgggtcagg gtgattatga gatcatggtg caactgtaca ttgaaggtgg ctaccggcg     2280 ggctatgata agggtccggt tctgaccgtt gatgtgccga tcattgtgga cggtcgtctg     2340
ctgaaccaga ccttcgaact gtacgatgtt atcgcggacg cgggctggcg tttctttacc     2400
tttaagccga ccaaaaacta taacggtagc gaggtggttt cgactacac caagttcatc     2460 gaaatcgtgg ataactacct gggtggcggt agcctgacca ccactacct gatgagcctg     2520 gagttcggca ccgaaatcta taccaacggt tgcaccagct ttccgtgcac cgttgatgtg     2580
cgttggaccc tggacaagta ccgtttcatt ctggcgccgg gtacgatggc gaccgaggaa     2640
gcgatgcgtg ttctggtggg cgaggttcag ccgccggcga gcaccaccac cagccagacc     2700
accaccagca ccaccacccc gaccccgact actacaacaa ccacccagac cagcaccact     2760
actaccacca ccagcccgcc gaccaccacc gcgccggcgc aggatgtgat caagctgcgt     2820
tatccggacg atggtcaatg gccggaagcg ccgattgacc gtgatggcga cggtaacccg     2880
gagttttaca tcgaaattaa cccgtggaac atcctgagcg cggagggtta tgcggaaatg     2940
acctacaacc tgagcagcgg cgttctgcac tacgtgcaag cgctggacag catcaccctg     3000
aagaacggcg gtgcgtgggt tcacggctat ccggagattt tctacggtaa caaaccgtgg     3060
aacaacaaca gcgcgaccga tggcgaagtg ccgctgccgg gcaaagttag caacctgagc     3120
```

```
aactttttatc tgaccgtgag ctacaagctg ctgccgaaaa acggcctgcc gatcaacctg    3180
gcgattgaga gctggctgac ccgtgaaccg tggcgtaaca gcggtatcaa cagcgacgag    3240
caggaactga tgatttggct gtactatgat ggcctgcaac cggcgggtag caaggttaaa    3300
gagatcgtgg ttccgattgt ggttaacggc accccggtga acgcgacctt cgaggtttgg    3360
aaagcgaaca tcggttggga atatgttgcg tttcgtatca agaccccgat taaagaaggc    3420
accgtgacca tcccgtacgg tgcgttcatt agcgcggcgg cgaacgttac cagcctggcg    3480
aactacccgg agctgtatct ggaggacgtt gaagtgggca ccgaatatgg caccccgagc    3540
accaccagcg cgcacctgga gtggtggttt tataacgtga gcctggagta ccgtccgggt    3600
gaaccgctgc tgagccagcc gccggcggag ggcagcgcgc cgagcgaagg cggtcaaacc    3660
ccgagcgagg tgcgaccac cggcaccctg gacgttaagc tggtgaacag ctggggcacc    3720
ggtgcgcagt atgaagttag cgtgaacctg gataccagca gcacctggaa gctgctgatc    3780
aagattaaag atggcaaaat cagcgacatt tggggtgcga gcattgtggg cacccagggt    3840
gactacgtgg ttgttcagcc gagcagcccg accgcgagcg cgaccgttgg cttcgtgacc    3900
agcggtaacg cgccgctggt tgaggaagcg gtgctgctga gcggtgacaa agttctggcg    3960
acctggaccg cgccgaccgc gagcgcgagc gatctgaacg tgaccatcaa gattgatagc    4020
gagtgggaca gcggtttcgt tgtgaaaatc tatgttacca acaacggcaa cgcgccggtg    4080
agcagctggc agattaagct gcgtatgacc agcctgatca gcagcatctg gggtggcacc    4140
tacaccgcga gcggtgacgt tgtgaccatc gtgccgaccg gcaacaacac cgttatcaac    4200
ccgggcgata ccgtggaaat tggtttcgtg gcgagcaaac agggtgcgta tgtgtatccg    4260
gaactgattg gtgtggagat tctgtaa                                       4287
```

<210> SEQ ID NO 25
<211> LENGTH: 1428
<212> TYPE: PRT
<213> ORGANISM: Artificial Sequence
<220> FEATURE:
<223> OTHER INFORMATION: P16O17 sequence with N-terminal His-tag and SUMO-tag

<400> SEQUENCE: 25

```
Met His His His His His His Gly Ser Leu Gln Asp Ser Glu Val Asn
1               5                   10                  15

Gln Glu Ala Lys Pro Glu Val Lys Pro Glu Val Lys Pro Glu Thr His
            20                  25                  30

Ile Asn Leu Lys Val Ser Asp Gly Ser Ser Glu Ile Phe Phe Lys Ile
        35                  40                  45

Lys Lys Thr Thr Pro Leu Arg Arg Leu Met Glu Ala Phe Ala Lys Arg
    50                  55                  60

Gln Gly Lys Glu Met Asp Ser Leu Thr Phe Leu Tyr Asp Gly Ile Glu
65                  70                  75                  80

Ile Gln Ala Asp Gln Thr Pro Glu Asp Leu Asp Met Glu Asp Asn Asp
                85                  90                  95

Ile Ile Glu Ala His Arg Glu Gln Ile Gly Gly Tyr Arg Gln Lys Ala
            100                 105                 110

Leu Ala Val Phe Val Leu Phe Val Val Leu Ala Gly Val Ala Gly Ser
        115                 120                 125

Ile Pro Ala Gly Tyr Ala Ala Thr Asn Thr Ser Thr Tyr Thr Thr Pro
    130                 135                 140
```

```
Thr Gly Ile Tyr Tyr Glu Val Arg Gly Asp Thr Ile Tyr Met Ile Asn
145                 150                 155                 160

Val Ala Thr Gly Glu Glu Thr Pro Ile His Leu Phe Gly Val Asn Trp
            165                 170                 175

Phe Gly Phe Glu Thr Pro Asn Tyr Val Val His Gly Leu Trp Ser Arg
            180                 185                 190

Asn Trp Glu Asp Met Leu Leu Gln Ile Lys Ser Leu Gly Phe Asn Ala
        195                 200                 205

Ile Arg Leu Pro Phe Cys Thr Gln Ser Val Lys Pro Gly Thr Met Pro
    210                 215                 220

Thr Gly Ile Asp Tyr Ala Lys Asn Pro Asp Leu Gln Gly Leu Asp Ser
225                 230                 235                 240

Val Gln Ile Met Glu Lys Ile Ile Lys Lys Ala Gly Asp Leu Gly Ile
            245                 250                 255

Phe Val Leu Leu Asp Tyr His Arg Ile Gly Cys Asn Phe Ile Glu Pro
            260                 265                 270

Leu Trp Tyr Thr Asp Ser Phe Ser Glu Gln Asp Tyr Ile Asn Thr Trp
        275                 280                 285

Val Glu Val Ala Gln Arg Phe Gly Lys Tyr Trp Asn Val Ile Gly Ala
    290                 295                 300

Asp Leu Lys Asn Glu Pro His Ser Ser Ser Pro Ala Pro Ala Ala Tyr
305                 310                 315                 320

Thr Asp Gly Ser Gly Ala Thr Trp Gly Met Gly Asn Asn Ala Thr Asp
            325                 330                 335

Trp Asn Leu Ala Ala Glu Arg Ile Gly Lys Ala Ile Leu Glu Val Ala
            340                 345                 350

Pro His Trp Leu Ile Phe Val Glu Gly Thr Gln Phe Thr Thr Pro Glu
        355                 360                 365

Ile Asp Gly Ser Tyr Lys Trp Gly His Asn Ala Trp Trp Gly Gly Asn
    370                 375                 380

Leu Met Gly Val Arg Lys Tyr Pro Val Asn Leu Pro Arg Asn Lys Leu
385                 390                 395                 400

Val Tyr Ser Pro His Val Tyr Gly Pro Asp Val Tyr Asp Gln Pro Tyr
            405                 410                 415

Phe Asp Pro Ala Glu Gly Phe Pro Asp Asn Leu Pro Asp Ile Trp Tyr
            420                 425                 430

His His Phe Gly Tyr Val Lys Leu Asp Leu Gly Tyr Pro Val Val Ile
        435                 440                 445

Gly Glu Phe Gly Gly Lys Tyr Gly His Gly Gly Asp Pro Arg Asp Val
    450                 455                 460

Thr Trp Gln Asn Lys Ile Ile Asp Trp Met Ile Gln Asn Lys Phe Cys
465                 470                 475                 480

Asp Phe Phe Tyr Trp Ser Trp Asn Pro Asn Ser Gly Asp Thr Gly Gly
            485                 490                 495

Ile Leu Gln Asp Asp Trp Thr Thr Ile Trp Glu Asp Lys Tyr Asn Asn
            500                 505                 510

Leu Lys Arg Leu Met Asp Ser Cys Ser Gly Asn Ala Thr Ala Pro Ser
        515                 520                 525

Val Pro Thr Thr Thr Thr Thr Ser Thr Pro Thr Thr Thr
    530                 535                 540

Thr Thr Thr Ser Thr Pro Thr Thr Thr Gln Thr Pro Thr Thr Thr
545                 550                 555                 560

Thr Pro Thr Thr Thr Thr Thr Thr Thr Pro Ser Asn Asn Val
```

-continued

```
                565                 570                 575
Pro Phe Glu Thr Val Asn Val Leu Pro Thr Ser Ser Gln Tyr Glu Gly
                580                 585                 590

Thr Ser Val Glu Val Val Cys Asp Gly Thr Gln Cys Ala Ser Ser Val
            595                 600             605

Trp Gly Ala Pro Asn Leu Trp Gly Val Val Lys Ile Gly Asn Ala Thr
610                 615                 620

Met Asp Pro Asn Val Trp Gly Trp Glu Asp Val Tyr Lys Thr Ala Pro
625                 630                 635                 640

Gln Asp Ile Gly Thr Gly Ser Thr Lys Met Glu Ile Arg Asn Gly Val
                645                 650                 655

Leu Lys Val Thr Asn Leu Trp Asn Ile Asn Met His Pro Lys Tyr Asn
                660                 665                 670

Thr Met Ala Tyr Pro Glu Val Ile Tyr Gly Ala Lys Pro Trp Gly Asn
            675                 680                 685

Gln Pro Ile Asn Ala Pro Asn Phe Val Leu Pro Ile Lys Val Ser Gln
690                 695                 700

Leu Pro Arg Ile Leu Val Asp Thr Lys Tyr Thr Leu Glu Lys Ser Phe
705                 710                 715                 720

Pro Gly Asn Asn Phe Ala Phe Glu Ala Trp Leu Phe Lys Asp Ala Asn
                725                 730                 735

Asn Met Arg Ala Pro Gly Gln Gly Asp Tyr Glu Ile Met Val Gln Leu
            740                 745                 750

Tyr Ile Glu Gly Gly Tyr Pro Ala Gly Tyr Asp Lys Gly Pro Val Leu
            755                 760                 765

Thr Val Asp Val Pro Ile Ile Val Asp Gly Arg Leu Leu Asn Gln Thr
770                 775                 780

Phe Glu Leu Tyr Asp Val Ile Ala Asp Ala Gly Trp Arg Phe Phe Thr
785                 790                 795                 800

Phe Lys Pro Thr Lys Asn Tyr Asn Gly Ser Glu Val Val Phe Asp Tyr
                805                 810                 815

Thr Lys Phe Ile Glu Ile Val Asp Asn Tyr Leu Gly Gly Gly Ser Leu
            820                 825                 830

Thr Asn His Tyr Leu Met Ser Leu Glu Phe Gly Thr Glu Ile Tyr Thr
835                 840                 845

Asn Gly Cys Thr Ser Phe Pro Cys Thr Val Asp Val Arg Trp Thr Leu
850                 855                 860

Asp Lys Tyr Arg Phe Ile Leu Ala Pro Gly Thr Met Ala Thr Glu Glu
865                 870                 875                 880

Ala Met Arg Val Leu Val Gly Glu Val Gln Pro Ala Ser Thr Thr Thr
                885                 890                 895

Thr Ser Gln Thr Thr Thr Ser Thr Thr Thr Pro Thr Pro Thr Thr Thr
            900                 905                 910

Thr Thr Thr Gln Thr Ser Thr Thr Thr Thr Thr Ser Pro Pro Thr Thr
            915                 920                 925

Thr Thr Ala Pro Ala Gln Asp Val Ile Lys Leu Arg Tyr Pro Asp Asp
930                 935                 940

Gly Gln Trp Pro Glu Ala Pro Ile Asp Arg Asp Gly Asp Gly Asn Pro
945                 950                 955                 960

Glu Phe Tyr Ile Glu Ile Asn Pro Trp Asn Ile Leu Ser Ala Glu Gly
                965                 970                 975

Tyr Ala Glu Met Thr Tyr Asn Leu Ser Ser Gly Val Leu His Tyr Val
            980                 985                 990
```

```
Gln Ala Leu Asp Ser Ile Thr Leu Lys Asn Gly Gly Ala Trp Val His
        995                 1000                    1005

Gly Tyr Pro Glu Ile Phe Tyr Gly Asn Lys Pro Trp Asn Asn Asn
    1010                1015                1020

Ser Ala Thr Asp Gly Glu Val Pro Leu Pro Gly Lys Val Ser Asn
    1025                1030                1035

Leu Ser Asn Phe Tyr Leu Thr Val Ser Tyr Lys Leu Leu Pro Lys
    1040                1045                1050

Asn Gly Leu Pro Ile Asn Leu Ala Ile Glu Ser Trp Leu Thr Arg
    1055                1060                1065

Glu Pro Trp Arg Asn Ser Gly Ile Asn Ser Asp Glu Gln Glu Leu
    1070                1075                1080

Met Ile Trp Leu Tyr Tyr Asp Gly Leu Gln Pro Ala Gly Ser Lys
    1085                1090                1095

Val Lys Glu Ile Val Val Pro Ile Val Val Asn Gly Thr Pro Val
    1100                1105                1110

Asn Ala Thr Phe Glu Val Trp Lys Ala Asn Ile Gly Trp Glu Tyr
    1115                1120                1125

Val Ala Phe Arg Ile Lys Thr Pro Ile Lys Glu Gly Thr Val Thr
    1130                1135                1140

Ile Pro Tyr Gly Ala Phe Ile Ser Ala Ala Ala Asn Val Thr Ser
    1145                1150                1155

Leu Ala Asn Tyr Pro Glu Leu Tyr Leu Glu Asp Val Glu Val Gly
    1160                1165                1170

Thr Glu Tyr Gly Thr Pro Ser Thr Thr Ser Ala His Leu Glu Trp
    1175                1180                1185

Trp Phe Tyr Asn Val Ser Leu Glu Tyr Arg Pro Gly Glu Pro Leu
    1190                1195                1200

Leu Ser Gln Pro Pro Ala Glu Gly Ser Ala Pro Ser Glu Gly Gly
    1205                1210                1215

Gln Thr Pro Ser Glu Gly Ala Thr Thr Gly Thr Leu Asp Val Lys
    1220                1225                1230

Leu Val Asn Ser Trp Gly Thr Gly Ala Gln Tyr Glu Val Ser Val
    1235                1240                1245

Asn Leu Asp Thr Ser Ser Thr Trp Lys Leu Leu Ile Lys Ile Lys
    1250                1255                1260

Asp Gly Lys Ile Ser Asp Ile Trp Gly Ala Ser Ile Val Gly Thr
    1265                1270                1275

Gln Gly Asp Tyr Val Val Val Gln Pro Ser Ser Pro Thr Ala Ser
    1280                1285                1290

Ala Thr Val Gly Phe Val Thr Ser Gly Asn Ala Pro Leu Val Glu
    1295                1300                1305

Glu Ala Val Leu Leu Ser Gly Asp Lys Val Leu Ala Thr Trp Thr
    1310                1315                1320

Ala Pro Thr Ala Ser Ala Ser Asp Leu Asn Val Thr Ile Lys Ile
    1325                1330                1335

Asp Ser Glu Trp Asp Ser Gly Phe Val Val Lys Ile Tyr Val Thr
    1340                1345                1350

Asn Asn Gly Asn Ala Pro Val Ser Ser Trp Gln Ile Lys Leu Arg
    1355                1360                1365

Met Thr Ser Leu Ile Ser Ser Ile Trp Gly Gly Thr Tyr Thr Ala
    1370                1375                1380
```

```
Ser Gly Asp Val Val Thr Ile Val Pro Thr Gly Asn Asn Thr Val
    1385                1390                1395

Ile Asn Pro Gly Asp Thr Val Glu Ile Gly Phe Val Ala Ser Lys
    1400                1405                1410

Gln Gly Ala Tyr Val Tyr Pro Glu Leu Ile Gly Val Glu Ile Leu
    1415                1420                1425
```

<210> SEQ ID NO 26
<211> LENGTH: 18
<212> TYPE: DNA
<213> ORGANISM: Artificial Sequence
<220> FEATURE:
<223> OTHER INFORMATION: His-tag sequence

<400> SEQUENCE: 26

```
catcatcacc accatcac                                                   18
```

<210> SEQ ID NO 27
<211> LENGTH: 6
<212> TYPE: PRT
<213> ORGANISM: Artificial Sequence
<220> FEATURE:
<223> OTHER INFORMATION: His-tag sequence

<400> SEQUENCE: 27

```
His His His His His His
1               5
```

<210> SEQ ID NO 28
<211> LENGTH: 300
<212> TYPE: DNA
<213> ORGANISM: Artificial Sequence
<220> FEATURE:
<223> OTHER INFORMATION: SUMO-tag sequence

<400> SEQUENCE: 28

```
gggtccctgc aggactcaga agtcaatcaa gaagctaagc cagaggtcaa gccagaagtc     60
aagcctgaga ctcacatcaa tttaaaggtg tccgatggat cttcagagat cttcttcaag    120
atcaaaaaga ccactccttt aagaaggctg atggaagcgt tcgctaaaag acagggtaag    180
gaaatggact ccttaacgtt cttgtacgac ggtattgaaa ttcaagctga tcagaccct     240 gaagatttgg acatggagga taacgatatt attgaggctc accgcgaaca gattggaggt    300
```

<210> SEQ ID NO 29
<211> LENGTH: 100
<212> TYPE: PRT
<213> ORGANISM: Artificial Sequence
<220> FEATURE:
<223> OTHER INFORMATION: SUMO-tag sequence

<400> SEQUENCE: 29

```
Gly Ser Leu Gln Asp Ser Glu Val Asn Gln Glu Ala Lys Pro Glu Val
1               5                   10                  15

Lys Pro Glu Val Lys Pro Glu Thr His Ile Asn Leu Lys Val Ser Asp
                20                  25                  30

Gly Ser Ser Glu Ile Phe Phe Lys Ile Lys Lys Thr Thr Pro Leu Arg
            35                  40                  45

Arg Leu Met Glu Ala Phe Ala Lys Arg Gln Gly Lys Glu Met Asp Ser
        50                  55                  60

Leu Thr Phe Leu Tyr Asp Gly Ile Glu Ile Gln Ala Asp Gln Thr Pro
65                  70                  75                  80
```

```
Glu Asp Leu Asp Met Glu Asp Asn Asp Ile Ile Glu Ala His Arg Glu
                85                  90                  95

Gln Ile Gly Gly
            100

<210> SEQ ID NO 30
<211> LENGTH: 841
<212> TYPE: PRT
<213> ORGANISM: Thermotoga maritima

<400> SEQUENCE: 30

Met Ile Asn Val Ala Thr Gly Glu Glu Thr Pro Ile His Leu Phe Gly
1               5                   10                  15

Val Asn Trp Phe Gly Phe Glu Thr Pro Asn Tyr Val Val His Gly Leu
            20                  25                  30

Trp Ser Arg Asn Trp Glu Asp Met Leu Leu Gln Ile Lys Ser Leu Gly
        35                  40                  45

Phe Asn Ala Ile Arg Leu Pro Phe Cys Thr Gln Ser Val Lys Pro Gly
    50                  55                  60

Thr Met Pro Thr Ala Ile Asp Tyr Ala Lys Asn Pro Asp Leu Gln Gly
65                  70                  75                  80

Leu Asp Ser Val Gln Ile Met Glu Lys Ile Ile Lys Lys Ala Gly Asp
                85                  90                  95

Leu Gly Ile Phe Val Leu Leu Asp Tyr His Arg Ile Gly Cys Asn Phe
            100                 105                 110

Ile Glu Pro Leu Trp Tyr Thr Asp Ser Phe Ser Glu Gln Asp Tyr Ile
        115                 120                 125

Asn Thr Trp Val Glu Val Ala Gln Arg Phe Gly Lys Tyr Trp Asn Val
    130                 135                 140

Ile Gly Ala Asp Leu Lys Asn Glu Pro His Ser Ser Pro Ala Pro
145                 150                 155                 160

Ala Ala Tyr Thr Asp Gly Ser Gly Ala Thr Trp Gly Met Gly Asn Asn
                165                 170                 175

Ala Thr Asp Trp Asn Leu Ala Ala Glu Arg Ile Gly Arg Ala Ile Leu
            180                 185                 190

Glu Val Ala Pro Gln Trp Val Ile Phe Val Glu Gly Thr Gln Phe Thr
        195                 200                 205

Thr Pro Glu Ile Asp Gly Arg Tyr Lys Trp Gly His Asn Ala Trp Trp
    210                 215                 220

Gly Gly Asn Leu Met Gly Val Arg Lys Tyr Pro Val Asn Leu Pro Arg
225                 230                 235                 240

Asp Lys Val Val Tyr Ser Pro Gln Val Tyr Gly Ser Glu Val Tyr Asp
                245                 250                 255

Gln Pro Tyr Phe Asp Pro Gly Glu Gly Phe Pro Asp Asn Leu Pro Glu
            260                 265                 270

Ile Trp Tyr His His Phe Gly Tyr Val Lys Leu Asp Leu Gly Tyr Pro
        275                 280                 285

Val Val Ile Gly Glu Phe Gly Gly Lys Tyr Gly His Gly Gly Asp Pro
    290                 295                 300

Arg Asp Val Thr Trp Gln Asn Lys Ile Ile Asp Trp Met Ile Gln Asn
305                 310                 315                 320

Lys Phe Cys Asp Phe Phe Tyr Trp Ser Trp Asn Pro Asn Ser Gly Asp
                325                 330                 335

Thr Gly Gly Ile Leu Lys Asp Asp Trp Thr Thr Ile Trp Glu Asp Lys
            340                 345                 350
```

```
Tyr Asn Asn Leu Lys Arg Leu Met Asp Ser Cys Ser Gly Asn Ala Thr
        355                 360                 365

Ala Pro Ser Val Pro Thr Thr Thr Thr Thr Ser Thr Pro Pro Thr
370                 375                 380

Thr Thr Thr Thr Thr Thr Ser Thr Pro Thr Thr Thr Thr Gln Thr Pro
385                 390                 395                 400

Thr Thr Thr Thr Pro Thr Thr Thr Thr Thr Thr Thr Thr Pro Ser
                405                 410                 415

Asn Asn Val Pro Phe Glu Ile Val Asn Val Leu Pro Thr Ser Ser Gln
                420                 425                 430

Tyr Glu Gly Thr Ser Val Glu Val Val Cys Asp Gly Thr Gln Cys Ala
        435                 440                 445

Ser Ser Val Trp Gly Ala Pro Asn Leu Trp Gly Val Val Lys Ile Gly
        450                 455                 460

Asn Ala Thr Met Asp Pro Asn Val Trp Gly Trp Glu Asp Val Tyr Lys
465                 470                 475                 480

Thr Ala Pro Gln Asp Ile Gly Thr Gly Ser Thr Lys Met Glu Ile Arg
                485                 490                 495

Asn Gly Val Leu Lys Val Thr Asn Leu Trp Asn Ile Asn Met His Pro
                500                 505                 510

Lys Tyr Asn Thr Met Ala Tyr Pro Glu Val Ile Tyr Gly Ala Lys Pro
        515                 520                 525

Trp Gly Asn Gln Pro Ile Asn Ala Pro Asn Phe Val Leu Pro Ile Lys
        530                 535                 540

Val Ser Gln Leu Pro Arg Ile Leu Val Asp Thr Lys Tyr Thr Leu Glu
545                 550                 555                 560

Lys Ser Phe Pro Gly Asn Asn Phe Ala Phe Glu Ala Trp Leu Phe Lys
                565                 570                 575

Asp Ala Asn Asn Met Arg Ala Pro Gly Gln Gly Asp Tyr Glu Ile Met
                580                 585                 590

Val Gln Leu Tyr Ile Glu Gly Gly Tyr Pro Ala Gly Tyr Asp Lys Gly
        595                 600                 605

Pro Val Leu Thr Val Asp Val Pro Ile Ile Val Asp Gly Arg Leu Val
        610                 615                 620

Asn Gln Thr Phe Glu Leu Tyr Asp Val Ile Ala Asp Ala Gly Trp Arg
625                 630                 635                 640

Phe Phe Thr Phe Lys Pro Thr Lys Asn Tyr Asn Gly Ser Glu Val Val
                645                 650                 655

Phe Asp Tyr Thr Lys Phe Ile Glu Ile Val Asp Asn Tyr Leu Gly Gly
                660                 665                 670

Gly Ser Leu Thr Asn His Tyr Leu Met Ser Leu Glu Phe Gly Thr Glu
        675                 680                 685

Ile Tyr Thr Asn Gly Cys Thr Ser Phe Pro Cys Thr Val Asp Val Arg
        690                 695                 700

Trp Thr Leu Asp Lys Tyr Arg Phe Ile Leu Ala Pro Gly Thr Met Ala
705                 710                 715                 720

Thr Glu Glu Ala Met Arg Val Leu Val Gly Glu Val Gln Pro Pro Ala
                725                 730                 735

Ser Thr Thr Thr Ser Gln Thr Thr Ser Thr Thr Thr Pro Thr Pro
                740                 745                 750

Thr Thr Thr Thr Thr Thr Gln Thr Ser Thr Thr Thr Thr Thr Ser
        755                 760                 765
```

```
Pro Pro Thr Thr Thr Ala Pro Ala Gln Asp Val Ile Lys Leu Arg Tyr
    770                 775                 780

Pro Asp Asp Gly Gln Trp Pro Glu Ala Pro Ile Asp Arg Asp Gly Asp
785                 790                 795                 800

Gly Asn Pro Glu Phe Tyr Ile Glu Ile Asn Pro Trp Asn Ile Leu Ser
                805                 810                 815

Ala Glu Ser Tyr Ala Glu Met Thr Tyr Asn Leu Ser Ser Gly Val Leu
            820                 825                 830

His Tyr Val Gln Ala Leu Asp Ser Ile
        835                 840

<210> SEQ ID NO 31
<211> LENGTH: 754
<212> TYPE: PRT
<213> ORGANISM: Unknown
<220> FEATURE:
<223> OTHER INFORMATION: Protein from archaeon AEPII1a, an unidentified
      species of the genus Thermococcus

<400> SEQUENCE: 31

Met Ser Ser Lys Gln Lys Thr Val Ala Ile Phe Val Leu Phe Val Ala
1               5                   10                  15

Leu Ala Gly Val Ala Gly Ser Ile Pro Ala Ser Tyr Ala Ala Pro Ser
                20                  25                  30

Thr Ser Thr Tyr Thr Thr Pro Thr Gly Ile Tyr Tyr Glu Val Arg Gly
            35                  40                  45

Asp Thr Ile Tyr Met Ile Asn Val Ala Thr Gly Glu Glu Thr Pro Ile
        50                  55                  60

His Leu Phe Gly Val Asn Trp Phe Gly Phe Glu Thr Pro Asn Tyr Val
65                  70                  75                  80

Val His Gly Leu Trp Ser Arg Asn Trp Glu Asp Met Leu Leu Gln Ile
                85                  90                  95

Lys Ser Leu Gly Phe Asn Ala Ile Arg Leu Pro Phe Cys Thr Gln Ser
                100                 105                 110

Val Lys Pro Gly Thr Met Pro Thr Ala Ile Asp Tyr Ala Lys Asn Pro
            115                 120                 125

Asp Leu Gln Gly Leu Asp Ser Val Gln Ile Met Glu Lys Ile Ile Lys
        130                 135                 140

Lys Ala Gly Asp Leu Gly Ile Phe Val Leu Leu Asp Tyr His Arg Ile
145                 150                 155                 160

Gly Cys Asn Phe Ile Glu Pro Leu Trp Tyr Thr Asp Ser Phe Ser Glu
                165                 170                 175

Gln Asp Tyr Ile Asn Thr Trp Val Glu Val Ala Gln Arg Phe Gly Lys
            180                 185                 190

Tyr Leu Asn Val Ile Gly Ala Asp Leu Lys Asn Glu Pro His Ser Ser
        195                 200                 205

Ser Pro Ala Pro Ala Ala Tyr Thr Asp Gly Ser Gly Ala Thr Trp Gly
    210                 215                 220

Met Gly Asn Asn Ala Thr Asp Trp Asn Leu Ala Ala Glu Arg Ile Gly
225                 230                 235                 240

Arg Ala Ile Leu Glu Val Ala Pro His Trp Leu Ile Phe Val Glu Gly
                245                 250                 255

Thr Gln Phe Thr Thr Pro Glu Ile Asp Gly Ser Tyr Lys Trp Gly His
            260                 265                 270

Asn Ala Trp Trp Gly Gly Asn Leu Met Gly Val Arg Lys Tyr Pro Val
        275                 280                 285
```

```
Asn Leu Pro Arg Asn Lys Leu Val Tyr Ser Pro His Val Tyr Gly Pro
    290                 295                 300

Asp Val Tyr Asp Gln Pro Tyr Phe Asp Pro Ala Glu Gly Phe Pro Asp
305                 310                 315                 320

Asn Leu Pro Asp Ile Trp Tyr His His Phe Gly Tyr Val Lys Leu Asp
                325                 330                 335

Leu Gly Tyr Pro Val Val Ile Gly Glu Phe Gly Gly Lys Tyr Gly His
            340                 345                 350

Gly Gly Asp Pro Arg Asp Val Thr Trp Gln Asn Lys Ile Ile Asp Trp
        355                 360                 365

Met Ile Gln Asn Lys Phe Cys Asp Phe Phe Tyr Trp Ser Trp Asn Pro
370                 375                 380

Asn Ser Gly Asp Thr Gly Gly Ile Leu Lys Asp Asp Trp Thr Thr Ile
385                 390                 395                 400

Trp Glu Asp Lys Tyr Asn Asn Leu Lys Arg Leu Met Asp Ser Cys Ser
                405                 410                 415

Gly Asn Ala Thr Ala Pro Ser Val Pro Thr Thr Thr Thr Thr Thr Ser
            420                 425                 430

Thr Pro Pro Thr Thr Thr Thr Thr Thr Ser Thr Pro Thr Thr Thr
        435                 440                 445

Thr Gln Thr Pro Thr Thr Thr Thr Pro Thr Thr Thr Thr Thr Thr Thr
450                 455                 460

Thr Thr Pro Ser Asn Asn Val Pro Phe Glu Ile Val Asn Val Leu Pro
465                 470                 475                 480

Thr Ser Ser Gln Tyr Glu Gly Thr Ser Val Glu Val Val Cys Asp Gly
                485                 490                 495

Thr Gln Cys Ala Ser Ser Val Trp Gly Ala Pro Asn Leu Trp Gly Val
            500                 505                 510

Val Lys Ile Gly Asn Ala Thr Met Asp Pro Asn Val Trp Gly Trp Glu
        515                 520                 525

Asp Val Tyr Lys Thr Ala Pro Gln Asp Ile Gly Thr Gly Ser Thr Lys
        530                 535                 540

Met Glu Ile Arg Asn Gly Val Leu Lys Val Thr Asn Leu Trp Asn Ile
545                 550                 555                 560

Asn Met His Pro Lys Tyr Asn Thr Met Ala Tyr Pro Glu Val Ile Tyr
                565                 570                 575

Gly Ala Lys Pro Trp Gly Asn Gln Pro Ile Asn Ala Pro Asn Phe Val
            580                 585                 590

Leu Pro Ile Lys Val Ser Gln Leu Pro Arg Ile Leu Val Asp Thr Lys
        595                 600                 605

Tyr Thr Leu Glu Lys Ser Phe Pro Gly Asn Asn Phe Ala Phe Glu Ala
    610                 615                 620

Trp Leu Phe Lys Asp Ala Asn Asn Met Arg Ala Pro Gly Gln Gly Asp
625                 630                 635                 640

Tyr Glu Ile Met Val Gln Leu Tyr Ile Glu Gly Gly Tyr Pro Ala Gly
                645                 650                 655

Tyr Asp Lys Gly Pro Val Leu Thr Val Asp Val Pro Ile Ile Val Asp
            660                 665                 670

Gly Arg Leu Val Asn Gln Thr Phe Glu Leu Tyr Asp Val Ile Ala Asp
        675                 680                 685

Ala Gly Trp Arg Phe Phe Thr Phe Lys Pro Thr Lys Asn Tyr Asn Gly
    690                 695                 700
```

-continued

```
Ser Glu Val Val Phe Asp Tyr Gln Ser Cys Pro Ala Glu Gly Ile Gln
705                 710                 715                 720

Arg Ser Arg Arg Cys Trp Arg Glu Leu Asn Asp Pro Phe Leu Leu Gln
                725                 730                 735

Lys Leu Leu Tyr Leu Lys Asp Val Phe Gly Arg Gln Leu Lys Asp Pro
                740                 745                 750

Ser Leu
```

THERMOSTABLE CELLULASES

CROSS-REFERENCE TO RELATED APPLICATION(S)

This application is a National Phase Patent Application of International Patent Application Number PCT/EP2016/062079, filed on May 27, 2016, which claims priority of British Patent Application 1509149.9, filed May 28, 2015. The entire contents of both of which are incorporated herein by reference.

SEQUENCE LISTING

The instant application contains a Sequence Listing which has been submitted in ASCII format via EFS-Web and is hereby incorporated by reference in its entirety. Said ASCII copy filed in the International Patent Application Number PCT/EP2016/062079, was last modified on Apr. 12, 2018, and is named Amendedeolf-seql.txt and is 116,181 bytes in size.

The present invention generally relates to previously unknown thermostable cellulases from thermophilic Archaea, which are able to degrade cellulose at high temperatures, and to nucleic acids which encode the thermostable cellulases. Particularly, the invention relates to thermostable polypeptides with cellulase activity either comprising the amino acid sequence set forth in SEQ ID NO. 2, comprising the amino acid sequence as set forth in SEQ ID NO. 8 or comprising sequences which are functional parts thereof and/or which have high levels of identity thereto. Encoding nucleic acid molecules, vectors, host cells (particularly microorganisms) and uses of the polypeptides for degrading cellulose are all encompassed by the invention.

Organisms that live in extreme environments (e.g. of heat, pressure, salinity etc.) have attracted interest for their ability to thrive and to produce proteins and enzymes which are functional under such extreme conditions. Particularly, the enzymes which are produced by extremophile organisms, may have great utility in industry, e.g. in industrial processes, where extreme conditions may occur. Taq polymerase is a classic example of an enzyme obtained from a thermophilic organism (*Thermus aquaticus* isolated in culture from hot springs at Yellowstone National Park). Traditionally, enzymes from extremophiles were identified and characterised by culture-based or -dependent methods, which involve culturing the extremophile which expresses the enzyme. However, many extremophiles are not readily cultured under laboratory conditions. This has thus led to the development of new cultivation methods, although the application of these methods is slow. Further, the new methods will not allow for the cultivation of the extant diversity of microbial strains from extreme environments, necessitating new approaches to characterise and derive proteins and enzymes from such microbes.

The present inventors have now surprisingly discovered the existence of previously unknown thermostable cellulase enzymes from microbes in a petroleum reservoir 2.5 km below the sea floor of the Norwegian Sea, using culture-independent metagenomic methods. Such methods address the problems associated with culture-dependent methods of enzyme discovery and characterisation, and allow the characterisation of genomes from microbes which cannot be cultured in a laboratory. In this approach, metagenomic DNA was directly extracted from environmental microbes and then sequenced and cloned into a heterologous host to generate a metagenomic library. The library was then screened using sequence-based and function-based methods, and genes which encode cellulase enzymes were identified.

Using this culture-independent approach for characterisation of the petroleum reservoir samples, the inventors have surprisingly identified cellulase enzymes in an environment where the existence of cellulases was not expected, which enzymes have low full-length sequence identity with other known cellulase enzymes and unexpectedly have a different modular structure to known cellulases.

The expression of cellulase enzymes by the microbes living within the petroleum reservoir was a surprising result. In this regard, although petroleum reservoirs contain complex hydrocarbons trapped in porous rock formations, the availability of specific carbohydrate substrates (e.g. cellulose) within that environment was unknown. Thus, in view of the potential lack of substrate, the inventors were particularly surprised to identify and characterise the cellulase enzymes of the present invention. The inventors' studies have also determined that the identified cellulase enzymes are thermostable, which reflects the adaptation of microbes to the extreme environment provided by the petroleum reservoirs (an in situ temperature of approximately 85° C., a pressure of approximately 250 bars and high salt content).

At least one of the cellulase enzymes of the invention, specifically P16O17 (represented by SEQ ID NO. 2), has further been shown to have the unique property of being able to degrade cellulose directly to glucose. Previously, it has been considered that three distinct enzymes were required to fully degrade cellulose: (i) an endoglucanase, which cleaves internal β-(1-4)-glycosidic bonds, making chain ends accessible to other enzymes; (ii) a cellobiohydrolase (also known as an exoglucanase), which works processively from the end of a cellulose chain to degrade the cellulose into cellobiose (which is a disaccharide consisting of two glucose moieties joined by a β-(1-4)-glycosidic bond); (iii) a βglucosidase, which breaks down cellobiose molecules into its constituent glucose molecules (Yennamalli et al., Biotechnol Biofuels 6: 136, 2013).

The cellulase of SEQ ID NO: 2 is primarily an exoglucanase, but has the novel property that it degrades cellulose to yield two products: cellobiose and glucose. The enzyme is able to degrade not only amorphous carboxymethyl cellulose, but also microcrystalline cellulose, which is generally not well degraded by enzymatic methods due to its insolubility. The ability of the enzyme to degrade cellulose directly to glucose is a surprising and novel feature of the enzyme, and may be very commercially/industrially valuable in fields such as biorefining.

Furthermore, the cellulase of SEQ ID NO. 2 has extremely high activity, considerably higher than several cellulase enzymes currently commercially available. Thus the cellulase of SEQ ID NO. 2 is able to degrade cellulose considerably faster than many cellulases currently on the market. As shown herein, the cellulase of SEQ ID NO: 2 is, by itself, able to degrade both carboxymethyl cellulose and microcrystalline cellulose more efficiently than a combination of three commercially available cellulase enzymes. The cellulase of SEQ ID NO: 2 thus offers very significant advantages over those of the prior art.

Thus, the new thermostable cellulase enzymes of the present invention have particularly advantageous characteristics and have many applications in industry, including in the degradation of lignocellulosic biomass for biofuel applications and production of other bio-based products.

Accordingly, in a first aspect, the present invention provides a nucleic acid molecule which encodes a polypeptide having cellulase activity and which is thermostable, wherein said nucleic acid molecule comprises or has a nucleotide sequence selected from:
  i) a nucleotide sequence which encodes an amino acid sequence as set forth in SEQ ID NO. 2 or as set forth in SEQ ID NO. 8;
  ii) a nucleotide sequence which encodes an amino acid sequence having at least 80% sequence identity to the amino acid sequence of (i);
  iii) a nucleotide sequence which encodes a part of the amino acid sequence of (i);
  iv) a nucleotide sequence which encodes a part of the amino acid sequence of (ii) wherein said part has at least 90% identity to an amino acid sequence of SEQ ID NO. 4, SEQ ID NO. 6, SEQ ID NO. 14, SEQ ID NO. 16, SEQ ID NO. 18 or SEQ ID NO. 20;
  v) a nucleotide sequence as set forth in SEQ ID NO. 1 or as set forth in SEQ ID NO. 7;
  vi) a nucleotide sequence having at least 80% sequence identity to the nucleotide sequence of v) or a nucleotide sequence which is degenerate thereto;
  vii) a nucleotide sequence which is a part of the nucleotide sequence of v);
  viii) a nucleotide sequence which is a part of the nucleotide sequence of vi) wherein said part has at least 90% identity to a nucleotide sequence of SEQ ID NO. 3, SEQ ID NO. 5, SEQ ID NO. 13, SEQ ID NO. 15, SEQ ID NO. 17 or SEQ ID NO. 19;
    or a nucleic acid which comprises a nucleotide sequence which is complementary to the nucleotide sequence of any one of i) to vii).

Further provided is a nucleic acid molecule which encodes a polypeptide having cellulase activity and which is thermostable, wherein said nucleic acid molecule comprises or has a nucleotide sequence which encodes an amino acid sequence having at least 80% sequence identity to an amino acid sequence of SEQ ID NO. 2 and wherein a part of said nucleotide sequence encodes an amino acid sequence having at least 90% sequence identity to an amino acid sequence of any one of SEQ ID NOs. 4, 6, 14, 16, 18 or 20. Additionally, the invention provides a nucleic acid molecule which encodes a polypeptide having cellulase activity and which is thermostable wherein said nucleic acid molecule comprises or has a nucleotide sequence having at least 80% sequence identity to SEQ ID NO. 1 and wherein a part of said nucleotide sequence has at least 90% sequence identity to SEQ ID NO. 3, SEQ ID NO. 5, SEQ ID NO. 13, SEQ ID NO. 15, SEQ ID NO, 17 or SEQ ID NO. 19.

The nucleic acid molecules of the invention, encoding the novel cellulase enzymes of the invention may be obtained from archaeal sources within the petroleum reservoir samples, by culture-independent methods as discussed previously. Thus, the nucleic acids of the invention encompass the "wild type" nucleic acid sequences identified and characterised by those methods. In addition to the specific nucleotide and amino acid sequences identified, the invention also provides for parts or fragments and variants of those sequences (e.g. SEQ ID NOs. 3, 5, 13, 15, 17 or 19 which are parts of SEQ ID NO. 1 and their corresponding amino acid sequences of SEQ ID NOs. 4, 6, 14, 16, 18 or 20 which are fragments of SEQ ID NO. 2) and also for longer molecules comprising those sequences (for example nucleotide sequences SEQ ID NOs. 9 and 11 are longer variants of SEQ ID NO. 7, and their corresponding amino acid sequences SEQ ID NOs. 10 and 12 are longer variants of SEQ ID NO. 8).

In this respect, nucleotide sequences of SEQ ID NO. 1 and SEQ ID NOs. 7, 9 and 11 were specifically identified and functionally shown as encoding cellulases having amino acid sequences as set forth in SEQ ID NO. 2 and of SEQ ID NOs. 8, 10 and 12 in the present invention. Other truncated variants of the nucleotide sequence of SEQ ID NO. 1 and of the amino acid sequence of SEQ ID NO. 2 have further been identified, where the nucleotide sequences for these variants are set out in SEQ ID NOs. 3 and 5, and the amino acid sequences for the variants are set out in SEQ ID NOs. 4 and 6. Nucleic acid molecules comprising these variant nucleotide sequences encode proteins with putative cellulase activity.

Further, SEQ ID NOs. 10 and 12 have been shown to comprise a variant of the full length sequence of SEQ ID NO. 8 with over 99% identity to the sequence of SEQ ID NO. 8 across its full length. SEQ ID NO. 10 comprises an additional 21 amino acids to the N-terminus of the variant sequence of SEQ ID NO. 8 (which is over 99% identical at the amino acid level to SEQ ID NO. 8) and which has one amino acid difference as compared to the amino acid sequence of SEQ ID NO. 8 over 502 amino acids (namely a G instead of an R at position 481 of SEQ ID NO. 10). SEQ ID NO. 12 comprises an additional 41 amino acid residues to the N-terminus of the variant sequence of SEQ ID NO. 8 (which is over 99% identical at the amino acid level to SEQ ID NO. 8) and which has two amino acid differences as compared to the amino acid sequence of SEQ ID NO. 8 over 502 amino acids (namely A instead of V at residue 408 of SEQ ID NO. 12 and a G instead of an R at position 499 of SEQ ID NO. 12).

Accordingly, the nucleic acid molecule of the present invention may comprise a nucleotide sequence which encodes an amino acid sequence of SEQ ID NO. 2, SEQ ID NO. 4 or SEQ ID NO. 6, or an amino acid sequence of SEQ ID NO. 8, 10 or 12, or an amino acid sequence with at least 80% sequence identity thereto. Alternatively viewed, the nucleic acid molecule of the invention comprises a nucleotide sequence as set forth in SEQ ID NO. 1, 3 or 5, or as set forth in SEQ ID NO. 7, 9 or 11 or a nucleotide sequence with at least 80% identity thereto, or a degenerate sequence thereof. In particular, the nucleic acid molecule of the invention may comprise or have a nucleotide sequence which encodes an amino acid sequence of SEQ ID NO. 2, 4, 6, 8, 10 or 12, said nucleotide sequence having been codon-optimised for expression in a host microorganism. A codon-optimised sequence may be degenerate to an original sequence, and is altered such that codons which are rare in the intended host microorganism (by which is meant that the codon is rarely used in the host microorganism, meaning that tRNAs which recognise the codon are expressed at low levels therein) are replaced with codons which are more commonly used in the host microorganism. Codon optimisation may therefore have the effect of increasing/improving expression of a particular sequence in a host microorganism. SEQ ID NO. 21 represents a preferred codon-optimised nucleic acid sequence which encodes the polypeptide of SEQ ID NO. 2 and is codon-optimised for expression in *E. coli*. Accordingly, a nucleic acid molecule of the invention may comprise or have the nucleotide sequence of SEQ ID NO. 21.

In another embodiment, the nucleic acid molecule of the invention may comprise a nucleic acid sequence which encodes a variant of SEQ ID NO: 2, 4, 6, 8, 10 or 12, said variant having been altered to comprise one or more tag sequences. The tag is preferably located at either the N-terminus or the C-terminus of the encoded polypeptide. The tag may be an affinity tag for use in e.g. protein purification. Examples of affinity tags include FLAG-tags, polyhistidine-tags (His-tags), HA-tags, SUMO tags, Strep-tags, S-tags and Myc-tags. In a preferred embodiment the affinity tag is a His-tag. SUMO tags are able to play an additional role in expression of polypeptides, in that they can function not only as an affinity tag, but can also improve the stability, solubility and/or folding of certain proteins. The nucleic acid molecule of the invention may therefore contain a SUMO tag for these purposes in addition to an affinity tag for protein purification. For example, the nucleic acid molecule of the invention may comprise or have the nucleotide sequence of SEQ ID NO: 24, which encodes the polypeptide of SEQ ID NO. 25 and is codon-optimised for expression in E. coli. The polypeptide of SEQ ID NO. 25 consists of the polypeptide of SEQ ID NO. 2 with an N-terminal His-tag immediately downstream of the initiating methionine residue, and a SUMO-tag immediately downstream of the His-tag.

Parts of such nucleotide sequences are also encompassed, as are variants of those parts which have at least 90% sequence identity thereto (and particularly variants of SEQ ID NOs. 13 and 14, 15 and 16, 17 and 18, and 19 and 20). In all embodiments, the nucleic acid molecule comprising the nucleotide sequence encodes a thermostable polypeptide having cellulase activity.

Further, in a second aspect, the present invention provides a polypeptide having cellulase activity and which is thermostable, wherein said polypeptide comprises or has;
  (i) an amino acid sequence as set forth in SEQ ID NO. 2, or as set forth in SEQ ID NO. 8;
  (ii) an amino acid sequence with at least 80% identity to the amino acid sequence of (i);
  (iii) part of an amino acid sequence of (i); or
  (iv) part of an amino acid sequence of (ii) having at least 90% identity to an amino acid sequence of SEQ ID NO. 4, SEQ ID NO. 6, SEQ ID NO. 14, SEQ ID NO. 16, SEQ ID NO. 18 or SEQ ID NO. 20.

Particularly, thermostable polypeptides having cellulase activity and comprising or having an amino acid sequence as set forth in any one of SEQ ID NOs. 2, 8, 10 or 12, a part thereof or a sequence with at least 80% identity thereto are specifically encompassed.

For instance, as described above, a polypeptide of the invention may comprise a variant of any one of SEQ ID NOs. 2, 8, 10 or 12, which differs from the wild type amino acid sequence by the presence of one or more tag sequences, preferably at either the N-terminus of the C-terminus of the polypeptide. As described above, the tag may be an affinity tag for use in e.g. protein purification, such as for example a FLAG-tag, a His-tag, an HA-tag, a SUMO tag, a Strep-tag, an S-tag and a Myc-tag. Alternatively or additionally, a SUMO tag may be used to improve the stability, solubility and/or folding of the polypeptide. For instance, the polypeptide of the invention may comprise or have the sequence of SEQ ID NO. 25.

Further, the invention provides a thermostable polypeptide having cellulase activity and comprising or having an amino acid sequence with at least 80% identity to the amino acid sequence of SEQ ID NO. 2, wherein a part of said amino acid sequence has at least 90% sequence identity to any one of SEQ ID NO. 4, SEQ ID NO. 6, SEQ ID NO. 14, SEQ ID NO. 16, SEQ ID NO. 18 or SEQ ID NO. 20.

Thus, as discussed above, the invention provides for parts and/or variants of the wild type nucleotide and amino acid sequences (SEQ ID NOs. 1 and 7 and SEQ ID NOs. 2 and 8, respectively). Thus, nucleic acid molecules comprising portions and/or variants of the sequences as set forth in SEQ ID NOs. 1 and 7, which encode a protein with cellulase activity which is thermostable are encompassed by the invention. The terms "portion", "part" and "fragment" are used interchangeably in the application. A portion of an amino acid sequence of the invention may have a truncation at either or both of the N or C termini and may be encoded by a nucleotide sequence which has nucleotide deletions at the 5' and/or 3' ends. Further, a deletion may occur within the amino acid or nucleotide sequence (i.e. an internal deletion). Any number of amino acid residues or nucleotides can be deleted or truncated to result in a portion or part of a sequence of the invention, e.g. one or more residues (at least 1, 5, 10, 20, 30, 40, 50, 100, 200, 300 etc.) can be truncated or deleted as long as the polypeptide comprising a truncated amino acid sequence is functional or as long as the nucleic acid molecule comprising a truncated nucleotide sequence encodes a functional product.

Particularly, the cellulase encoded by SEQ ID NO. 1 (i.e. the cellulase of SEQ ID NO. 2) may be processed and may function as a fragment or portion of the sequence of SEQ ID NO. 2, as discussed briefly above. In this respect, an N-terminal portion of the sequence of SEQ ID NO. 2 may be absent from a functional cellulase of the invention and thus nucleic acid molecules which encode N-terminal truncated proteins of SEQ ID NO. 2 are specifically encompassed by the invention. As discussed below in detail, a nucleic acid comprising a nucleotide encoding an N-terminally truncated portion of SEQ ID NO. 2 may have a single or multiple nucleotide deletions, e.g. at least 1, 2, 3, 4, 5, 10, 20, 30, 40, 50, 60, 70, 80, 90, 100, 110, 120, 130, 140, 150, 200, 300, 400, 500, or 600 nucleotide deletions. Particularly, the nucleotide sequence may have at least 610, 620, 630, 640, 650, 660, 670, 680, 690, 700, 710, 720, 730, 740, 750, 760, 770, 780, 790, 800, 810, 820, 830 or 840 nucleotide deletions at the N-terminus, e.g. more particularly, 693, 694, 695, 696, 697, 698 or 699 or 834, 835, 836, 837, 838 or 839 nucleotide deletions at the N-terminus. Particularly, a nucleic acid molecule comprising a nucleotide sequence encoding an amino acid sequence as set forth in SEQ ID NOs. 4 and 6 or an amino acid sequence with at least 80% identity thereto is encompassed by the invention. Further, a nucleic acid molecule comprising a nucleotide sequence as set forth in SEQ ID NOs. 3 and 5 or a nucleotide sequence with at least 80% identity thereto is encompassed. Further, a polypeptide comprising an amino acid sequence as set forth in SEQ ID NO. 4 or 6 or a sequence with at least 80% identity thereto is also encompassed.

Other parts of the full-length sequences of the invention are also encompassed (and variants thereof), as long as the polypeptides comprising such parts are functional (i.e. have cellulase activity and are thermostable). In this respect, the inventors have identified putative regions within the amino acid sequence of SEQ ID NO. 2 which may contribute to cellulase activity. These regions can be found at amino acid position 40-415 (e.g. 66-385), 588-746 or 866 to 1082 (e.g. 866-1072 or 925-1082) in SEQ ID NO. 2. The amino acid sequence of residues 66-385 of SEQ ID NO. 2 is provided for in SEQ ID NO. 16 (encoded by a nucleotide sequence of SEQ ID NO. 15), of residues 588-746 of SEQ ID NO. 2 is provided for in SEQ ID NO. 18 (encoded by a nucleotide sequence of SEQ ID NO. 17), of residues 866-1072 of SEQ ID NO. 2 is provided for in SEQ ID NO. 14 (encoded by a nucleotide sequence of SEQ ID NO. 13) and of residues 925-1082 of SEQ ID NO. 2 is provided for in SEQ ID NO. 20 (encoded by a nucleotide sequence of SEQ ID NO. 19).

Thus, the invention particularly encompasses a nucleic acid molecule comprising a nucleotide sequence which encodes amino acid residues 40-415 (e.g. 66-385), 588-746 and/or 866 to 1082 (e.g. 866-1072 or 925-1082) of SEQ ID NO. 2, or an amino acid sequence with at least 90% sequence identity thereto, e.g. with at least 91, 92, 93, 94, 95, 96, 97, 98 or 99% sequence identity thereto. Particularly, the nucleic acid molecule of the invention may comprise a nucleotide sequence which encodes one or more of these regions or one or more regions with at least 90% sequence identity thereto (e.g. two, three or four regions). The nucleic acid molecule may therefore comprise a nucleotide sequence encoding amino acid residues 40-415 and 866-1082 of SEQ ID NO. 2; 66-385 and 866-1072 of SEQ ID NO. 2; 66-385 and 925-1082 of SEQ ID NO. 2; 66-385, 588-746 and 925-1082 of SEQ ID NO. 2 or 66-385, 588-746 and 866-1072 of SEQ ID NO. 2 or a region with at least 90% identity thereto. The corresponding encoded polypeptides are also encompassed by the invention.

The portion of SEQ ID NO. 2 comprising residues 66-385, may begin at amino acid residue 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31 or 30 of SEQ ID NO. 2 and may end at amino acid residue 386, 387, 388, 389, 390, 395, 400, 405, 410, 415, 420, 425 or 430, e.g. amino acid residues 60-385, 60-390, 55-390, 55-400, 50-400, 45-405, 45-410, 35-415, 35-420 of SEQ ID NO. 2.

The portion of SEQ ID NO. 2 comprising residues 588-746 may begin at amino acid residue 587, 586, 585, 584, 583, 582, 581, 580, 575, 570, 565, or 560 of SEQ ID NO. 2 and may end at amino acid residue 747, 748, 749, 750, 751, 752, 753, 754, 755, 760, 765 or 770 of SEQ ID NO. 2, e.g. amino acid residues 585-746, 585-750, 580-750, 580-755, 575-755 or 575-760 of SEQ ID NO. 2.

Further, the portion of SEQ ID NO. 2 comprising residues 866-1082 may be from amino acid residues 850-1082, 840-1082, 830-1082, 820-1082, 810-1082 or 800-1082. The portion of SEQ ID NO. 2 comprising residues 866-1082 may alternatively be from amino acid residues 850-1085, 850-1090, 850-1100, 850-1110, 850-1120, 850-1130, 850-1140, 850-1150, 850-1160, 850-1170 or 850-1180. Particularly, the portion of SEQ ID NO. 2 comprising residues 866-1072 may begin at amino acid residue 810, 811, 812, 813, 814, 815, 820, 825, 830 or 835 of SEQ ID NO. 2 and may end at amino acid residue 1083, 1084, 1085, 1086, 1087, 1088, 1089, 1090, 1091 or 1092 of SEQ ID NO. 2. More particularly, the portion of SEQ ID NO. 2 comprising residues 866-1082 may be of amino acid residues 812-1084, 814-1083, or 830-1089 of SEQ ID NO. 2.

Specifically, a portion of SEQ ID NO. 2 comprising amino acid residues 866-1072 or comprising amino acid residues 925-1082 is encompassed. The portion comprising residues 866-1072 of SEQ ID NO. 2 may begin at amino acid residue 865, 864, 863, 862, 861, 860, 859, 858, 857, 856, or 855 of SEQ ID NO. 2 and may end at amino acid residue 1073, 1074, 1075, 1076, 1077, 1078, 1079, 1080, 1081, 1082 or 1083 e.g. amino acid residues 860-1072, 855-1075, 855-1080 of SEQ ID NO. 2. The portion comprising residues 925-1082 of SEQ ID NO. 2 may begin at amino acid residue 924, 923, 922, 921, 920, 919, 918, 917, 916 or 915 of SEQ ID NO. 2 and may end at amino acid residue 1083, 1084, 1085, 1086, 1087, 1088, 1089, 1090, 1091, 1092 or 1093 of SEQ ID NO. 2, e.g. amino acid residues 920-1082, 920-1085, 920-1090, 915-1090 or 915-1092 of SEQ ID NO. 2.

In particular, a portion of SEQ ID NO. 2 of the invention may comprise a region or regions of SEQ ID NO. 2 which are not present in, or do not correspond to a region of, either SEQ ID NO: 2 of U.S. Pat. No. 7,465,571 (SEQ ID NO. 30 of the present application) or SEQ ID NO: 372 of WO 2007/094852 (SEQ ID NO. 31 of the present application). Specifically, a part or portion of SEQ ID NO. 2 according to the present invention, or an amino acid sequence with at least 90% sequence identity to a part or portion of SEQ ID NO. 2, does not include SEQ ID NO. 30 or SEQ ID NO. 31 of the present application.

SEQ ID NO. 31 of the present application has a sequence similar to that of amino acids 1 to 745 of SEQ ID NO. 2 of the present application (equating to a global sequence identity of 52.6%). SEQ ID NO. 30 of the present application has a sequence similar to that of amino acids 51 to 882 of SEQ ID NO. 2 of the present application (equating to a global sequence identity of 62.4%). Thus amino acid residues 883 to 1322 of SEQ ID NO. 2 of the present application are not present in, and do not correspond to a region of, either of the above-mentioned prior art sequences. A portion of SEQ ID NO. 2 of the invention may thus comprise amino acid residues 883 to 1322 of SEQ ID NO. 2. In particular, such a portion may comprise amino acid residues 866 to 1072 or 925 to 1082, as described above.

The nucleic acid molecule of the invention comprising a nucleotide sequence encoding one or more of such portions will encode a functional polypeptide with cellulase activity and which is thermostable as already discussed. The above-discussed regions thus have truncations at both the N and C termini of SEQ ID NO. 2.

The nucleic acid of the invention may therefore include or consist of at least one part (or fragment) of the nucleotide sequence of SEQ ID NO. 1 or at least one part of the nucleotide sequence of SEQ ID NO. 7 (or a variant of specific parts (SEQ ID NOs. 3, 5, 13, 15, 17 or 19) having at least 90% identity to those parts as discussed above), or may encode a polypeptide which comprises (or is) at least one part (or fragment) of the amino acid sequence of SEQ ID NO. 2 or SEQ ID NO. 8 (or a variant of specific parts (SEQ ID NOs. 4, 6, 14, 16, 18 or 20) having at least 90% identity thereto as discussed above). Alternatively viewed, the polypeptide of the invention may include or consist of at least one part or fragment of the amino acid sequence of SEQ ID NO. 2 or SEQ ID NO. 8 or a variant of parts SEQ ID NOs. 4, 6, 14, 16, 18 or 20 having at least 90% amino acid sequence identity thereto.

A "part" of a nucleotide of amino acid sequence of the invention may include or comprise at least 10, 20, 30, 40, 50, 55, 60, 65, 70, 75, 80, 85, 90, 91, 92, 93, 94, 95, 96, 97, 98 or 99% or more contiguous nucleotides or amino acids of the sequence. Exemplary parts or fragment sizes include at least 450, 600, 700, 800, 900, 1000, 1100, 1200, 1300, 1400, 1500, 1600, 1700, 1800, 1900, 2000, 2100 or 2200 nucleotides. Further exemplary parts of fragment sizes include at least 150, 160, 170, 180, 190, 200, 700, 800 or 900 amino acid residues.

Shorter fragments of the nucleotide sequences of the invention can be used as probes, e.g. for PCR or hybridisation protocols. Shorter fragments can be e.g. 10-30, 20-25, nucleotides in length. Such probes are useful in protocols for identifying further nucleic acid molecules/nucleotide sequences which share homology with the nucleic acid molecules of the invention.

The term "nucleic acid molecule" as used herein refers to a polymer of RNA or DNA that is single or double stranded, optionally including synthetic, non-natural or altered nucleotide bases. Examples of such polynucleotides include cDNA, genomic DNA and ds RNA, inter alia. Preferably, the nucleic acid molecule is DNA. Whilst the nucleic acid sequences referred to herein comprise thymidine ("t"), it will be understood that the invention also relates to corresponding sequences wherein thymidine is replaced by uridine ("u").

In addition to the specific native ("wild type") amino acid sequences (SEQ ID NOs. 2, 8, 10 and 12) discussed above, also included are functional variants of these sequences which have at least 80% amino acid identity to the full length wild type sequences. Further, variants of the nucleotide sequences of SEQ ID NOs. 1, 7, 9 and 11 with at least 80% nucleotide identity to those full-length sequences are encompassed. Thus, these variants of the full length wild type sequences may be at least 80% identical to the nucleotide or amino acid sequences as defined above, particularly at least 81, 82, 83, 84, 85, 86, 87, 88, 89, 90, 91, 92, 93, 94, 95, 96, 97, 98 or 99% identical to the indicated nucleotide or amino acid sequences.

When considering the portions or parts of a full length wild type sequence as set out above, it is preferred that such portions or parts have at least 90% sequence identity to the corresponding part of the full length sequence, e.g. at least 91, 92, 93, 94, 95, 96, 97, 98 or 99% identity. Particularly, the present invention encompasses nucleic acid molecules comprising or having at least one nucleotide sequence which is at least 90% identical to a part of SEQ ID NO. 1 as defined in SEQ ID NO. 3, 5, 13, 15, 17 or 19 or which encodes an amino acid sequence which has at least 90% identity to a part of SEQ ID NO. 2 as defined in SEQ ID NOs. 4, 6, 14, 16, 18 or 20. Further, the invention encompasses polypeptides which comprise or have at least one amino acid sequence having at least 90% identity to that of SEQ ID NOs. 4, 6, 14, 16, 18 or 20.

As discussed previously, it is likely that the polypeptides of the invention have particular domains or regions (parts) which are responsible for the cellulase activity. In this regard, it will be appreciated that it is possible for a sequence variant of SEQ ID NOs. 2, 8, 10 or 12 to have a higher level of identity in the parts corresponding to the putative "cellulase activity" domains of the wild type full-length sequences as compared to the level of identity to the wild type proteins seen in other parts of the protein. In this regard, for example, a variant of SEQ ID NO. 2 may have at least 80% sequence identity to the full length sequence of SEQ ID NO. 2 and may also have at least 90% sequence identity to a "cellulase activity" domain of SEQ ID NO. 2 (putative domains for which are set out in SEQ ID NOs. 14, 16, 18 and 20). Thus, polypeptide variants of the invention may have one or more, e.g. two or three, particular regions which share at least 90% sequence identity to the corresponding regions in the full length wild type sequences, but which may across their full length only share at least 80% sequence identity with the full length protein. Nucleotide sequences may similarly have one or more regions (e.g. two or three) which share a higher level of identity with corresponding regions in the full-length nucleotide sequence, than other regions. Thus, nucleotide sequences again may have at least one region which shares at least 90% sequence identity with a corresponding region in the full length wild type nucleotide sequence, although the nucleotide sequence overall may have at least 80% sequence identity to the wild type full length sequence.

Accordingly, in another aspect of the invention, a nucleic acid molecule may comprise a nucleotide sequence which has at least 80% sequence identity to SEQ ID NO. 1, wherein a part of said nucleotide sequence has at least 90% sequence identity to any one of SEQ ID NO. 3, 5, 13, 15, 17 or 19. Alternatively viewed, the nucleic acid molecule may comprise a nucleotide sequence which encodes an amino acid sequence having at least 80% sequence identity to SEQ ID NO. 2 wherein a part of said amino acid sequence has at least 90% sequence identity to SEQ ID NOs. 4, 6, 14, 16, 18 or 20.

Additionally, in this embodiment, the invention provides a nucleic acid molecule which encodes a polypeptide having cellulase activity and which is thermostable, wherein said nucleic acid molecule comprises or has a nucleotide sequence which encodes an amino acid sequence having at least 80% sequence identity to SEQ ID NO. 2, wherein said nucleotide sequence comprises one or more parts (e.g. 2, 3, 4), which each encode an amino acid sequence having at least 90% identity to any one or more of SEQ ID NOs. 14, 16, 18 or 20. For example, the nucleotide sequence may comprise parts which encode an amino acid sequence with at least 90% identity to SEQ ID NO. 14 and an amino acid sequence with at least 90% identity to SEQ ID NO. 16. Alternatively, a nucleic acid molecule may comprise or have a nucleotide sequence with at least 80% identity to SEQ ID NO. 1 wherein said nucleotide sequence comprises one or more parts which have at least 90% identity to any one or more of SEQ ID NOs. 13, 15, 17 or 19.

Nucleotide variants may have 1, 2, 3, 4, or 5 or more nucleotide additions, substitutions, insertions, or deletions. The amino acid variants may comprise a single or multiple amino acid changes e.g. 1, 2, 3, 4 or 5 or more amino acid additions, substitutions, insertions or deletions. Such variants may include natural variants, e.g. different variants which may occur in nature (in the original or in different organisms to those from which the nucleic acids/proteins were originally isolated) and which are thermostable and have cellulase activity. Alternatively, the variants may be synthetic or artificial variants e.g. obtained or derived by modification (e.g. mutation) of the amino acid sequences of the invention (e.g. sequences comprising or having an amino acid sequence of SEQ ID NO. 2 or SEQ ID NO. 8, or a defined portion thereof) or of the nucleotide sequences of the invention (e.g. sequences encoding those amino acid sequences or sequences comprising or having a nucleotide sequence of SEQ ID NO.1 or SEQ ID NO. 7, or a defined portion thereof).

Variants of the naturally occurring amino acid sequences as defined herein can also be generated synthetically, e.g. by using standard molecular biology techniques that are known in the art, for example standard mutagenesis techniques such as site-directed or random mutagenesis (e.g. using gene shuffling or error prone PCR). Such mutagenesis techniques can be used to develop enzymes which have improved or different properties in combination with the cellulase activity.

Derivatives of the amino acid sequences as defined herein may also be used. By derivative is meant an amino acid sequence as described above or a variant thereof which, instead of the naturally occurring amino acid, contains a structural analogue of that amino acid. Derivatization or modification (e.g. labelling, glycosylation, methylation of the amino acids in the polypeptide) may also occur as long as function of the polypeptide is not adversely affected.

By "structural analogue", it is meant a non-standard amino acid. Examples of non-standard or structural analogue amino acids which may be used are D amino acids, amide isosteres (such as N-methyl amide, retro-inverse amide, thioamide, thioester, phosphonate, ketomethylene, hydroxymethylene, fluorovinyl, (E)-vinyl, methyleneamino, methylenethio, or alkane), L-N methylamino acids, D-α methylamino acids, D-N-methylaminoacids.

Particularly, variants may comprise one or more conservative amino acid changes as compared to the wild type sequences.

Sequence identity may be assessed by any convenient method. However, for determining the degree of sequence identity between sequences, computer programs that make multiple alignments of sequences are useful, for instance Clustal W (Thompson et al., (1994) Nucleic Acids Res., 22: 4673-4680). Programs that compare and align pairs of sequences, like ALIGN (Myers et al., (1988) CABIOS, 4:11-17), FASTA (Pearson et al., (1988) PNAS, 85: 2444 2448) and gapped BLAST (Altschul et al., (1997) Nucleic Acids Res., 25: 3389-3402) are also useful for this purpose. Furthermore, the Dali server at the European Bioinformatics institute offers structure-based alignments of protein sequences (Holm (1993) J. Mol. Biol., 233: 123-138; Holm (1995) Trends Biochem. Sci., 20: 478-480; Holm (1998) Nucleic Acid Rs., 26: 316-9).

Multiple sequence alignments and percent identity calculations may be determined using the standard BLAST parameters, (using sequences from all organisms available, matrix Blosum 62, gap costs: existence 11, extension 1). Alternatively, the following program and parameters may be used: Program: Align Plus 4, version 4.10 (Sci Ed Central Clone Manager Professional Suite). DNA comparison: Global comparison, Standard Linear Scoring matrix, Mismatch penalty=2, Open gap penalty=4, Extend gap penalty=1. Amino acid comparison: Global comparison, BLOSUM 62 Scoring matrix.

The terms "polypeptide" and "protein" are used interchangeably herein and include any length of amino acid chain (i.e. any polymer or oligomer of amino acids).

As noted above, the nucleic acid molecules of the invention should encode a functional polypeptide or protein, regardless of whether the nucleotide sequence comprised therein is directed to a full-length wild type sequence of the invention or to a part and/or a variant thereof. A "functional" polypeptide or protein is one which has cellulase activity and which is thermostable. Particularly, a polypeptide of the invention which comprises a part and/or a variant of the amino acid sequences of SEQ ID NOs. 2, 8, 10, or 12 has the same or similar activity to the corresponding full-length wild type polypeptide, or alternatively viewed does not have a substantially decreased activity (e.g. has less than a 5, 10, 15, 20, 25, 30, 35, 40 or 45% decrease in activity as compared to the corresponding full-length wild type sequence).

The term "cellulase activity" as used herein, refers to the ability of a protein or polypeptide to hydrolyse the 1,4-beta-D-glycosidic linkage in cellulase, hemicellulose, lichenin and cereal beta-D-glucans. Cellulase activity can be determined by culturing microorganisms (expressing or potentially expressing a cellulase) on LB agar containing CMC (particularly 0.1% CMC). Cultured colonies are removed from the agar and plates stained using Congo red and de-stained using 3M NaCl. Cellulase activity can be detected by yellow halos around the clone. Alternatively, cellulase activity can be determined using 4-Methylumbelliferyl-β-D-cellobioside (MUC) which is a fluorescent cellulase substrate. Incubation of cellulase with MUC produces fluorescence which can be measured quantitatively.

A polypeptide which has cellulase activity according to the present invention thus refers to a polypeptide which is capable of producing a yellow halo effect when expressed in a microorganism on LB agar containing CMC, using the method as discussed above, and/or is capable of producing fluorescence when incubated with MUC. Particularly, a polypeptide of the invention will be capable of producing at least 2, 2.5, 3, 3.5, or 4 times the level of fluorescence in the MUC assay when compared to a control sample (i.e. without cellulase activity) when measured under the same conditions, e.g. at the same temperature, for the same length of time, and with the same total protein content. When cellulase activity is measured in a cell extract from a cell transfected with a putative cellulase encoding gene, the encoded polypeptide will be considered to have cellulase activity if the level of fluorescence produced is at least 2, 2.5, 3, 3.5 or 4 times greater than the level of fluorescence when compared to an extract from the same cells without transfection with the putative cellulase encoding gene, under the same conditions.

Further, the polypeptides of the invention are "thermostable". The term "thermostable" as used herein means that the polypeptides have cellulase activity at a temperature which is increased above 37° C., particularly a temperature of at least 40, 50, 60, 70 or 80° C. Typically, thermostability may be determined by incubation of the enzyme at an elevated temperature (e.g. of at least 50, 60° C. or higher) for a given time (e.g. one, two or three hours). Residual cellulase activity in the supernatant after centrifugation may be measured. Typically, all non-thermostable enzymes will be denatured and precipitated in the centrifugation step and thus removed from the extract and any detectable residual cellulase activity in the heated extract is indicative of a thermostable cellulase.

Particularly, a thermostable cellulase according to the invention may have cellulase activity as previously defined at a temperature of 60° C., i.e. will be capable of producing a yellow halo in the LB assay with CMC and/or fluorescence in the MUC assay (particularly, fluorescence at least 2 times greater than a control level (e.g. in the same sample lacking a cellulase activity)). It will be appreciated that the cellulase activity possessed by a polypeptide may alter at different temperatures and thus it is possible that a polypeptide of the invention may exhibit a different cellulase activity at a raised temperature e.g. at 60° C., as compared to that exhibited at a temperature of 37° C. Thus, it is possible that the cellulase activity of a polypeptide of the invention may be increased, decreased or even the same as that shown at 37° C. after the same incubation period. A thermostable cellulase preferably will not have a substantially decreased cellulase activity at a temperature greater than 37° C. e.g. 60° C., as compared to its activity at 37° C. and thus preferably will not exhibit a decrease in cellulase activity of more than 5, 10, 15, 20, 25, 30, 35, 40, 45, 50, 55 or 60%.

It will be appreciated that thermostable enzymes (cellulases) will have an optimal temperature for activity and also a maximum tolerated temperature (after which the enzyme will become denatured and cellulase activity will cease or decrease). Generally, the optimal temperature may be close to the maximum tolerated temperature, e.g. less than 10, 5, 4, 3, 2 or 1° C. apart. In the present invention, the enzymes of the invention may have an optimal temperature of at least 50, 55 or 60° C. For example, the cellulases of SEQ ID NOs. 2 and 8 are thermostable at least up to a temperature of 80° C., and the cellulases of SEQ ID NOs. 10 and 12 are thermostable up to a temperature of approximately 60° C.

In a further aspect, the present invention provides a construct e.g. a recombinant construct, comprising a nucleic acid molecule of the invention. Particularly the nucleic acid molecule may be operably linked within said construct to an expression control sequence, which may be heterologous to the nucleic acid molecule i.e. non-native. Such an expression control sequence will typically be a promoter. Accordingly, the construct may comprise a native or non-native promoter (particularly a strong promoter). Optionally, the construct may additionally contain a further one or more genes and/or one or more regulatory sequences (e.g. non-native sequences). The optional one or more genes may be under the control of the same promoter or under the control of a different promoter. It is therefore encompassed in the present invention for a construct to encode more than one cellulase polypeptide of the invention. In this aspect, the construct may comprise two or more nucleic acid sequences of the invention.

The term "operably linked" refers to the association of two or more nucleic acid molecules on a single nucleic acid fragment so that the function of one is affected by the other. For example, a promoter is operably linked with a coding sequence when it is capable of affecting the expression of that coding sequence (i.e. the coding sequence is under the transcriptional control of the promoter). Coding sequences may be operably linked to regulatory sequences in sense or antisense orientation.

The term "regulatory sequences" refers to nucleotide sequences located upstream (5' non-coding sequences), within, or downstream (3' non-coding sequences) of a coding sequence, and which influence transcription, RNA processing or stability, or translation of the associated coding sequence. Regulatory sequences may include promoters, operators, enhancers and translation leader sequences. As used herein, the term "promoter" refers to a nucleotide sequence capable of controlling the expression of a coding sequence or RNA. In general, a coding sequence is located 3' to a promoter sequence. Promoters may be derived in their entirety from a native gene, or be composed of different elements derived from different promoters found in nature, or even comprise synthetic nucleotide segments. It is further recognised that since in most cases the exact boundaries of regulatory sequences have not been completely defined, nucleic acid fragments of different lengths may have identical promoter activity.

A further embodiment of the invention provides a vector comprising a nucleic acid molecule or construct as defined herein.

More particularly, vectors comprising one or more of the nucleic acid molecules of the invention (or construct of the invention) may be constructed. The choice of vector may be dependent on the host microorganism, the method that will be used to transform host cells, the method that is used for protein expression or on another intended use of the vector. The skilled person is well aware of the genetic elements that must be present in a vector in order to successfully transform, select and propagate cells containing a nucleic acid or construct of the invention. The skilled person will also recognise that different independent transformation events will result in different levels and patterns of expression and thus that multiple events may need to be screened in order to obtain cells displaying the desired level of expression. Such screening may be accomplished by Southern analysis of DNA, Northern analysis of mRNA, Western analysis of protein etc.

The invention further provides a microorganism or host which may be any microorganism, e.g. it may be a prokaryote or a eukaryote. If the host microorganism is a prokaryote, it may for instance be a bacterium (that is to say a eubacterium), e.g. *E. coli*, *B. subtilis* or *Clostridia* species. If the host microorganism is a eukaryote, it may for instance be a yeast, e.g. *S. cerevisiae*, or a filamentous fungus. The host microorganism of the invention contains one or more of the nucleic acid molecules, constructs or vectors of the invention. From sequence analysis of the cellulase enzymes found by the inventors, it is hypothesised that their encoding genes may have originated from archaeal sources. Although the present invention extends to Archaea comprising a nucleic acid molecule, construct or vector of the invention, as these are likely to be difficult to culture, it is preferred that other microorganisms e.g. bacteria, yeasts, filamentous fungi or host cells or organisms are transformed to comprise a nucleic acid molecule, construct or vector of the invention. A microorganism or host cell or organism of the present invention is generally genetically manipulated to introduce the expression of a polypeptide of the invention. This can be achieved by introducing one or more copies of a nucleic acid molecule of the invention under the control of a promoter. Thus, genetic material is present in a host organism that is not present in a naturally-occurring organism (exogenous genetic material is present).

In general, the exogenous genetic material is introduced using the process of transformation. Transformation will typically involve a plasmid or other vector, which will also contain a gene to enable identification of successfully transformed microorganisms, e.g. a gene for antibiotic resistance (for example against ampicillin) or some other marker. Other methods for selecting transformants are known to the skilled person and include the use of a light sensitive vector, a lux gene, which causes positive colonies to light up in the dark.

The transformed gene may integrate into a chromosome and single or multiple copies may be transformed and thus integrated. The encoded product may also be displayed on the cell. Further, a cell of the invention may comprise more than one nucleic acid molecule of the invention, wherein the multiple nucleic acid molecules may encode different cellulases of the invention e.g. two, three or more different cellulases of the invention. Particularly, a cell may comprise a nucleic acid molecule comprising or having a nucleotide sequence which encodes an amino acid sequence of SEQ ID NO. 2 (or a variant or part thereof) and a nucleic acid molecule comprising or having a nucleotide sequence which encodes an amino acid sequence of SEQ ID NO. 8 (or a variant or part thereof). Other suitable vehicles for transformation of microorganisms (bacteria) include fosmids, cosmids, BACs and bacteriophage molecules.

Additionally, the invention provides use of at least one polypeptide of the invention for the degradation of any one or more of cellulose, hemicellulose, lichenin and cereal beta-D-glucan or of a material comprising cellulose hemicellulose, lichenin and/or cereal beta-D-glucan. Thus, any material which contains cellulose and/or any one or more of the compounds listed above as a part, constituent or component may be used as substrate for the polypeptides of the invention. In other words, any cellulosic or cellulose-type material may be used, including e.g. lignocellulose or lignocellulosic materials. Thus, as discussed previously, the polypeptide of the invention has cellulase activity and thus can be used to hydrolyse 1,4-beta-D-glycosidic linkages in cellulose, hemicellulose, lichenin and cereal beta-D-glucans or any cellulose-containing material, substance or compound. Any polypeptide of the invention can thus be used to degrade such substances or materials comprising any one or more of such substances, by incubating said polypeptide of the invention with e.g. cellulose, hemicellulose, lichenin and/or cereal beta-D-glucans or a material comprising one or more of cellulose, hemicellulose, lichenin and cereal beta-D-glucans, such as for example lignocellulose or any material with a cellulose or cellulosic component etc. Particularly, two or more polypeptides may be used together to achieve such a degradation, and more particularly, cellulases having an amino acid sequence of SEQ ID NOs. 2 and 8.

Further, in connection with this, the invention provides a method of degrading any one or more of cellulose, hemicellulose, lichenin and cereal beta-D-glucans or a material comprising one or more of cellulose, hemicellulose, lichenin and cereal beta-D-glucans, wherein at least one polypeptide of the invention is incubated with said cellulose, hemicellulose, lichenin and/or cereal beta-D-glucans or a material comprising one or more of cellulose, hemicellulose, lichenin and cereal beta-D-glucans to degrade the cellulose, hemicellulose, lichenin and/or cereal beta-D-glucans. As indicated above, particularly a polypeptide comprising or having an amino acid sequence as set out in SEQ ID NO. 2 or 8 is used in the method and in one embodiment, two or more polypeptides of the invention are used in the method, e.g. polypeptides comprising or having the amino acid sequences as set out in SEQ ID NOs. 2 and 8.

Particularly, any one or more of the polypeptides of the invention may be used for the degradation of lignocelluosic material or biomass and thus may be particularly used in the production of biofuels.

The invention will now be further described with reference to the following non-limiting Examples. It should be understood that these Examples, while indicating embodiments of the invention, are given by way of illustration only. From the above discussion and these Examples, a skilled person can ascertain the essential characteristics of the invention and without departing from the spirit and scope thereof can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims. All documents referred to herein are incorporated by reference.

Figure 1B:
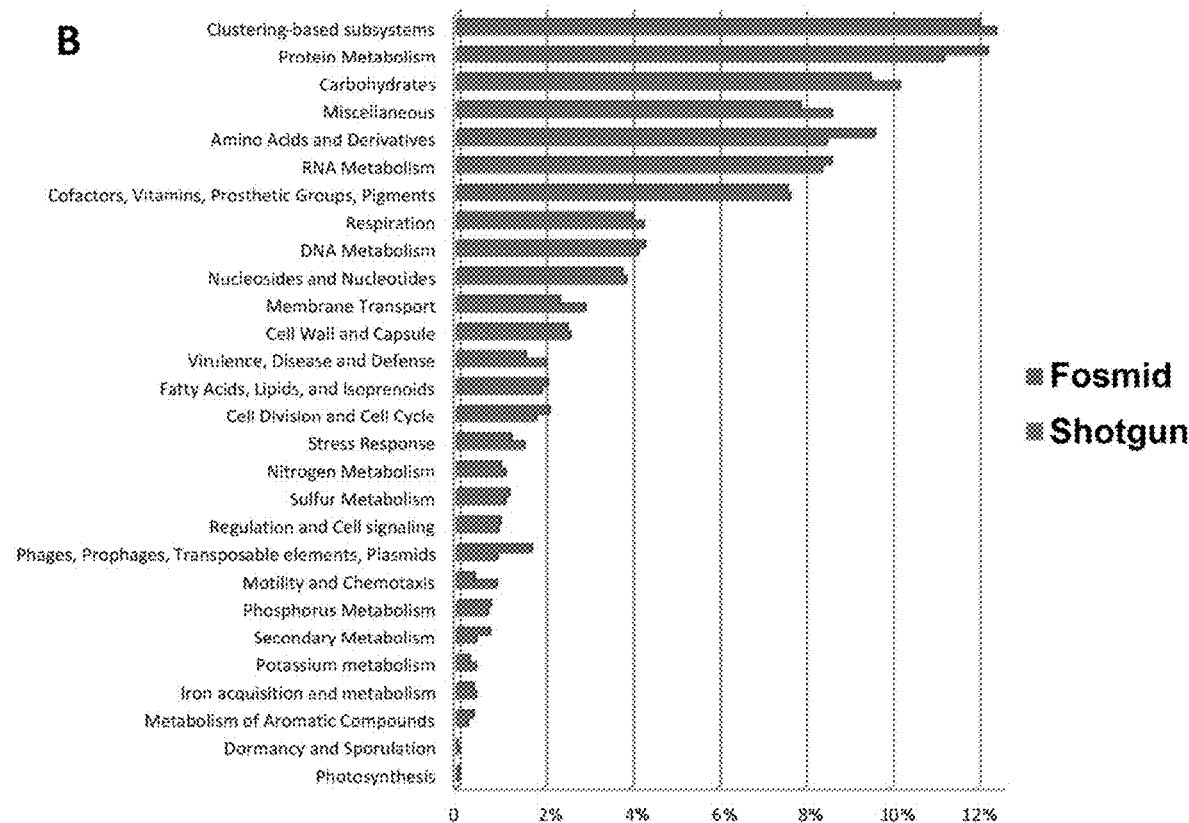

In the Examples, reference is made to the following Figures:

FIGS. 1A and 1B: Relative abundance of shotgun sequences and fosmid metagenomic library sequences at the phylum level (Panel A) and based on functional classification as compared to the SEED database (Panel B). In FIG. 1A, shotgun results are shown as the first bar and fosmid results are shown as the second bar for each phylum. In FIG. 1B, fosmid results are shown as the first bar and shotgun results are shown as the second bar for each functional classification.

Figure 2:
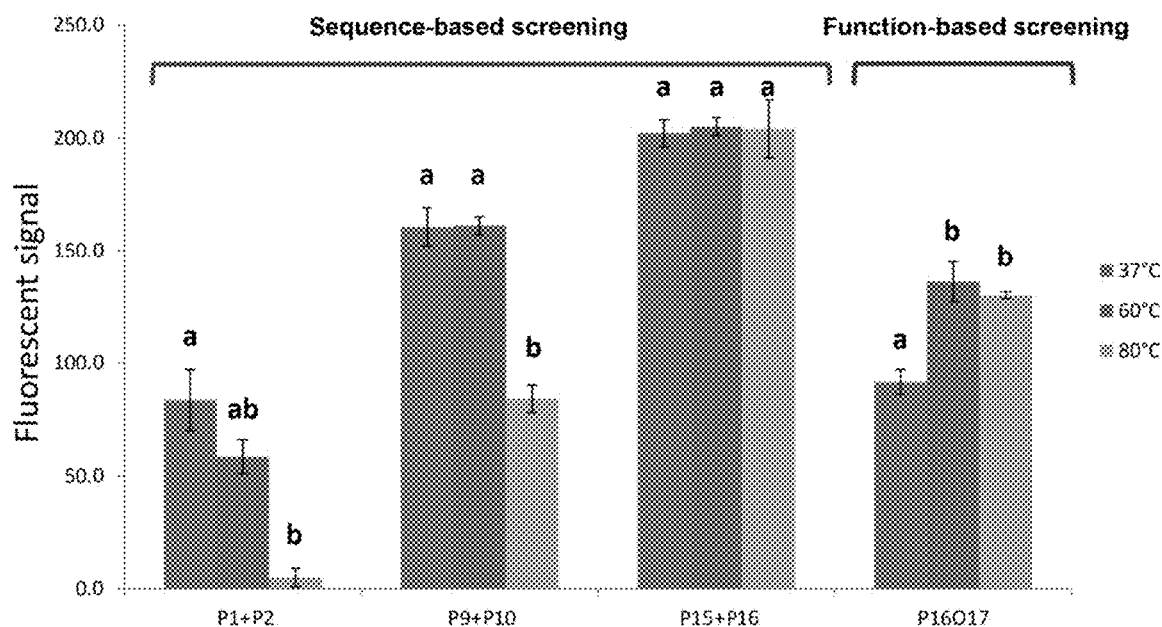

FIG. 2: Quantitative assay of four sub-clones using MUC, in units of fluorescent signal intensity. The supernatants from each of the four sub-clones were incubated at 37° C. (first column), 60° C. (second column) or 80° C. (third column) to test the thermal stability of each respective cellulase. Values for a sub-clone with different superscripts (a, b, ab) were significantly different ($P<0.05$) by one way ANOVA followed by Turkey multiple comparison.

Figure 3:
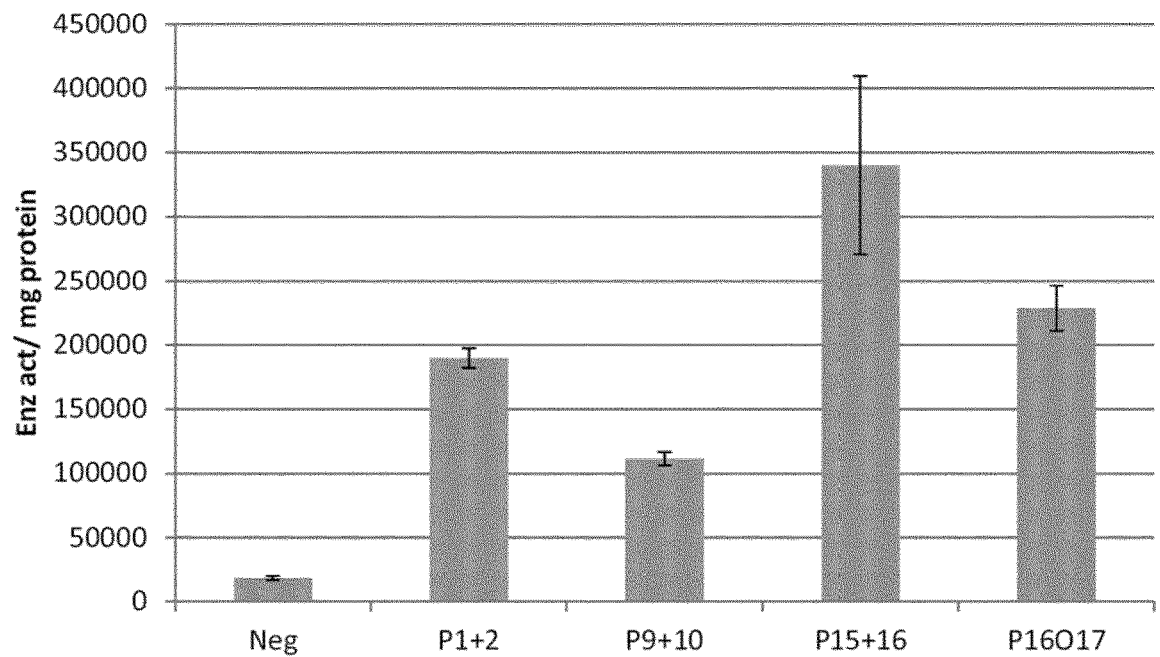

FIG. 3: Activity assay using crude cell extracts, with activity/mg protein plotted for extracts originating from *E. coli* expressing the four cellulase variants, in addition to the *E. coli* negative control.

Figure 4:
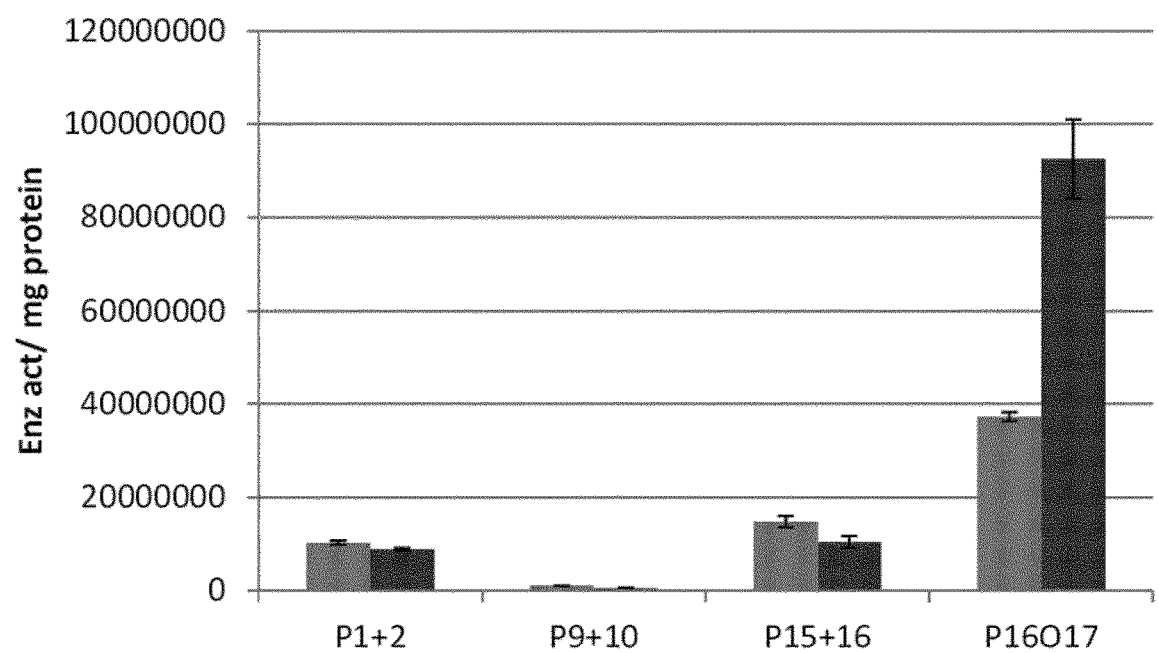

FIG. 4: Activity assay of the Ni-NTA isolated protein, with activity/mg protein plotted for untreated (lighter bars) as well as heat treated (darker bars; 65° C., 20 min) protein samples.

Figure 5:
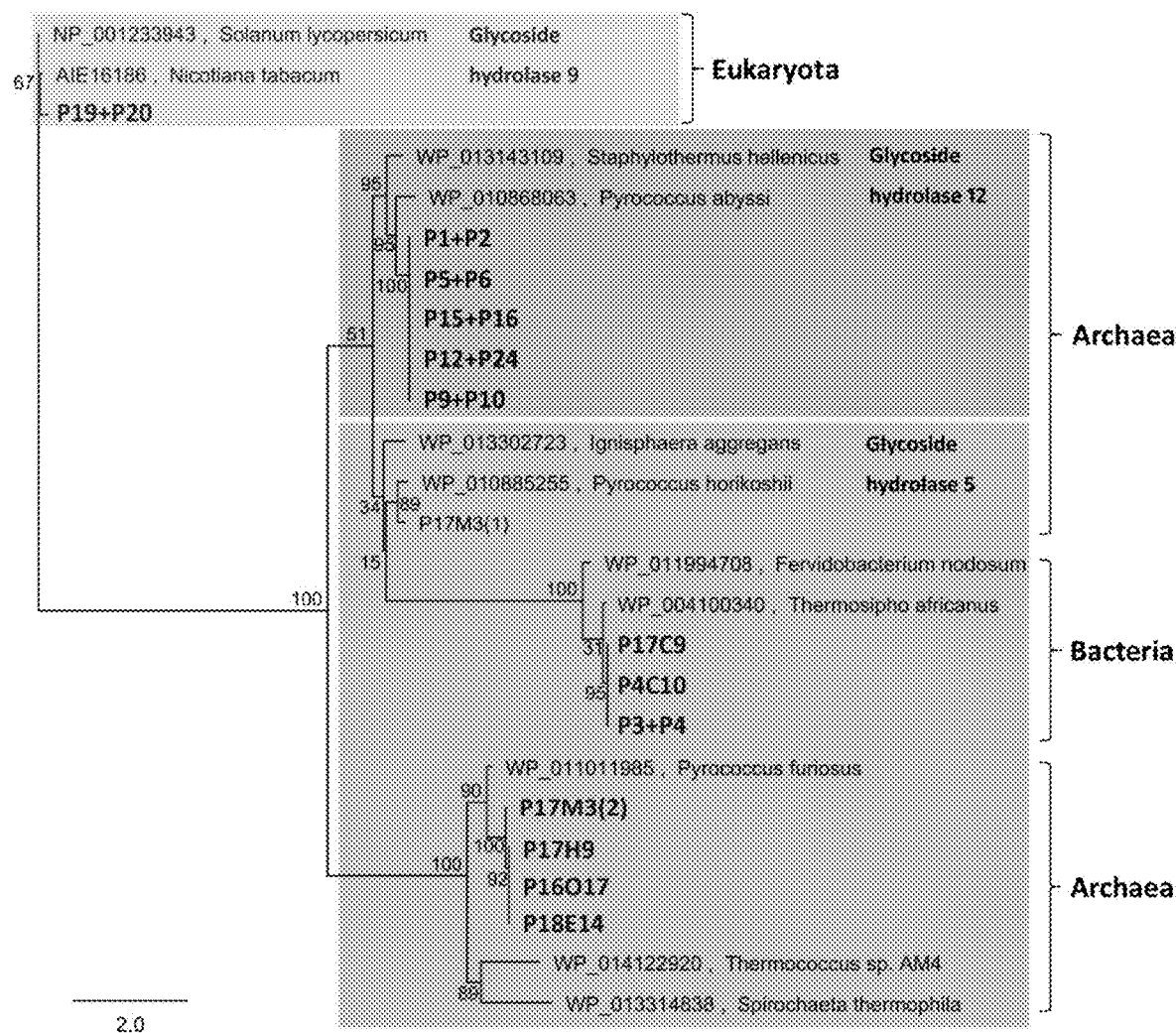

FIG. 5: A maximum likelihood phylogenetic analysis using amino acid sequences of cellulases identified in this study (in bold) and previously described cellulases derived from members of the domains Eukaryota, Archaea and Bacteria. 1000 iterations were conducted for bootstrap support, and bootstrap values are indicated at each node. Cellulases affiliated with glycoside hydrolase 9, glycoside hydrolase 12 and glycoside hydrolase 5 are indicated.

Figure 6:
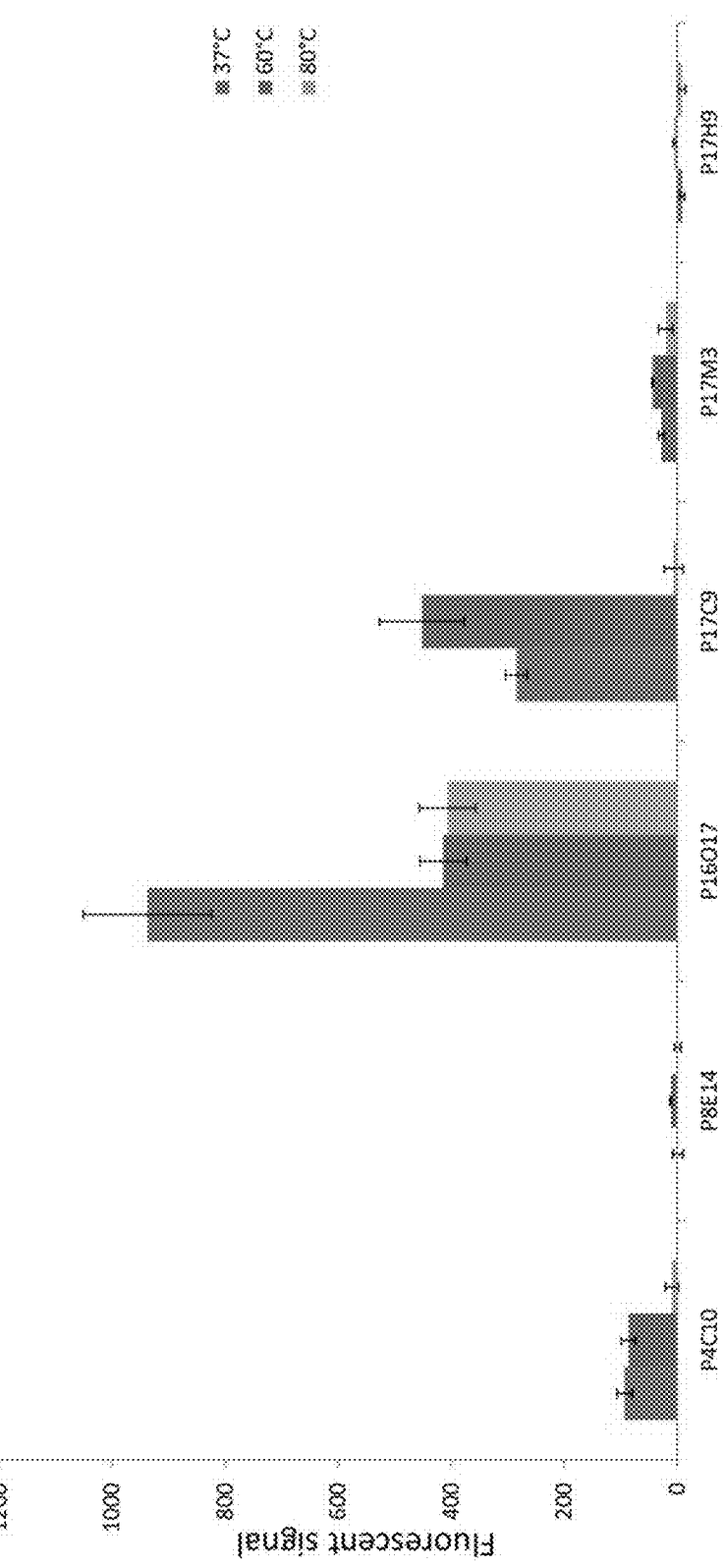

FIG. 6: Quantitative assay of 6 identified plasmid clones using MUC, in units of fluorescent signal intensity. Supernatants of 4 plasmid clones were incubated at 37° C. (first column), 60° C. (second column) or 80° C. (third column) to test the thermal stability of each cellulase.

Figure 7:
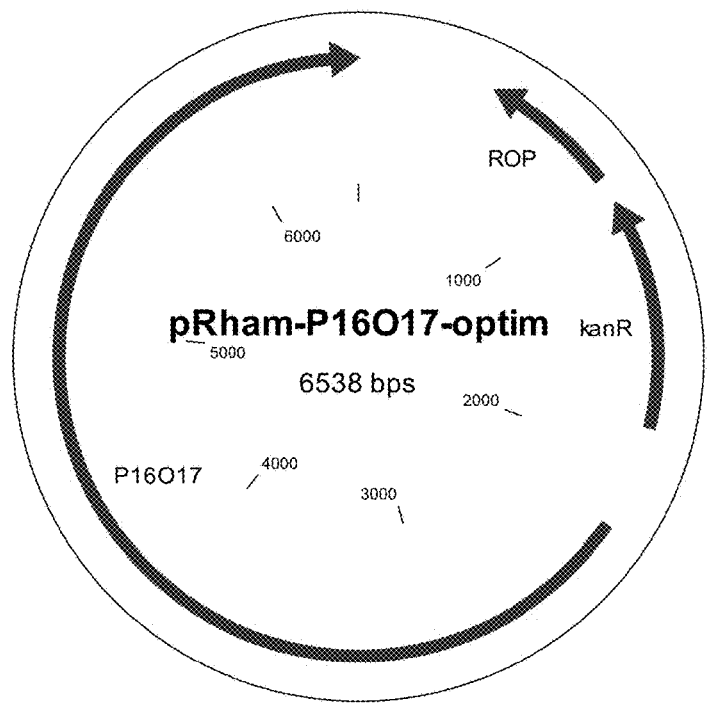

FIG. 7: Schematic representation of expression plasmid pRham-P16O17-optim for expression of the codon optimized P16O17 gene. kanR denotes a kanamycin resistance gene; ROP is the "repressor of primer" gene which ensures plasmid copy number remains low. P16O17 is encoded with an N-terminal His-tag (SEQ ID NOs. 26 and 27) followed immediately by a SUMO (Small Ubiquitin-like Modifier) tag (SEQ ID NOs. 28 and 29). The tag locations are not shown in the figure.

Figure 8:
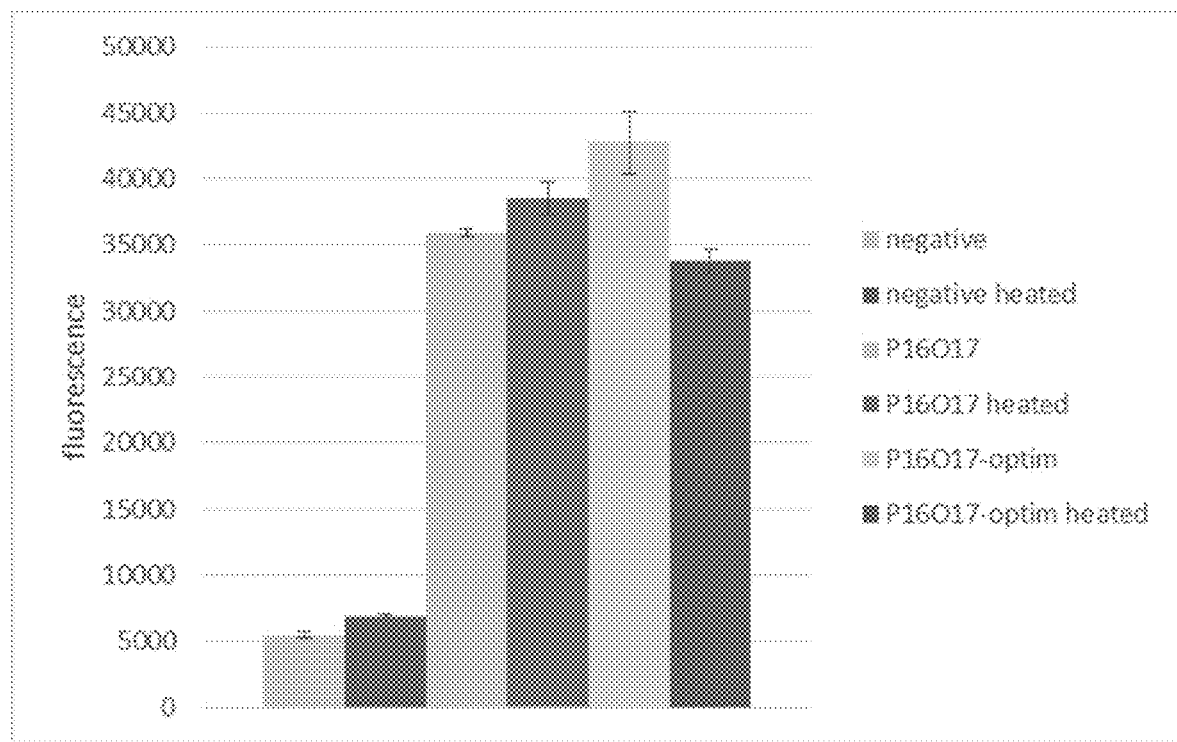

FIG. 8: Cellulase activity measured by 4-MUC assay in crude cell extracts (CCEs). Fluorescence is given in arbitrary units. For the avoidance of doubt, the order of CCEs as listed from top to bottom in the figure legend corresponds to their order from left to right on the graph. Error bars indicate standard deviations from four replicate measurements.

Figure 9:
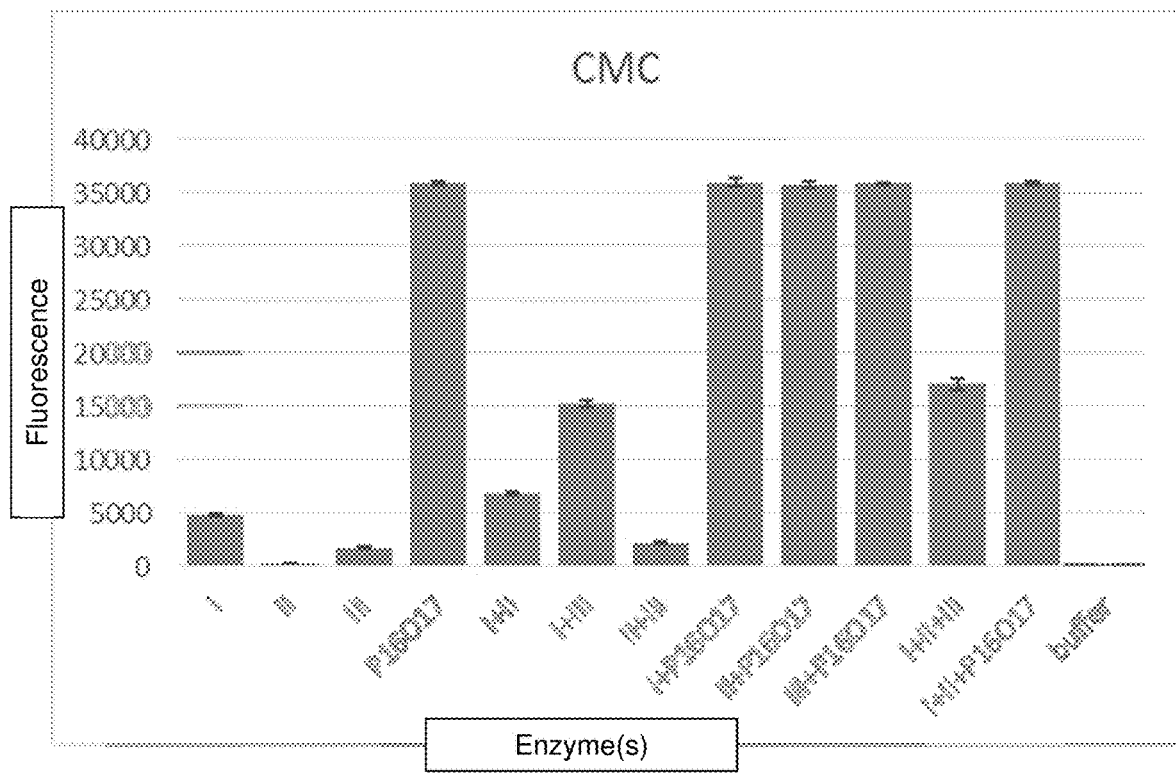

FIG. 9: Activities of enzyme(s) on the cellulase substrate CMC, detected as fluorescence (measured in arbitrary units) using the Amplex UltraRed assay. Error bars indicate standard deviations from three replicate measurements.

Figure 10:
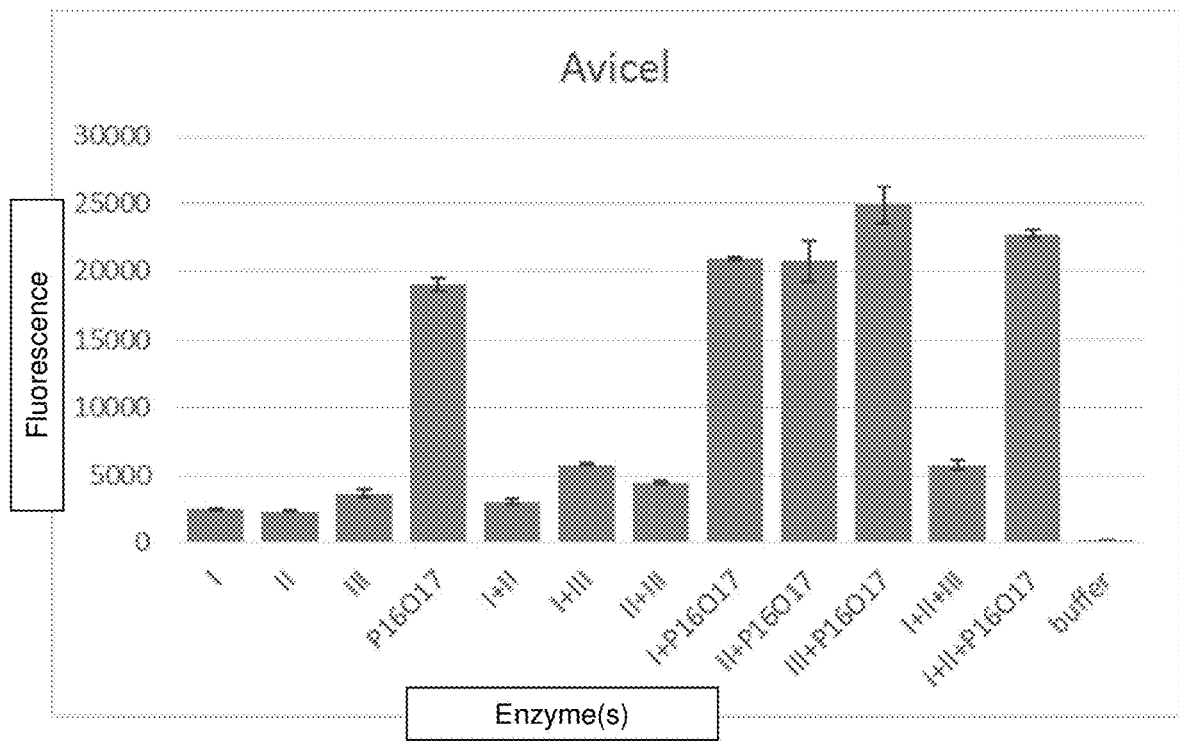

FIG. 10: Activities of enzyme(s) on the cellulase substrate Avicel, detected as fluorescence (measured in arbitrary units) by the Amplex UltraRed assay. Error bars indicate standard deviations from three replicate measurements.

Figure 11:
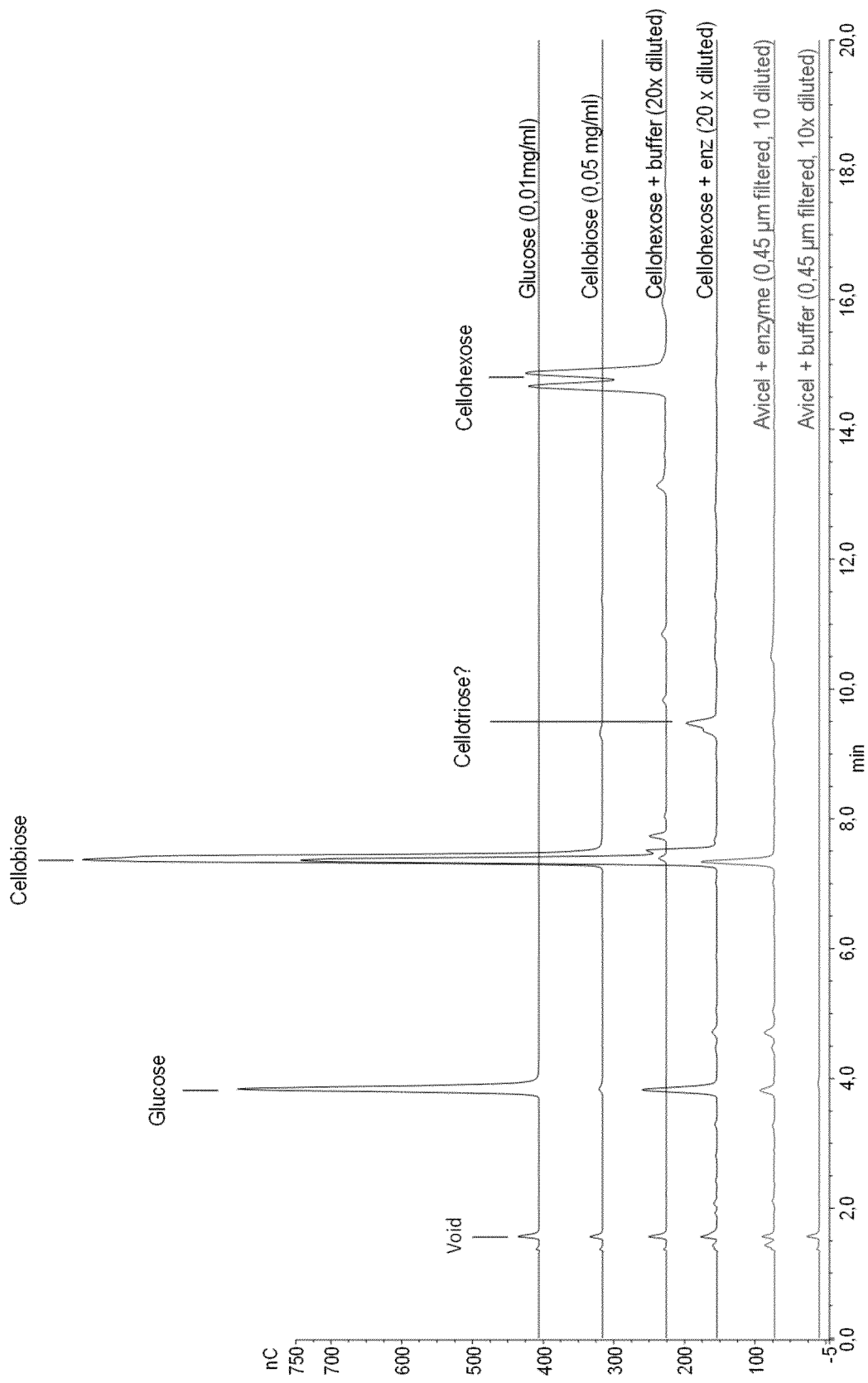

FIG. 11: Results from HPAEC-PAD analysis of products of degradation of cellohexose and Avicel by P16O17. "Enz"=P16O17 enzyme (in the form of CCE); buffer=50 mM potassium acetate, pH 5.5 as negative control. Product peaks measured in nanocoulomb (nC).

Figure 12:
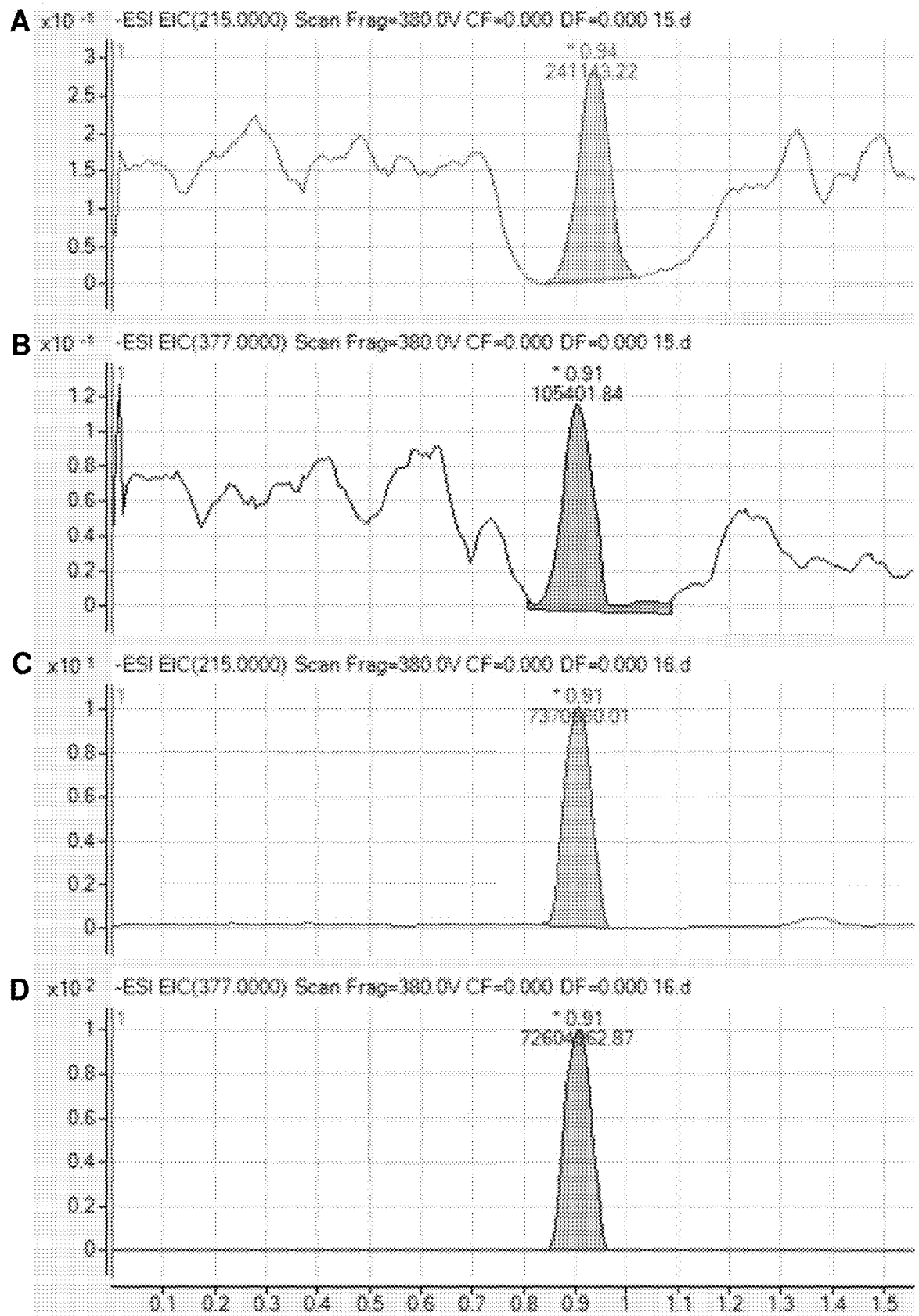

FIG. 12: Relative abundances of [M+Cl]—chlorine adduct anions of glucose (A, C) and cellobiose (B, D) in untreated (A, B) and P16O17-treated Avicel (C, D). The results indicate that both cellobiose and glucose are produced by the enzymatic reaction of P16O17 with Avicel, with cellobiose being the main reaction product and glucose being a by-product.

EXAMPLES

Example 1

Materials and Methods
Oil Reservoir Sampling, DNA Isolation and Handling

Oil reservoir samples were collected and metagenomic DNA isolated in a previous study (Kotlar et al, 2011, Environmental microbiology reports, 3: 674-681). Isolated DNA was used in direct 454 pyrosequencing for metagenomic analysis of the phylogenetic and functional diversity of this oil reservoir microbial assemblage. For preparation of a fosmid library, DNA was amplified using Phi29 polymerase (WGA; Qiagen REPL midi kit) in individual reactions of 50 µl and pooled after amplification. Two individual rounds of amplification were conducted using DNA from each sample (water and oil phases). The amplified DNA was isolated and purified using Qiagen QIAamp DNA mini kit using the manufacturers protocol and used in fosmid library construction using the Epicentre pCC1FOS system. The 11,520 clones of the resulting fosmid library were arrayed in 30×384-well microtiter plates.

Extraction of Fosmid DNA from the Fosmid Library

Each plate of the 384-well formatted *E. coli* metagenomic library was used to inoculate a deep-well 384-well plate containing 170 μl per well of LB broth containing 12.5 g/ml chloramphenicol and 0.01% (w/v) arabinose for plasmid copy-number induction. After 24 hours of growth at 37° C. while shaking at 200 rpm, the clones of every two deep 384-well plates were pooled into a single 250 ml centrifuge tube, and the pooled fosmid DNAs were extracted using a QIAGEN Large-Construct Kit, resulting in 15 separate samples (i.e., two 384-well plates per pool). These fosmid DNAs were then incubated with Plasmid-Safe™ ATP-Dependent DNase (Epicentre) to reduce chromosomal contamination.

Sequencing of the Fosmid Library

Each pooled fosmid DNA prep was used as a template in a Nextera DNA Sample Prep Kit reaction (Illumina, San Diego, Calif.), and a unique set of barcodes was used for each pooled library plate. Then the fragmented DNA was purified using a DNA Clean and Concentrator Kit (Zymo Research, Orange, Calif.) and further used for an amplification reaction according to standard Illumina protocols. The amplified library was then purified using a Size-Select IT kit (Omega Biotek, Norcross, Ga.) to isolate the desired DNA size fraction (~500 bp on average). The purified, bar-coded DNA fragments were quantified using a Qubit fluorimeter followed by pooling at equimolar concentrations and denaturing using 0.1 N NaOH. Finally, the pooled fosmid DNAs were used for an Illumina HiSeq sequencing run with a 2×100 bp paired end sequencing kit (Illumina, San Diego, Calif.).

Bioinformatic Analysis of the Fosmid Library Sequences

The raw sequences generated by each HiSeq run were imported into the CLC Genomics Workbench, and trimmed at a stringency of 0.01 (equivalent to Q score of >40). Trimmed sequences were assembled de novo using the CLC Genomics Workbench (Qiagen, Cambridge, Mass.) to generate a set of contigs per each fosmid pool. ORF prediction was then performed using "ORF finder by six-reading-frame" on Camera Portal 2.0. The predicted ORFs were used for a batch BLASTp against the CAZy database using the tool dbCAN for identification of carbohydrate-degrading enzymes as well as lipases/esterases. In addition, all raw sequence reads recovered from the fosmid library were also exported to MG-RAST to profile microbial diversity and abundance based on phylogeny and function. In order to compare microbial diversity present within the fosmid library (plate 3, 4, 9, 10, 13, 14, 17 and 18) to that of shotgun sequences from the same sample (Well II), trimmed sequence reads from direct 454 pyrosequencing were also uploaded to MG-RAST for analysis.

Functional Screening of the Fosmid Library for Carbohydrate-Degrading Activity

Assays for five different hydrolase enzymatic assays were conducted with five substrates to functionally screen the library. In each assay, the *E. coli* fosmid clones were grown overnight at 37° C. in 96-well plates with each well containing 200 μl of LB broth including 12.5 μg/ml of chloramphenicol, while shaking at 200 rpm. After overnight growth, the *E. coli* cultures were inoculated onto the respective agar medium that included 0.01% arabinose to induce plasmid copy-number using a pin replicator. Cellulase and xylanase activities were screened using LB agar containing 0.1% CMC and 0.1% xylan, respectively. The amylase assay medium was comprised of 1% tryptone, 0.25% yeast extract, 0.5% $K_2HPO_4$, 0.3% starch and 1.5% agar. The protease assay utilized 2% skim milk, 0.5% yeast extract, 0.08% sodium citrate dehydrate and 1.5% agar. LB agar with 1% tributyrin was used to detect the activity of esterases/lipases. After 37° C. incubation overnight, all agar plates except starch agar plates were incubated at 60° C. overnight again and further fumigated with chloroform for 1 hour to lyse *E. coli* cells. Halos of clones expressing proteases or esterases/lipases could be directly observed. For the three other enzymatic assays, colonies were first removed using 95% ethanol and $dH_2O$. Then CMC and xylan agar plates were stained using 1% Congo red for 15 min and de-stained using 3M NaCl. Clones with cellulase activity could be identified from the yellow halos around the clone. For the cell lysis step, starch agar plates were fumigated for 1 hour with chloroform at room temperature. Then an iodine solution (0.3% iodine and 0.6% potassium iodine) was used to stain starch agar plates. After 15 min staining, clones showing obvious halos were identified as amylase-positive clones. The positive clones were re-streaked from original wells onto agar plates with their respective substrates, and tested for validation. Only clones that were validated as positive upon re-testing were selected for further analyses.

Sequencing Fosmid Clones that Express Cellulase Activity

Fosmid clones with reproducible cellulase activity were selected for next-generation sequencing. Fosmid clones were inoculated into 500 ml LB broth with 12.5 μg/ml chloramphenicol and 0.01% arabinose for plasmid copy-number induction. After incubation overnight at 37° C., each fosmid clone DNA was separately extracted using the Large-Construct DNA isolation kit (Qiagen). A Nextera DNA Sample Prep Kit (Illumina, San Diego, Calif.) was employed for preparation of bar-coded fosmid DNA clone sub-libraries, with each clone separately bar-coded, purified and quantified as described above. The pooled fosmid clone DNAs were then sequenced using an Illumina MiSeq with a 2×300 bp paired-end sequencing kit (Illumina, San Diego, Calif.). After sequencing, the clone sequences were trimmed, assembled de novo and ORFs were predicted using the CLC Genomics Workbench. Cellulase ORFs of each clone were annotated by a BLASTp search.

Sub-Cloning of Cellulase Genes

Predicted cellulase encoding ORFs from six clones expressing cellulase activity along with complete or nearly complete cellulase gene ORFs identified from pooled library sequencing were selected for sub-cloning. Each respective ORF was PCR amplified and sub-cloned into the Expresso Rhamnose SUMO sub-cloning system (Lucigen, Middleton, Wis.) and introduced into *E. coli* 10G by electroporation. Sub-clones able to express cellulase were selected after growing on CMC agar and staining (1% Congo red, 15 min).

Thermal Stability Test of Sub-Clones with Cellulase Activity

Two methods were used to evaluate the thermal stability of sub-clones expressing cellulase activity. A broth culture of each clone (0.01% arabinose and 12.5 μg/ml Chloramphenicol, 37° C. overnight) was collected and heated at a series of temperatures (37° C., 60° C., 70° C. and 80° C.). Different incubation times (1 h, 2 h, 3 h and 6 h) at each temperature were applied. In the first method, supernatants of cell lysates (using chloroform) of clones were heated and spotted onto CMC agar plate, and those with yellow halos were recorded. The second method utilized 4-Methylumbelliferyl-β-D-cellobioside (MUC), a fluorescent cellulase substrate, to quantify cellulase thermal stability (25). Equal volumes of 100 μM MUC was added into heated broth culture of sub-clones in a 96-well plate followed by incubation at 37° C. overnight. Next day, the fluorescence of each well was monitored using an excitation at 375 nm and emission of 445 nm with a BioTek Cytation 3 µlate reader (Thermo Fisher Scientific Inc.).

Purification of Active Cellulases from Sub-Clones Using SDS-PAGE

For production of cellulase enzymes the four *E. coli* 10G strains harbouring the sub-cloned genes of interest, along with a negative control *E. coli* 10G, were cultivated in 1000 mL batches. A 5 mL LB culture containing 0.5% glucose and 30 µg/mL kanamycin (except for the negative control) was used as inoculum for 1000 ml LB-kanamycin media, and the cultures were incubated at 37° C. until the OD600 was 0.3-0.5 (3 hours). Cultures were then induced using 0.2% rhamnose (final concentration) and cultivated for another 9.5 hours. Crude cell extracts were prepared by sonication in 5-10 mL buffer (50 mM $KPO_4$, pH5.5) for 7 minutes (50% duty cycle and output control 4) followed by centrifugation at 20,000×g for 30 minutes at 4° C. Isolated extracts were used in heat stability analysis (extract incubation at 70° C. for 3 hours), activity assay (as described above) and used for isolation of the enzymes by Ni-NTA affinity chromatography. For enzyme purification, 450 µl of sterile filtered (0.2 µm) cell extracts were incubated with 1 ml Ni-NTA agarose (equilibrated with native binding buffer; 50 mM $NaH_2PO_4$ buffer (pH 8.0) with 0.5 M NaCl, 10 mM imidazole and 1 mM DTT) for 60 minutes at RT in a Rotamixer. Agarose beads were washed in native wash buffer (50 mM $NaH_2PO_4$ buffer (pH8.0) with 0.5 M NaCl, 20 mM imidazole and 1 mM DTT), re-suspended in 2 ml of the same buffer and applied in a plastic column. The beads were washed three times with 5 ml wash buffer and the bound proteins thereafter eluted using elution buffer (50 mM $NaH_2PO_4$ buffer (pH8.0) with 0.5 M NaCl, and 1 mM DTT) with increasing concentrations of imidazole (100, 150, 200, 250 and 500 mM) in 1 ml fractions. Isolated proteins were subjected to heat incubation (65° C. for 20 minutes), and used in a cellulase activity assay.

Results

Functional and Phylogenetic Classification of Shotgun and Fosmid Metagenomic Sequences Metagenomic sequences from both pooled fosmid and direct shotgun sequencing of an oil reservoir were uploaded into MG-RAST. A series of metagenomic analysis tools in MG-RAST were applied to compare the functional and phylogenetic composition of the two sequence databases. In both shotgun sequences and fosmid library sequences there was a very high abundance of genes derived from the domain Archaea (E value<$10^{-5}$), followed by hits to the domain Bacteria, and with very few hits against viruses or Eukaryotes. At the phylum level, *Euryarchaeota* and *Proteobacteria* were found to be the most abundant in both fosmid and shotgun databases (FIG. 1A). However, approximately 20% of sequence reads in both databases were allocated to the category "unassigned", indicating that the oil reservoir harboured a large number of unknown microbial taxa (FIG. 1A). In contrast, two bacterial phyla had apparent differences in relative abundance in the two databases, with taxa affiliated with the phylum *Proteobacteria* found more frequently in the shotgun database, and taxa affiliated with the *Bacteroidetes* found more frequently in the fosmid library (FIG. 1A).

In addition to a phylogenetic analysis, a functional classification indicated that the fosmid and shotgun sequences had a similar distribution of functional category abundances (FIG. 1B). The category "Carbohydrate", including many carbohydrate-degrading enzymes, was the third most abundant (FIG. 1B), and indicated that many carbohydrate-degrading enzymes were encoded within the oil reservoir metagenome in both databases.

Identification of Carbohydrate-Degrading Enzymes by Sequence-Based Screening

The Illumina HiSeq sequencing of the fosmid library generated 40.1 Gbp of sequence reads; after trimming, we obtained 37.0 Gbp of quality sequence with an average read length of 92 bp. These sequences were assembled de novo yielding 697,947 contigs, with an average coverage for these contigs larger than 1 kb ranging from 3.4× to 112.5×. The ORFs predicted from these contigs were queried against the CAZy database using a local BLASTp search, leading to the discovery of 29,764 ORFs with significant BLAST hits (E-value<$10^{-5}$). These ORFs were derived from 28,913 contigs and included six CAZy families including auxiliary activities (AA), carbohydrate-binding modules (CBM), carbohydrate esterases (CE), glycoside hydrolases (GH), glycosyltransferases (GT) and polysaccharide lyases (PL). Based on the results of a local BLASTp against the CAZy database, we obtained 101 significant hits for cellulases, 21 hits for xylanases, 174 hits for amylases, 39 hits for proteinases/peptidases and 102 hits for esterases/lipases. All cellulase, xylanase and amylase hits were described as members of the GH group.

Identification of Carbohydrate-Degrading Enzymes by Function-Based Screening

For each of the targeted CAZymes we discovered a greater number of enzymes via sequence-based compared to function-based screening (Table 1). For cellulases, we obtained 6 validated hits from functional screening (0.052% hit frequency), whereas 101 were obtained from sequence-based screening (0.88% hit frequency). We found 2 hits from the xylanase functional assay (0.017% hit frequency) and 21 by sequence-based screening (0.18% hit frequency). We found 85 hits from the amylase functional assay (0.74% hit frequency), with 174 hits by sequence-based screening (1.51% hit frequency). We found 33 hits from the protease functional assay (0.29% hit frequency) and 39 hits by sequence-based screening (0.34% hit frequency). Lastly, 9 hits from the esterase/lipase functional assay were identified (0.078% hit frequency) and 102 hits by sequence-based screening (0.89% hit frequency). This suggested that many clones identified from sequence-based screening were not expressed or active in an *E. coli* heterologous host.

Among the different CAZy classes, we selected cellulases for further characterization due to their potential industrial applications. All six clones that expressed a cellulase were tested for their thermal stability. Three clones gave obvious halos on CMC agar assays after the clone supernatants had been incubated at elevated temperatures. Among them, the clone P16O17 (expressing SEQ ID NO. 2) showed halos for all temperatures (37° C., 60° C., 70° C. and 80° C.) and at 1, 2, and 3 hours of incubation (Table 1). In contrast, halos of the P4C10 supernatant heated at 80° C. (1, 2 and 3 hours) could not be detected, and P17M3 did not have clear halos after 80° C. incubation for 3 hours (Table 2). The cellulase activity expressed by P16O17 (SEQ ID NO. 2) was observed to be the most thermostable and the most efficient at cellulose degradation as revealed by its large halo sizes. The same clone P16O17 also demonstrated cellulase activity in the quantitative assay using MUC (FIG. 6). Interestingly, the supernatant of clone P17C9 did not produce any observable halos in any condition, which was inconsistent with the results obtained on CMC agar where clone P17C9 produced the second strongest halo. This might indicate that the cellulase expressed by clone P17C9 is not secreted into the supernatant and may be intracellular or membrane-associated.

The thermostability of each expressed cellulase was also evaluated in the quantitative MUC assay. The supernatant of each respective clone was heated at 37° C., 60° C. or 80° C. for 3 or 6 hours, and then incubated with the MUC substrate. Clones P4C10, P16O17, P17C9 and P17M3 showed a strong fluorescent signal in the MUC assay (FIG. 6). The fluorescent signal of P16O17 was still the highest among all clones, but this signal was reduced when the temperature was increased to 60° C. or 80° C., suggesting a loss of enzyme activity at higher temperatures (FIG. 6). Interestingly, the broth culture of clone P17C9 heated at 60° C. showed a significantly higher fluorescent signal than at 37° C. or 80° C. (FIG. 6), suggesting that the cellulase expressed by clone P17C9 has a temperature optimum around 60° C. The cellulose-degrading activities of clones P4C10 and P17M3 were relatively weak as determined in the MUC assay (FIG. 6). The fluorescent signal of clone P4C10 gradually reduced when temperature increased, whereas that of clone P17M3 had no obvious difference between three temperatures (FIG. 6). The cellulase activities from these clones identified by functional screening were observed to be distinct in terms of their thermostability, and the differences in activities observed probably reflected changes in their protein structure and activity at different temperatures.

TABLE 1

Number of positive CAZyme hits from the oil reservoir metagenomic library identified from either functional screening, using specific substrates, or by sequence-based screening, using BLAST searches against a local CAZy database.

| CAZyme | Functional Screening | Sequence-based screening |
|---|---|---|
| Cellulase | 6 | 101 |
| Xylanase | 2 | 21 |
| Amylase | 85 | 174 |
| Protease | 33 | 39 |
| Esterase/Lipase | 9 | 102 | archaeon *Pyrococcus horikoshii* at the N-terminus and 82.7% amino acid identity to the endo-1,4-beta-glucanase b of the archaeon *Pyrococcus furiosus* DSM 3638 at the C-terminus. However, from Blast searches, overall amino acid identities of from 17-23% are seen between the cellulase of P16O17 (SEQ ID NO. 2) and other known cellulases. In the case of clone P17M3, there were two predicted overlapping cellulase ORFs that had 82.7% amino acid identity to the endo-1,4-beta-glucanase of the archaeon *Pyrococcus furiosus* and the endocellulase of archaeon *Pyrococcus horikoshii*, respectively. Clone P4C10 contains a predicted cellulase that is identical to that of cellulase predicted from clone P17C9, which have 99.7% amino acid identity to the endoglucanase of the bacterium *Thermosipho africanus*.

Despite a large number of cellulase ORFs discovered from sequencing the pooled fosmid DNA library (n=101), there were only 7 complete or near-complete ORFs identified. This is likely due to the use of shorter Illumina HiSeq read lengths and the large number of fosmids in each pool, reducing the coverage per clone. Five of the ORFs identified from this search, from the pooled fosmid clones in plates 1 and 2 (P1+P2, contig 4468.4), plates 5 and 6 (P5+P6, contig 43387.3) plates 9 and 10 (P9+P10, contig 1829.4), plates 12 and 24 (P12+P24, contig 94750.15) and from plates 15 and 16 (P15+P16, contig 25805.3) had an identical DNA sequence with varied length and 70.6% amino acid identity to the endoglucanase of *Pyrococcus abyssi* GE5 (NP_126623). Interestingly, the predicted cellulase ORF from plates 19 and 20 (P19+P20, contig 79977.13) had 85.3% amino acid identity to the endo-1,4-beta-glucanase of a tomato plant (Solanum lycopersicum).Since it is highly unlikely that a relative of a tomato plant is present in the oil reservoir, this perhaps represents a case of lateral transfer. All of these predicted ORFs except P19+P20 were successfully amplified from pooled fosmid DNA. Only one sequence from a predicted cellulase ORF in plates 3 and 4 (P3+P4, contig 223.1) corresponded to the same sequence identified from a fosmid clone (P4C10) expressing a cellulase activity, and in this case we used the fosmid DNA as template for the PCR. The cellulase from the P15+16 contig is set out in SEQ ID NO. 8, the cellulase from the P1+2

TABLE 2

Halos produced by supernatants of 6 clones with cellulase activity in different conditions

| 37 C. | 04B/B5 | | | 08B/C7 | | | 16A/H9 | | | 17A/B5 | | | 17A/G2 | | | 17C/D5 | | |
|---|---|---|---|---|---|---|---|---|---|---|---|---|---|---|---|---|---|---|
| incubation | 60 | 70 | 80 | 60 | 70 | 80 | 60 | 70 | 80 | 60 | 70 | 80 | 60 | 70 | 80 | 60 | 70 | 80 |
| 0 hour | | Y | | | | | | Y | | | | | | Y | | | | |
| 1 hour | Y | Y | | | | | Y | Y | Y | | | | Y | Y | Y | | | |
| 2 hour | Y | Y | | | | | Y | Y | Y | | | | Y | Y | Y | | | |
| 3 hour | Y | Y | | | | | Y | Y | Y | | | | Y | Y | | | | |

"Y" indicates halo was clearly observed.

Sequence Analysis of Cellulase ORFs Identified from Both Sequence-Based and Function-Based Screening The six cellulase positive fosmid clones identified by functional screening were used to prepare sub-libraries with Nextera barcodes and pooled together for sequencing using an Illumina MiSeq. The respective fosmid clones were separately analyzed and a set of contigs were obtained for each clone, from which cellulase-encoding ORFs were detected. The predicted cellulase gene sequences from clones P16O17, P8E14 and P17H9 are identical and exhibit 88.1% amino acid identity to the endocellulase of the contig is set out in SEQ ID NO. 10 and the cellulase from the P9+10 contig is set out in SEQ ID NO. 12.

Thermal Stability of Sub-Cloned Cellulases

Cellulase genes identified from both sequence-based and function-based screening were sub-cloned into the inducible expression Expresso-Rhamnose sub-cloning system. The resulting sub-clones were streaked on CMC agar to assay for cellulase activity. Two of them, from pooled library plates P9+P10 and P15+P16, showed obvious halos after staining. In the MUC quantitative assay, significant fluorescent signal was detected from four sub-clones. The first three sub-clones were derived from shotgun databases (P1+P2, P9+P10 and P15+P16) (corresponding to cellulases of SEQ ID NOs. 10, 12 and 8) and the last one was from function-based screening (P16O17) (corresponding to the cellulase of SEQ ID NO. 2). The sequences of P1+P2, P9+P10 and P15+P16 are identical but have different lengths. P15+P16 is 63 bp and 117 bp shorter than P1+P2 and P9+P10, respectively. Despite its shorter length compared to these other two sub-clones, P15+P16 was observed to have the highest fluorescent signal in the MUC assay and did not have noticeable reduction in cellulase activity after being heated at 80° C. (FIG. 2). In contrast, the cellulase activity of the sub-clones P1+P2 and P9+P10 are much lower and were observed to have decreased activity after heating at 80° C. with significant difference to that at 37° C. and 60° C. (FIG. 2). Interestingly, the sub-clone from the P16O17 fosmid clone showed a significantly higher cellulase activity after heating at 60° C. and 80° C. compared to its activity at 37° C. (FIG. 2).

Heat stability and activity of the cellulase enzymes were also analysed in crude cell extracts as well as isolated protein (Ni-NTA affinity chromatography). Activity per mg protein in extracts containing cellulases P1+2, P15+16 and P16O17 all showed significantly higher activity compared to the negative control. The P9+10 cellulase activity showed lower activity compared to the others cellulase candidates, but still higher than the observed background (FIG. 3), indicating heat stability as well as cellulase activity in all enzymes characterized. Activity assay was also performed using isolated protein, where the first elution fraction (eluted with 100 mM imidazole) both untreated as well as heat incubated (65° C., 20 min) were used (FIG. 4). Isolated cellulase P9+10 did not show any significant activity in the assay, suggesting poor yield in isolation in combination with a lower level of activity. Cellulases P1+2 and P15+16 both showed activity as isolated proteins; however, a small decrease in activity was found after heat incubation of the isolated proteins (FIG. 4). For cellulase P16O17, the measured activity in the isolated protein sample was found to be remarkably higher compared to the other two candidates. In addition, the P16O17 cellulase candidate is apparently very heat stable and the observed activity/mg protein increased notably after heat incubation of the isolated protein, indicating P16O17 to be a very active as well as thermostable cellulase.

Cellulase Phylogenetic Analysis

All cellulase ORFs were collected together with a database of cellulase gene sequences, and a phylogenetic tree was constructed using PHYML to shed light on the evolutionary relationships of these cellulases. In the tree, the cellulase from P19+P20 was distantly related to other identified cellulases but clustered together with two known eukaryotic cellulases, forming a monophyletic group with that of Nicotiana tabacum (FIG. 5). The cellulase gene sequence that was repeatedly identified from five different fosmid pooled plates (P1+P2, P5+P6, P9+P10, P12+P24, and P15+P16) formed a monophyletic group with an archaeal cellulase from *Pyrococcus abyssi* (FIG. 5). The first cellulase identified from clone P17M3 was affiliated with an archaeal cellulase identified from *Pyrococcus horikoshii* (FIG. 5). In contrast, the second cellulase from clone P17M3 was affiliated with the cellulases from clones P17H9, P16O17 and P8E14 (which had identical predicted amino acid sequences), and the closest relative of these four novel cellulases is an archaeal cellulase from *Pyrococcus furiosus* (FIG. 5). Cellulases with an identical amino acid sequence from clones P4C10 and P17C9 as well as from pooled plates P3+P4 were affiliated with bacterial cellulases from *Thermosipho africanus* and *Fervidobacterium nodosum* (FIG. 5). The phylogenetic analysis supports the monophyly of these bacterial and archaeal cellulases, and indicates that the thermostable cellulases identified in this study from Archaea represent novel clades, whereas the bacterial-derived cellulases were closely related to previously identified cellulases.

Discussion

It was observed that the oil reservoir sample was dominated by members of the domain Archaea, phylum *Euryarchaeota*, with sequences recovered either from shotgun sequencing or from a fosmid metagenomic library indicating more than 60% of all significant hits to these archaeal taxa (FIG. 1A). For other phyla, only three were present in shotgun or library sequence databases at greater than 0.1% relative abundance, with a range of 6.7% to 11.2% *Proteobacteria*, 2.3% to 2.4% *Firmicutes* and 0.1% to 0.14% *Thermotogae*, respectively. At a genus level, *Thermococcus* and *Pyrococcus* were the most abundant genera with about 22% and 4% of the significant hits, respectively (data not shown). The results obtained from shotgun sequences and from the metagenomic library were highly comparable in terms of phylogenetic and functional composition (FIG. 1A) and exhibited an overall low diversity as expected due to the high pressure (250 bars) and temperature (85° C.) in this environment. The alpha-diversity of the shotgun sequences database as determined based on Shannon's Diversity Index is 42.08 species, which as expected is relatively low compared to non-extreme environments. It was observed that taxa affiliated with the bacterial phyla *Proteobacteria* and *Bacteroidetes* had different abundances between these two sequence databases (FIG. 1A), which could reflect a bias in the amplification and/or cloning of genomic DNA from these bacteria. Given the observations that the Archaea are dominant in this environment, that most of the enzymes obtained in this study are derived from taxa affiliated with the *Euryarchaeota*, and the extreme nature of these habitats, it is concluded that the sampling of these oil reservoir microbial assemblages has been inclusive of much of the extant phylogenetic and functional diversity. The large number of unassigned sequences from both shotgun and library sources indicates that even though this is an extreme habitat with limited phylogenetic breadth that there is a considerable amount of previously unknown metagenomic diversity in the sampled environment.

Inferences of the functional capacity of these oil reservoir microorganisms gleaned from MG-RAST output indicated that carbohydrate-degrading enzymes are frequently encoded within the archaeal and bacterial genomes (FIG. 1B). However, crude oil consists primarily of hydrocarbons of various molecular weights, and one would predict that only small amounts of carbohydrates such as cellulose, starch and xylan, if any, exist in deep sub-surface oil reservoirs. While the concentrations of these carbohydrates were not determined from oil samples, the assumption is that these carbohydrates are present in limited amounts and are probably from remnant biomass. Alternative functions of polysaccharide hydrolases in organisms from oil reservoir samples may be in the metabolism of storage polysaccharides or extracellular polysaccharides (EPS) formed by many organisms, including hyperthermophilic Archaea. In addition, it was observed that many of the CAZymes discovered from sequence- or function-based screening were redundant, indicating that the methods used had sufficiently exhausted much of the enzymatic diversity present in these samples and that there is a limited overall diversity of CAZymes in this hyperthermal habitat. The surprising discovery of a cellulase gene that has homology with a cellulase from *Solanum lycopersicum*, the garden tomato, may indicate a potential gene transfer event or sample contamination. Four sub-clones were generated that were observed to have significant cellulase activity in the quantitative MUC assay. Both sub-clones from the pooled fosmid plates P15+P16 and fosmid clone P16O17 showed good thermal stability in the MUC assay at both 60° C. and 80° C. (SEQ ID Nos 8 and 2, respectively). Based on a comparison with the genomes of *P. abyssi* GE5 and *T. kodakarensis* KOD1, the % G+C content of the cellulase-containing contig P15+P16 is 52.5%, much closer to that of *T. kodakarensis* KOD1 (52.0%) compared to *P. abyssi* GE5 (44.7%). For the fosmid clone P16O17, we identified sequences by Illumina MiSeq sequencing and annotated five contigs that were larger than 1 kb. The top BLAST hits of the ORFs derived from these contigs were all members of the Family *Thermococcaceae*, Phylum *Euryarchaeota*, Domain Archaea. The five species represented by these top BLAST hits included *Thermococcus nautili, Thermococcus kodakarensis, Thermococcus eurythermalis, Pyrococcus horikoshii*, and *Pyrococcus furiosus*. The average % G+C content of all P16O17 contigs was 53.4%, which is closer to the three different *Thermococcus* spp. (range of 52%-54.8%) than to *Pyrococcus* spp. (range of 40.8%-41.9%). In addition, an analysis of codon usage from clone P16O17 sequences also supported an origin from *Thermococcus* spp. rather than *Pyrococcus* spp. (data not shown). These results suggest that both of the highly active and thermostable cellulases identified from this study were derived from thermophilic Archaea, and that expression of these archaeal cellulases was possible (at least in some cases) from native archaeal promoters expressed in an *E. coli* heterologous host.

The data indicates that the majority of the cloned cellulases, and other CAZymes, are affiliated with Archaea and Bacteria, particularly with taxa affiliated with the phylum *Euryarchaeota*. Interestingly, all of the bacteria-derived cellulases are affiliated with the glycoside hydrolase 5 category, with many Archaea-derived cellulases also in this clade from clones identified from functional screening, P17M3, P17H9, P16O17 and P8E14 (highlighted in red shadow, FIG. 3). In contrast, the archaeal cellulases classified within the category of glycoside hydrolase 12 were all identified from sequence-based screening (highlighted in blue shadow, FIG. 3). This suggests that the cellulases within the glycoside hydrolase 12 category were not expressed from their native promoters in an *E. coli* host. Alternatively, these cellulases may not have been detected in functional screening due to an inability to be secreted and/or active under the conditions used for functional screening.

Example 2

Substrate Specificity Analysis of Enzyme P16O17
Materials and Methods
Construction and Cloning of a Codon-Optimised Version of the P16O17 Gene for Heterologous Expression in *E. coli*.

The amino acid sequence of P16O17 (SEQ ID NO. 2) was used to generate an *Escherichia coli* codon-usage optimised gene version (SEQ ID NO. 21). The codon-optimised gene was synthesized and delivered by GenScript (Piscataway, N.J., USA) cloned in the vector backbone of pUC57. The P16O17 gene was then sub-cloned into the pRham N-His SUMO expression vector of the Expresso® Rhamnose SUMO Cloning and Expression System (Lucigen Inc., Middleton, Wis., USA) according to the manufacturer's protocol, i.e. amplification of the target gene using forward and reverse primers (SEQ ID NOs. 22 and 23, respectively), followed by recombination into the vector by overlapping sequence regions and transformation of chemically competent 'E. cloni® 10G' cells (Lucigen).

The target sequence of the cloned P16O17 gene was confirmed by sequencing using flanking primers, as well as by primer walking using several internal primers. The complete sequence of the cloned P16O17 gene in the context of the expression vector (i.e. with an N-terminal His-tag and SUMO tag), as well as the corresponding amino acid sequence encoded by the construct, are presented in SEQ ID NOs. 24 and 25, respectively. (The DNA and amino acid sequences of the His-tag are presented in SEQ ID NOs. 26 and 27 respectively, and the DNA and amino acid sequences of the SUMO tag are presented in SEQ ID NOs. 28 and 29, respectively). A graphical representation of the expression vector pRham-P16O17-optim is presented in FIG. 7.

Preparation of P16O17 Enzyme-Containing Cell Extract

'E. cloni' 10G (pSUMO-P16O17-optim), carrying the *E. coli* codon-usage optimised P16O17 gene variant in vector pRham N-His SUMO, was cultivated for enzyme production in 1000 ml LB medium containing 30 µg/ml kanamycin and 0.05% glucose. Cells were pre-cultured in LB medium containing 30 µg/ml kanamycin and 0.5% glucose at 37° C. and 225 rpm overnight and used as inoculum for the 1000 ml culture with a starting $OD_{600}$ of 0.042. The culture was cultivated at 37° C. and 225 rpm until $OD_{600}$=1.388, when the cells were washed to remove glucose and re-suspended in fresh LB with 30 µg/ml kanamycin and 0.2% rhamnose for induction of gene expression. The culture was incubated further until $OD_{600}$=4.55 (ca. 8.5 hr), and thereafter cell mass was harvested and stored at −20° C.

For crude cell extract preparation, cell mass was thawed and re-suspended in 20 ml 50 mM potassium acetate buffer pH 5.5, and sonicated for 9 min. with mixing every three min. (Branson Sonifier, 50% duty cycle, output control 4, TM-tip). Cell lysate was thereafter centrifuged at 15 000×g for 30 minutes at 4° C. The supernatant, termed crude cell extract (CCE), was thereafter heated at 65° C. for 20 minutes to precipitate heat-unstable host proteins, followed by centrifugation at 13 000×g for 5 minutes at 4° C. Remaining heated CCE was kept at 4° C.

Cellulase Enzyme Activity Assays:
4-MUC Assay

Enzyme activity in CCE was measured by an assay using 4-methylumbelliferyl-β-D-cellobiose (4-MUC) as a substrate. 100 µl 4-MUC was added to an equal volume of heated CCE in a 96 well plate. Four replicates were processed in parallel. Reactions were incubated at 37° C. overnight, after which fluorescence in each well was analysed (excitation/emission at 375/445 nm) using a BioTek Cytation 3 plate reader (Thermo Fisher Scientific Inc., USA).

Substrate Specificity Assay

Heated CCE containing P16O17 was used on two different cellulose substrates, either alone or in combination with one or two additional commercial cellulose-degrading enzymes.

a) Enzyme Reactions:

Substrates used were: A) Carboxymethyl cellulose (CMC; Sigma-Aldrich C5678), and B) microcrystalline cellulose (Avicel; Avicel® PH-101; Sigma-Aldrich 11363). The commercially available enzymes used were: I) endoglucanase (Sigma-Aldrich, E2164), II) cellobiohydrolase (Sigma-Aldrich, E6412), and III) beta-glucosidase (Sigma-Aldrich, 49290).

Reactions were performed and analyzed in a two-step procedure, with the initial step being enzymatic treatment of the substrate, and the second step the analysis of reaction products. Substrates A and B were treated with one or several enzymes, as shown in Table 3.

TABLE 3

Combinations of substrates and enzymes.

| Substrate | Enzyme |
|---|---|
| A or B | I |
| A or B | II |
| A or B | III |
| A or B | P16O17 |
| A or B | I + II |
| A or B | I + III |
| A or B | II + III |
| A or B | I + P16O17 |
| A or B | II + P16O17 |
| A or B | III + P16O17 |
| A or B | I + II + III |
| A or B | I + II + P16O17 |
| A or B | Buffer |

150 µl of substrate stock solution (10 g/l) was added to wells of a 96-well microtiter plate, followed by the enzyme(s). 20 µl of each enzyme (3×20 µl for three-enzyme reactions, 2×20 µl for two-enzyme reactions and 1×20 µl for one-enzyme reactions). Where necessary, 50 mM potassium acetate buffer pH 5.5 was used to bring he total volume added to each well to 60 µl. The amounts of enzyme added in the volume of 20 µl, were for (I) endoglucanase (Sigma E2164) 1.05 mg/ml (2.1 U), (II) cellobiohydrolase (Sigma E6412) 1.95 mg/ml (0.14 U) and (III) beta-glucosidase (Sigma 49290) 0.55 mg/ml (3.3 U).

Enzyme reactions were run in triplicate in 96-well microtiter plates at 50° C. for 60 min., followed by heat inactivation of the enzyme(s) at 90° C. for 15 min., followed by centrifugation (5 min. at 3220×g). The supernatant after centrifugation was used for analysis of the enzyme reaction products.

b) Product Detection:
i. By Enzymatic Detection of Glucose

Glucose as reaction product was quantitatively detected by the Amplex UltraRed assay (Molecular Probes, Thermo Fisher Scientific Inc.) in 96-well microtiter plate format. 50 µl hydrolysate from an enzyme reaction (above) was mixed with 50 µl pre-assembled reaction solution (0.1 mM Amplex UltraRed, 1 U HRP, 10 U glucose oxidase in phosphate buffer (pH 7.4), total volume 5 ml), then incubated in the dark for 15 min., after which fluorescence analysis was performed (excitation/emission at 530/590 nm). Amplex UltraRed detects $H_2O_2$, which is formed from free glucose by the glucose oxidase enzyme used in the reaction solution.

ii. By High Performance Anion Exchange Chromatography with Pulsed Amperometric Detection (HPAEC-PAD)

In addition, reaction products were analysed by HPAEC-PAD. Cellohexose (MegaZyme, Ireland) and Avicel® PH-101 (Sigma-Aldrich, 11363) were used as substrates, and incubation with P16O17 was performed as described above. Reaction mixtures without enzyme were used as references. HPAEC-PAD analysis was performed by applying reaction mixture to a 4×250 mm CarboPac PA100 column with guard and pulsed amperometric detection of glucose n-mers based on standards for glucose, cellobiose and cellohexose. A linear sodium acetate gradient from 10 to 410 mM sodium acetate in 100 mM NaOH was applied over a period of 60 minutes to separate glucose mono- and oligomers.

iii. By Liquid Chromatography-Mass Spectrometry (LC-MS)

The reaction products of P16O17 degradation of Avicel and CMC were also analysed by LC-MS, using a system consisting of an Agilent 1290 Infinity LC module linked to an Agilent 6490 QqQ MS and using jet-stream electrospray ionization (ESI) operated in negative mode with 3500 V and a nozzle voltage of 500 V in scan mode between 50 m/z and 1400 m/z. Gas temperature was 220° C., gas flow 20 L/min, nebulizer at 40 psi, sheath gas temperature at 400° C., and sheath gas flow at 11 L/min. Samples were run through an Acentis Express Phenylhexyl column (10 cm) to desalt the enzymatic reaction products. The mobile phase consisted of 50% acetonitrile in water with 25 mM ammonium acetate and was run isocratically. A glucose standard, as well as cellobiose dissolved in reaction buffer, were analysed as controls.

Results
4-MUC Activity Assay of Crude Cell Extract

Results from 4-MUC assays comprise activity of enzyme detected as fluorescence (shown in FIG. 8). Cellulase activity values are shown for P16O17 enzyme from codon-optimised gene expression (P16O17-optim) and non-codon-optimised gene expression (P16O17). The negative control used was CCE from cells not carrying the P16O17 gene. Both heated and non-heated extracts of each species were tested.

Determination of P16O17 Enzyme Amounts

Total protein content in heated CCE (used in cellulase substrate specificity analysis) was determined by Qbit measurement (performed according to the manufacturer's protocol) to be 3.04 mg/ml. However, the protein band corresponding to P16O17-optim (from codon-optimised gene expression) was not visible on an SDS-PAGE gel, and even Western blot analysis to detect the enzyme's N-terminal His-tag was not conclusive with respect to protein detection of the enzyme in the CCE sample (heated or non-heated). Based on the residual expression of host proteins stained in the SDS-PAGE of the heated CCE sample, it was estimated that due to the lack of P16O17-optim band detection, the P16O17-optim enzyme likely represents no more than 5% of the total protein content, i.e. <0.15 mg/ml. Despite being non-detectable by these methods, P16O17-optim was clearly present in the heated CCE, as evidenced by the exceptionally high cellulase activity shown to be present therein.

Cellulase Substrate Specificity Determination Using the Amplex UltraRed Enzyme Assay The Amplex UltraRed assay is used to detect glucose in reaction mixtures. However, when using cellobiose (Sigma-Aldrich, 22150) as an alternative substrate, the Amplex UltraRed assay gave positive signals even in the absence of enzyme, not allowing conclusions to be drawn from the enzyme assay when performed using this substrate. Based on this finding and its unknown reason, it is difficult to clearly differentiate between cellobiose and glucose as reaction products from enzymatic reactions using CMC and Avicel as substrates. The enzyme assay results using CMC and Avicel as substrates need to be evaluated taking this into account.

Enzyme P16O17-optim was found to be active on both substrate A (CMC) and substrate B (Avicel), both as a single enzyme and in combination, shown in FIGS. 9 and 10.

In contrast to enzymes I, II, and III, P16O17 appeared to be active on CMC as a single enzyme, and resulted in even higher fluorescence (H$_2$O$_2$ detected, and hence glucose produced) than an enzyme cocktail of enzymes I+II+III.

Similarly to the results using CMC as a substrate, P16O17 proved to be functional as a single enzyme when the microcrystalline cellulose Avicel was used as a substrate, which is not observed for enzymes I, II or III. It also showed higher activity compared to the cocktail of reference enzymes I+II+III.

The concentration of P16O17-optim enzyme in the stock solution used in the substrate specificity reaction assays is estimated to be (at most) 0.15 mg/ml, i.e. the amount used is (at most) 0.003 mg/well, which is still likely an overestimation of the actual amount of enzyme used. For comparison of amounts of the different enzymes used in the assayed enzyme reactions, see Table 4.

TABLE 4

Concentrations and amounts of enzymes in enzyme reactions.

| Enzyme | Stock Solution (mg/ml) | Enzyme/Well (mg) |
|---|---|---|
| Enzyme I | 1.05 | 0.021 |
| Enzyme II | 1.95 | 0.021 |
| Enzyme III | 0.55 | 0.011 |
| P16O17 (estimated) | 0.15 | 0.003 |

Cellulase Substrate Specificity Determination Using (HPAEC-PAD)

The results of enzymatic degradation of cellohexose and Avicel substrates by P16O17 are presented in FIG. 11.

Cellohexose is quantitatively degraded to mainly cellobiose, but surprisingly significant amounts of glucose and a side product that may be the trimer cellotriose are also produced. Avicel microcrystalline cellulose is degraded to cellobiose, though surprisingly a significant glucose peak is also observed in this case. No soluble oligomers larger than cellobiose are observed when Avicel is used as a substrate, indicating that P16O17 is mainly an exo-cellulase that processes cellulose polymers to form cellobiose and to some extent glucose without the need for additional enzymes. It can also be derived from these results that only substrates larger than cellotriose can be processed by the enzyme (given that no oligomers larger than cellobiose were obtained from Avicel degradation but cellotriose remained following cellohexose degradation).

Cellulase Substrate Specificity Determination Using Mass Spectrometry (LC-MS)

The analysis of the glucose standard by LC-MS revealed masses of 179 m/z and 215 m/z which correspond to the [M-H]- and [M+Cl]-ions, respectively, with the latter being the predominant ion species. The corresponding [M+Cl]-ion with 377 m/z was also obtained for cellobiose in reaction buffer without enzyme addition. No differences were observed though between cellobiose in reaction buffer without enzyme and with P16O17 enzyme added. The reaction of P16O17 with CMC resulted in several masses, one of which corresponded to cellobiose (377 m/z). Other, as yet unidentified masses detected in this reaction were 399, 561, 581, 619, and 662 m/z. P16O17 enzyme treatment of Avicel resulted in masses that corresponded to glucose and cellobiose, the latter having the highest intensity (FIG. 12). This confirms the findings of the ion chromatography analysis of P16O17, that P16O17 produces mainly cellobiose, but also produces glucose, from crystalline cellulose substrates.

Discussion

Of the four different enzymes tested on CMC and Avicel as substrates, the P16O17 enzyme is the only enzyme capable of acting on both the CMC and the Avicel substrate as a single enzyme, surprisingly producing (at least to some extent) glucose, as detected by Amplex UltraRed assay. In the Amplex UltraRed assay analyses, lower amounts of P16O17 were presumably used than of the reference enzymes I, II and III. Indeed, the estimated amount of P16O17 used was approximately ⅓ of the amount used of the least abundant reference enzyme (enzyme III, beta-glucosidase). Yet P16O17 activity is remarkably higher than that of enzyme III on both CMC and Avicel, indicating that P16O17 is highly active on polymeric cellulosic material. Addition of enzyme I, II or III to the reaction of P16O17 does not seem to generate more glucose in the CMC substrate reaction, which, however, might be due to the assay reaching its detection limit. For the Avicel substrate reaction, addition of enzyme III, beta-glucosidase, to P16O17 seems to slightly increase glucose amounts produced from cellobiose produced by P16O17.

Due to problems with specifically detecting glucose by the Amplex UltraRed assay when using cellobiose as a substrate, without addition of enzymes I, II, III or P16O17, it could not be elucidated using this assay whether the P16O17 enzyme actually produces glucose or cellobiose from CMC and Avicel, which then in turn can be used as substrate for H$_2$O$_2$ production by the glucose oxidase of the assay.

Therefore, chromatography-based methods were applied to clearly identify reaction products of the P16O17 reaction on Avicel, as well as to get further insight into substrate specificity and processivity of the enzyme. From both analyses (HPAEC-PAD and LC-MS using Avicel as substrate), it is clear that P16O17 acts on crystalline cellulosic material and produces primarily cellobiose, but surprisingly also to some extent glucose as a by-product. The enzyme obviously exhibits exo-activity on cellulose polymers as no soluble oligomers larger than cellobiose can be obtained from Avicel (in particular no cellotriose), while cellotriose is detected from processing cellohexose as a substrate. This indicates that P16O17 has activity only on substrates larger than three glucose units. In particular, the detection of significant amounts of glucose (in addition to the main degradation product cellobiose) is surprising and represents a potentially very valuable feature of this enzyme with respect to the degradation of (ligno)cellulosic biomass with a broad spectrum of applications in biorefining. The fact that the enzyme is highly thermostable and suitable for industrial processes at elevated temperature adds to its potential value as a cellulolytic enzyme for industrial processes.

The invention claimed is:

1. A method of degrading any one or more of cellulose, hemicellulose, lichenin and cereal beta-D-glucan or a material comprising cellulose, hemicellulose, lichenin and/or cereal beta-D-glucan, comprising incubating a polypeptide with said cellulose, hemicellulose, lichenin and/or cereal beta-D-glucan or a material comprising cellulose, hemicellulose, lichenin and/or cereal beta-D-glucan, wherein said polypeptide has a cellulase activity, is capable of degrading cellulose to glucose and is thermostable, and said polypeptide comprises:

the amino acid sequence set forth in SEQ ID NO. 2, or an amino acid sequence having at least 80% sequence identity to the entirety of SEQ ID NO. 2.

2. The method of claim 1, wherein said polypeptide comprises an amino acid sequence having at least 95% sequence identity to the entirety of SEQ ID NO. 2.

3. The method of claim 2, wherein the polypeptide comprises the amino acid sequence set forth in SEQ ID NO. 2.

4. A method of degrading any one or more of cellulose, hemicellulose, lichenin and cereal beta-D-glucan or a material comprising cellulose, hemicellulose, lichenin and/or cereal beta-D-glucan, comprising incubating a polypeptide with said cellulose, hemicellulose, lichenin and/or cereal beta-D-glucan or a material comprising cellulose, hem icellulose, lichenin and/or cereal beta-D-glucan, wherein said polypeptide has a cellulase activity and is thermostable, and said polypeptide comprises the amino acid sequence set forth in SEQ ID NO. 8, or an amino acid sequence having at least 80% sequence identity to the entirety of SEQ ID NO. 8.

5. The method of claim 4, wherein the polypeptide comprises an amino acid sequence having at least 95% sequence identity to the entirety of SEQ ID NO. 8.

6. The method of claim 5, wherein the polypeptide comprises the amino acid sequence set forth in SEQ ID NO. 8.

7. The method of claim 5, wherein the polypeptide comprises the amino acid sequence set forth in SEQ ID NO. 10.

8. The method of claim 5, wherein the polypeptide comprises the amino acid sequence set forth in SEQ ID NO. 12.

9. The method of claim 1, wherein the material comprising cellulose, hem icellulose, lichenin and/or cereal beta-D-glucan is lignocellulose.

10. The method of claim 1, further comprising production of a biofuel.

11. The method of claim 1, wherein a part of said amino acid sequence having at least 80% sequence identity to the entirety of SEQ ID NO. 2 has at least 90% sequence identity to the entirety of SEQ ID NO. 20.

12. The method of claim 11, wherein a first part of said amino acid sequence having at least 80% sequence identity to the entirety of SEQ ID NO. 2 has at least 90% sequence identity to the entirety of SEQ ID NO. 18, and a second part of said amino acid sequence having at least 80% sequence identity to the entirety of SEQ ID NO. 2 has at least 90% sequence identity to the entirety of SEQ ID NO. 20.

13. The method of claim 4, wherein the material comprising cellulose, hemicellulose, lichenin and/or cereal beta-D-glucan is lignocellulose.

14. The method of claim 4, further comprising production of a biofuel.

* * * * *